(12) United States Patent
Kock et al.

(10) Patent No.: US 11,773,397 B2
(45) Date of Patent: *Oct. 3, 2023

(54) MODIFIED EXCISABLE DAS59122-7 MAIZE TRANSGENIC LOCUS

(71) Applicant: INARI AGRICULTURE TECHNOLOGY, INC., Cambridge, MA (US)

(72) Inventors: Michael Andreas Kock, Rheinfelden (DE); Joshua L. Price, Cambridge, MA (US); Michael Lee Nuccio, Salem, NH (US)

(73) Assignee: INARI AGRICULTURE TECHNOLOGY, INC., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/058,081

(22) Filed: Nov. 22, 2022

(65) Prior Publication Data

US 2023/0078387 A1    Mar. 16, 2023

Related U.S. Application Data

(63) Continuation of application No. PCT/US2021/043919, filed on Jul. 30, 2021.

(Continued)

(51) Int. Cl.
*C12N 15/82* (2006.01)
*C12Q 1/6895* (2018.01)
(Continued)

(52) U.S. Cl.
CPC ........... *C12N 15/8201* (2013.01); *A01H 5/10* (2013.01); *A01H 6/4684* (2018.05); *A01H 6/542* (2018.05);
(Continued)

(58) Field of Classification Search
None
See application file for complete search history.

(56) References Cited

U.S. PATENT DOCUMENTS 7,632,985 B2    12/2009  Malven et al.
7,956,246 B2 *   6/2011  Bing et al. ........... C12Q 1/6895
                                                    800/320.1

(Continued)

FOREIGN PATENT DOCUMENTS

CN       104830860 A     8/2015
WO      2022026375 A1    2/2022
(Continued)

OTHER PUBLICATIONS

Gleditzsch et al. "PAM identification by CRISPR-Cas effector complexes: diversified mechanisms and Structures" 2019 RNA Biology 16(4): 504-517. (Year: 2019).*

(Continued)

*Primary Examiner* — Matthew R Keogh
*Assistant Examiner* — Rebecca Stephens
(74) *Attorney, Agent, or Firm* — McKee, Voorhees & Sease, PLC

(57) ABSTRACT

Transgenic INIR4 maize plants comprising modifications of the DAS59122-7 maize locus which provide for facile excision of the modified DAS59122-7 transgenic locus or portions thereof, methods of making such plants, and use of such plants to facilitate breeding are disclosed.

Figure 1:
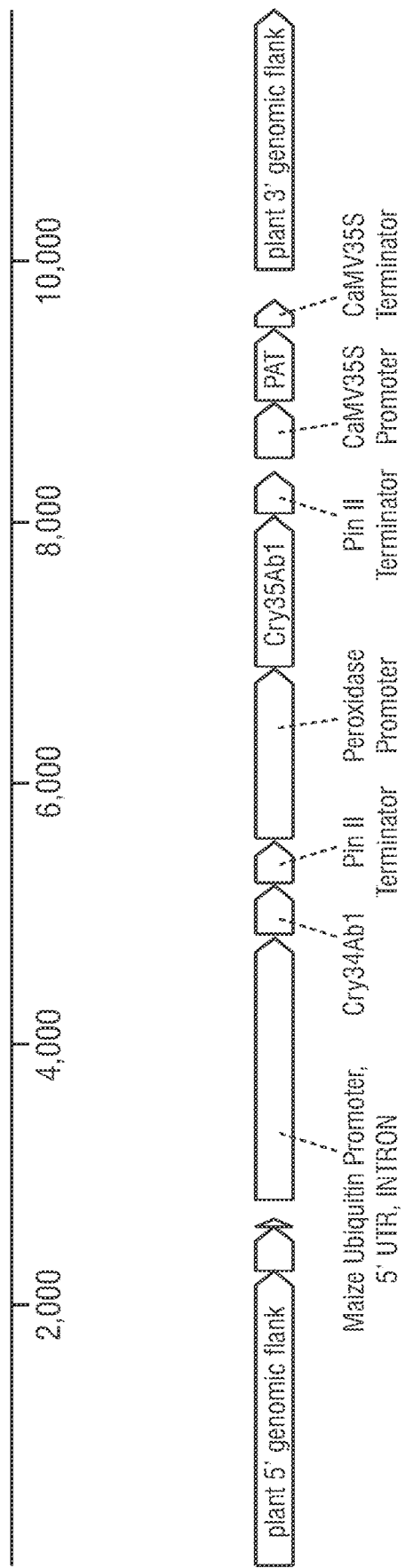

13 Claims, 5 Drawing Sheets
Specification includes a Sequence Listing.

Related U.S. Application Data

(60) Provisional application No. 63/203,137, filed on Jul. 9, 2021, provisional application No. 63/202,569, filed on Jun. 16, 2021, provisional application No. 63/201,030, filed on Apr. 9, 2021, provisional application No. 63/201,029, filed on Apr. 9, 2021, provisional application No. 63/199,951, filed on Feb. 4, 2021, provisional application No. 63/199,949, filed on Feb. 4, 2021, provisional application No. 63/199,930, filed on Feb. 3, 2021, provisional application No. 63/059,813, filed on Jul. 31, 2020, provisional application No. 63/059,963, filed on Jul. 31, 2020, provisional application No. 63/059,916, filed on Jul. 31, 2020, provisional application No. 63/059,860, filed on Jul. 31, 2020.

(51) Int. Cl.
| | |
|---|---|
| C12N 9/22 | (2006.01) |
| C12N 15/11 | (2006.01) |
| A01H 6/54 | (2018.01) |
| A01H 5/10 | (2018.01) |
| C12Q 1/6834 | (2018.01) |
| A01H 6/46 | (2018.01) |

(52) U.S. Cl.
CPC ............... *C12N 9/22* (2013.01); *C12N 15/11* (2013.01); *C12N 15/8213* (2013.01); *C12N 15/8286* (2013.01); *C12Q 1/6834* (2013.01); *C12Q 1/6895* (2013.01); *C12N 2310/20* (2017.05); *C12N 2800/80* (2013.01); *C12Q 2600/13* (2013.01)

(56) References Cited

U.S. PATENT DOCUMENTS

| | | |
|---|---|---|
| 8,232,456 B2 | 7/2012 | Long et al. |
| 8,450,561 B2 | 5/2013 | Beazley et al. |
| 8,455,198 B2 | 6/2013 | Gao et al. |
| 8,455,720 B2 | 6/2013 | Long et al. |
| 8,466,346 B2 | 6/2013 | DeFramond et al. |
| 8,575,434 B2 | 11/2013 | Diehn et al. |
| 8,680,363 B2 | 3/2014 | Bard et al. |
| 9,187,756 B2 | 11/2015 | Nuccio |
| 9,428,765 B2 | 8/2016 | Anderson et al. |
| 9,447,428 B2 | 9/2016 | Brinker et al. |
| 9,540,655 B2 | 1/2017 | Cui et al. |
| 9,738,904 B2 | 8/2017 | Cui et al. |
| 9,944,944 B2 | 4/2018 | Cui et al. |
| 11,041,172 B2 | 6/2021 | Cermak |
| 11,214,811 B1 | 1/2022 | Nuccio et al. |
| 11,242,534 B1 | 2/2022 | Nuccio et al. |
| 11,359,210 B2 | 6/2022 | Price et al. |
| 2003/0088081 A1 | 5/2003 | Maliga et al. |
| 2010/0162428 A1 | 6/2010 | Brown et al. |
| 2011/0191877 A1 | 8/2011 | Russell et al. |
| 2011/0191899 A1 | 8/2011 | Ainley et al. |
| 2013/0333071 A1 | 12/2013 | Boukharov et al. |
| 2014/0162272 A1 | 6/2014 | Long et al. |
| 2014/0196169 A1 | 7/2014 | D'Halluin et al. |
| 2015/0059010 A1 | 2/2015 | Cigan et al. |
| 2015/0082478 A1 | 3/2015 | Cigan et al. |
| 2016/0333363 A1 | 11/2016 | Srivastava |
| 2017/0166912 A1 | 6/2017 | Brower-Toland et al. |
| 2018/0057878 A1* | 3/2018 | Bing et al. ............ C07K 14/415 |
| 2018/0163218 A1 | 6/2018 | Corbin et al. |
| 2019/0136249 A1 | 5/2019 | Sakai et al. |
| 2019/0284644 A1 | 9/2019 | Mackenzie et al. |
| 2019/0320607 A1 | 10/2019 | Christensen et al. |
| 2019/0352655 A1 | 11/2019 | Niu et al. |
| 2020/0157554 A1 | 5/2020 | Cigan et al. |
| 2020/0399626 A1 | 12/2020 | Liu et al. |
| 2020/0405649 A1 | 12/2020 | Wang et al. |
| 2021/0274783 A1 | 9/2021 | Chae |
| 2022/0030806 A1 | 2/2022 | Price et al. |
| 2022/0030822 A1 | 2/2022 | Nuccio et al. |
| 2022/0033833 A1 | 2/2022 | Gilbertson et al. |
| 2022/0033836 A1 | 2/2022 | Price et al. |
| 2022/0098602 A1 | 3/2022 | Nuccio et al. |
| 2022/0154194 A1 | 5/2022 | Nuccio et al. |
| 2022/0251584 A1 | 8/2022 | Nuccio et al. |
| 2022/0364105 A1 | 11/2022 | Price et al. |
| 2023/0077473 A1 | 3/2023 | Price et al. |
| 2023/0078387 A1 | 3/2023 | Kock et al. |
| 2023/0083144 A1 | 3/2023 | Nuccio et al. |
| 2023/0087222 A1 | 3/2023 | Kock et al. |
| 2023/0147013 A1 | 5/2023 | Nuccio et al. |

FOREIGN PATENT DOCUMENTS

| | | |
|---|---|---|
| WO | 2022026379 A1 | 2/2022 |
| WO | 2022026390 A1 | 2/2022 |
| WO | 2022026395 A2 | 2/2022 |
| WO | 2022026403 A2 | 2/2022 |
| WO | 2022026540 A1 | 2/2022 |
| WO | 2022026801 A1 | 2/2022 |

OTHER PUBLICATIONS

Rudgers and Sastry-Dent "EXZACT™ Precision Technology: Scientific and Regulatory Advancements in Plant-Genome Editing with ZFNs" at pp. 113-124 in the 2014 NABC Report 26 on New DNA-Editing Approaches (Methods, Applications & Policy for Agriculture), Eaglesham & Hardy, Eds. (255 total pages). (Year: 2014).*

Danilo et al. "The DFR locus: A smart landing pad for targeted transgene insertion in tomato" 2018 PLoS ONE 13(12): e0208395 (14 total pages). (Year: 2018).*

Shi et al. "ARGOS8 variants generated by CRISPR-Cas9 improve maize grain yield under field drought stress conditions" 2017 Plant Biotechnology J. 15:207-216 (Year: 2017).*

Baliga et al., "Investigation of direct repeats, spacers and proteins associated with clustered regularly interspaced short palindromic repeat (CRISPR) system of Vibrio parahaemolyticus," Molecular Genetics and Genomics, Oct. 24, 2018, vol. 294, pp. 253-262.

Biopesticides Registration Action Document, "Bacillus thuringiensis Vip3Aa20 Insecticidal Protein and the Genetic Material Necessary for Its Production (via Elements of Vector pNOV1300) in Event MIR162 Maize (OECD Unique Identifier: SYN-IR162-4)," PC Code: 006599, U.S. Environmental Protection Agency, Office of Pesticide Programs, Biopesticides and Pollution Prevention Division, Mar. 2009, 175 pages.

Bissler, J.J., "Triplex DNA and human disease," Frontiers in Bioscience, May 1, 2007, vol. 12, pp. 4536-4546.

Bortesi et al., "The CRISPR/Cas9 system for plant genome editing and beyond," Biotechnology Advances, Dec. 20, 2014, vol. 33, Issue 1, pp. 41-52.

Charpentier et al., "Biogenesis pathways of RNA guides in archaeal and bacterial CRISPR-Cas adaptive Immunity," FEMS Microbiology Reviews, May 19, 2015, vol. 39, Issue 3, pp. 428-441.

Cho et al., "Nonallelic homologous recombination events responsible for copy No. variation within an RNA silencing locus," Plant Direct, vol. 3, Aug. 27, 2019, 16 pages.

Du et al., "Construction of Marker-Free Genetically Modified Maize Using a Heat-Inducible Auto-Excision Vector," Genes, May 17, 2019, vol. 10, No. 374, 17 pages.

Du et al., "Infection of Embryonic Callus with Agrobacterium Enables High-Speed Transformation of Maize," International Journal of Molecular Sciences, Jan. 11, 2019, vol. 20, No. 279, 15 pages.

Finnigan et al., "mCAL: A New Approach for Versatile Multiplex Action of Cas9 Using One sgRNA and Loci Flanked by a Programmed Target Sequence," G3: Genes, Genomes, Genetics, Jul. 1, 2016, vol. 6, pp. 2147-2156.

Gurusaran et al., "RepEx: Repeat extractor for biological sequences," Genomics, Jul. 21, 2013, vol. 102, pp. 403-408.

(56) References Cited

OTHER PUBLICATIONS

International Searching Authority in connection with PCT/US21/43897 filed Jul. 30, 2021, "Invitation to Pay Additional Fees and, Where Applicable, Protest Fee," dated Oct. 27, 2021, 3 pages.
International Searching Authority in connection with PCT/US21/43935 filed Jul. 30, 2021, "Invitation to Pay Additional Fees and, Where Applicable, Protest Fee," dated Oct. 26, 2021, 3 pages.
International Searching Authority in connection with PCT/US21/43945 filed Jul. 30, 2021, "Invitation to Pay Additional Fees and, Where Applicable, Protest Fee," dated Oct. 27, 2021, 3 pages.
Kim et al., "CRISPR/Cpf1-mediated DNA-free plant genome editing," Nature Communications, Feb. 16, 2017, vol. 8, Article No. 14406, 7 pages.
Li et al., "Expanding the Scope of CRISPR/Cpf1-Mediated Genome Editing in Rice," Molecular Plant, Jul. 2, 2018, vol. 11, No. 7, pp. 995-998, 14 pages.
Luo et al., "Improperly Terminated, Unpolyadenylated mRNA of Sense Transgenes is Targeted by RDR6-Mediated RNA Silencing in *Arabidopsis*," The Plant Cell, Mar. 23, 2007, vol. 19, pp. 943-958.
Malzahn et al., "Application of CRISPR-Cas12a temperature sensitivity for improved genome editing in rice, maize, and *Arabidopsis*," BMC Biology, Jan. 31, 2019, vol. 17, No. 9, 14 pages.
Non-Final Office Action in U.S. Appl. No. 17/248,936, dated Mar. 25, 2021, 25 pages.
Non-Final Office Action in U.S. Appl. No. 17/249,640, dated Jun. 29, 2021, 10 pages.
Non-Final Office Action in U.S. Appl. No. 17/302,110, dated Jun. 29, 2021, 22 pages.
Non-Final Office Action in U.S. Appl. No. 17/302,121, dated Jul. 8, 2021, 10 pages.
Non-Final Office Action in U.S. Appl. No. 17/302,739, dated Aug. 3, 2021, 24 pages.
Notice of Allowance in U.S. Appl. No. 17/249,640, dated Sep. 22, 2021, 7 pages.
Que et al., "Maize transformation technology development for commercial event generation," Frontiers in Plant Science, Aug. 5, 2014, vol. 5, Article No. 379, 19 pages.
Srivastava et al., "Gene Stacking by recombinases," Plant Biotechnology Journal, Feb. 2016, vol. 14, pp. 471-482.
Srivastava, et al., "Dual-targeting by CRISPR/Cas9 for precise excision of transgenes from rice genome," Plant Cell Tissue and Organ Culture, Jan. 20, 2017, vol. 129, pp. 153-160.
Ward et al., "Petition for Determination of Nonregulated Status for Insect-Resistant MIR162 Maize," Syngenta Biotechnology, Inc., Aug. 31, 2007, 271 pages.
"What is a CRISPR-Cas system?," CRISPR-CAS++, Universite Paris-Saclay, accessed Nov. 2, 2021. Retrieved from the Internet <URL:https://crisprcas.i2bc.paris-saclay.fr/Home/About>, 2 pages.
Xing et al., "Revealing frequent alternative polyadenylation and widespread low-level transcription read-through of novel plant transcription terminators," Plant Biotechnology Journal, Sep. 2010, vol. 8, pp. 772-782.
Young et al., "CRISPR-Cas9 Editing in Maize: Systematic Evaluation of Off-target Activity and Its Relevance in Crop Improvement," Scientific Reports, Apr. 30, 2019, vol. 9, No. 6729, 11 pages.
Begemann et al., "Precise insertion and guided editing of higher plant genomes using Cpf1 CRISP nucleases," Scientific Reports, Sep. 14, 2017, vol. 76, No. 11606, pp. 1-6.
Begemann et al., "Supplementary Data—Precise insertion and guided editing of higher plant genomes using Cpf1 CRISP nucleases," Scientific Reports, Sep. 14, 2017, vol. 76, No. 11606, pp. 1-6.
Forsyth et al., "Transcription Activator-Like Effector Nucleases (TALEN)-Mediated Targeted DNA Insertion in Potato Plants," Frontiers in Plant Science, Oct. 2016, vol. 7, No. 1572, pp. 1-12.
International Search Report in PCT/US2021/043161, dated Jan. 5, 2022, 6 pages.
International Search Report in PCT/US2021/043170, dated Jan. 5, 2022, 6 pages.
International Search Report in PCT/US2021/043187, dated Jan. 5, 2022, 6 pages.
International Search Report in PCT/US2021/043192, dated Jan. 5, 2022, 7 pages.
International Search Report in PCT/US2021/043207, dated Jan. 27, 2022, 6 pages.
International Search Report in PCT/US2021/043440, dated Dec. 2, 2021, 3 pages.
International Search Report in PCT/US2021/043468, dated Nov. 26, 2021, 4 pages.
International Search Report in PCT/US2021/043479, dated Nov. 23, 2021, 3 pages.
International Search Report in PCT/US2021/043483, dated Dec. 16, 2021, 3 pages.
International Search Report in PCT/US2021/043496, dated Dec. 9, 2021, 4 pages.
International Search Report in PCT/US2021/043851, dataed Dec. 30, 2021, 6 pages.
International Search Report in PCT/US2021/043919, dated Jan. 20, 2022, 8 pages.
International Search Report in PCT/US2021/043933, dated Dec. 30, 2021, 6 pages.
International Search Report in PCT/US2021/044198, dated Jan. 19, 2022, 6 pages.
Mookan et al., "Selectable marker independent transformation of recalcitrant maize inbred B73 and sorgum P898012 mediated by morphogenic regulators BABY BOOM and WUSCHEL2," Plant Cell Reports, 2017, vol. 36, pp. 1477-1491.
Non-Final Office Action in U.S. Appl. No. 17/680,647, dated Jun. 23, 2022, 11 pages.
Non-Final Office Action in U.S. Appl. No. 18/057,860, dated Jun. 1, 2023, 49 pages.
Non-Final Office Action in U.S. Appl. No. 18/057,867, dated Jun. 7, 2023, 17 pages.
Non-Final Office Action in U.S. Appl. No. 18/058,144, dated Jun. 7, 2023, 49 pages.
Non-Final Office Action in U.S. Appl. No. 18/162,134, dated Jun. 21, 2023, 28 pages.
Notice of Allowance in U.S. Appl. No. 17/248,936, dated Mar. 10, 2022, 7 pages.
Notice of Allowance in U.S. Appl. No. 17/302,739, dated Mar. 30, 2022, 7 pages.
Zhang et al., "Off-target Effects in CRISPR/Cas9-mediated Genome Engineering," Official Journal of the American Society of Gene & Cell Therapy, 2015, vol. 4, No. e264, pp. 1-8.
Zhong et al., "Plant genome editing using FnCpf1 and LbCpf1 nucleases at redefined and altered PAM sites," Molecular Plant, 2018, vol. 11, No. 7, pp. 999-1002.
Zhong et al., "Supplementary Data—Plant genome editing using FnCpf1 and LbCpf1 nucleases at redefined and altered PAM sites," Molecular Plant, 2018, vol. 11, No. 7, pp. 999-1002.
Eaglesham et al., "New DNA-Editing Approaches: Methods, Applications & Policy for Agriculture," North American Agricultural Biotechnology Council Report, NABC Report 26, 2014, 255 pages.
Yau et al., "Less is more: strategies to remove marker genes from transgenic plants," BMC Biotechnology, 2013, vol. 13, No. 36, 23 pages.
Office Action in U.S. Appl. No. 18/058,161, dated Apr. 11, 2023, 23 pages.
Office Action in U.S. Appl. No. 18/058,156, dated May 19, 2023, 32 pages.

* cited by examiner

MODIFIED EXCISABLE DAS59122-7 MAIZE TRANSGENIC LOCUS

CROSS-REFERENCE TO RELATED APPLICATIONS

This is a continuation application of International Application No. PCT/US2021/043,919, filed on Jul. 30, 2021, which claims the benefit of priority to U.S. Provisional Patent Application No. 63/203,137, filed on Jul. 9, 2021, U.S. Provisional Patent Application No. 63/202,569, filed on Jun. 16, 2021, U.S. Provisional Patent Application Nos. 63/201,030 and 63/201,029, filed on Apr. 9, 2021, U.S. Provisional Patent Application Nos. 63/199,951 and 63/199,949, filed on Feb. 4, 2021, U.S. Provisional Patent Application No. 63/199,930, filed on Feb. 3, 2021, and U.S. Provisional Patent Application Nos. 63/059,813, 63/059,860, 63/059,916, and 63/059,963, filed on Jul. 31, 2020, each of which are incorporated herein by reference in their entireties.

REFERENCE TO SEQUENCE LISTING SUBMITTED ELECTRONICALLY

The instant application contains a Sequence Listing which has been submitted electronically in XML formatted and is herein incorporated by reference in its entirety. Said XML copy, created on Nov. 18, 2022, is named "P13647US00_SequenceListing.xml" and is 121,206 bytes in size.

BACKGROUND

Transgenes which are placed into different positions in the plant genome through non-site specific integration can exhibit different levels of expression (Weising et al., 1988, Ann. Rev. Genet. 22:421-477). Such transgene insertion sites can also contain various undesirable rearrangements of the foreign DNA elements that include deletions and/or duplications. Furthermore, many transgene insertion sites can also comprise selectable or scoreable marker genes which in some instances are no longer required once a transgenic plant event containing the linked transgenes which confer desirable traits are selected.

Commercial transgenic plants typically comprise one or more independent insertions of transgenes at specific locations in the host plant genome that have been selected for features that include expression of the transgene(s) of interest and the transgene-conferred trait(s), absence or minimization of rearrangements, and normal Mendelian transmission of the trait(s) to progeny. An example of a selected transgenic corn event which confers coleopteran insect pest tolerance is the DAS59122-7 transgenic maize event disclosed in U.S. Pat. No. 7,956,246. DAS59122-7 transgenic maize plants express Cry34Ab1 as well as Cry35Ab1 proteins which can confer resistance to coleopteran insect infestations (e.g., *Western corn rootworm (Diabrotica virgifera virgifera)*, *Northern corn rootworm (Diabrotica barberi)*, and *Southern corn rootworm (Diabrotica undecimpunctata howardi)*).

Methods for removing selectable marker genes and/or duplicated transgenes in transgene insertion sites in plant genomes involving use of site-specific recombinase systems (e.g., cre-lox) as well as for insertion of new genes into transgene insertion sites have been disclosed (Srivastava and Ow; Methods Mol Biol, 2015,1287:95-103; Dale and Ow, 1991, *Proc. Natl Acad. Sci. USA* 88, 10558-10562; Srivastava and Thomson, Plant Biotechnol J, 2016; 14(2):471-82). Such methods typically require incorporation of the recombination site sequences recognized by the recombinase at particular locations within the transgene.

SUMMARY

Transgenic maize plant cells comprising an INIR4 transgenic locus comprising an originator guide RNA recognition site (OgRRS) in a first DNA junction polynucleotide of a DAS59122-7 transgenic locus and a cognate guide RNA recognition site (CgRRS) in a second DNA junction polynucleotide of the DAS59122-7 transgenic locus are provided. Transgenic maize plant cells comprising an INIR4 transgenic locus comprising an insertion and/or substitution in a DNA junction polynucleotide of a DAS59122-7 transgenic locus of DNA comprising a cognate guide RNA recognition site (CgRRS) are provided. In certain embodiments, the DAS59122-7 transgenic locus is set forth in SEQ ID NO:1, is present in seed deposited at the ATCC under accession No. PTA-11384 is present in progeny thereof, is present in allelic variants thereof, or is present in other variants thereof. INIR4 transgenic maize plant cells, transgenic maize plant seeds, and transgenic maize plants all comprising a transgenic locus set forth in SEQ ID NO: 2, 3, 17, 23, 26, 27, or an allelic variant thereof are provided. Transgenic maize plant parts including seeds and transgenic maize plants comprising the maize plant cells are also provided.

Methods for obtaining a bulked population of inbred seed comprising selfing the aforementioned transgenic maize plants and harvesting seed comprising the INIR4 transgenic locus from the selfed maize plant are also provided.

Methods of obtaining hybrid maize seed comprising crossing the aforementioned transgenic maize plants to a second maize plant which is genetically distinct from the first maize plant and harvesting seed comprising the INIR4 transgenic locus from the cross are provided. Methods for obtaining a bulked population of seed comprising selfing a transgenic maize plant comprising the transgenic locus set forth in SEQ ID NO: 2, 3, 17, 23, 26, 27, or an allelic variant thereof and harvesting transgenic seed comprising the transgenic locus set forth in SEQ ID NO: 2, 3, 17, 23, 26, 27, or an allelic variant thereof are provided.

A DNA molecule comprising SEQ ID NO: 2, 3, 8, 9, 10, 11, 16, 17, 23, 24, 26, 27, or 28 is provided. Processed transgenic maize plant products and biological samples comprising the DNA molecules are provided. Nucleic acid molecules adapted for detection of genomic DNA comprising the DNA molecules, wherein said nucleic acid molecule optionally comprises a detectable label are provided. Methods of detecting a maize plant cell comprising an INIR4 transgenic locus, comprising the step of detecting a DNA molecule comprising SEQ ID NO: 2, 3, 8, 9, 10, 11, 16, 17, 23, 24, 26, 27, or 28 are provided.

Methods of excising the INIR4 transgenic locus from the genome of the aforementioned maize plant cells comprising the steps of: (a) contacting the edited transgenic plant genome of the plant cell with: (i) an RNA dependent DNA endonuclease (RdDe); and (ii) a guide RNA (gRNA) capable of hybridizing to the guide RNA hybridization site of the OgRRS and the CgRRS; wherein the RdDe recognizes a OgRRS/gRNA and a CgRRS/gRNA hybridization complex; and, (b) selecting a transgenic plant cell, transgenic plant part, or transgenic plant wherein the INIR4 transgenic locus flanked by the OgRRS and the CgRRS has been excised.

BRIEF DESCRIPTION OF THE DRAWINGS/FIGURES

FIG. 1 shows a diagram of transgene expression cassettes and selectable markers in the DAS59122-7 transgenic locus.

Figure 2:
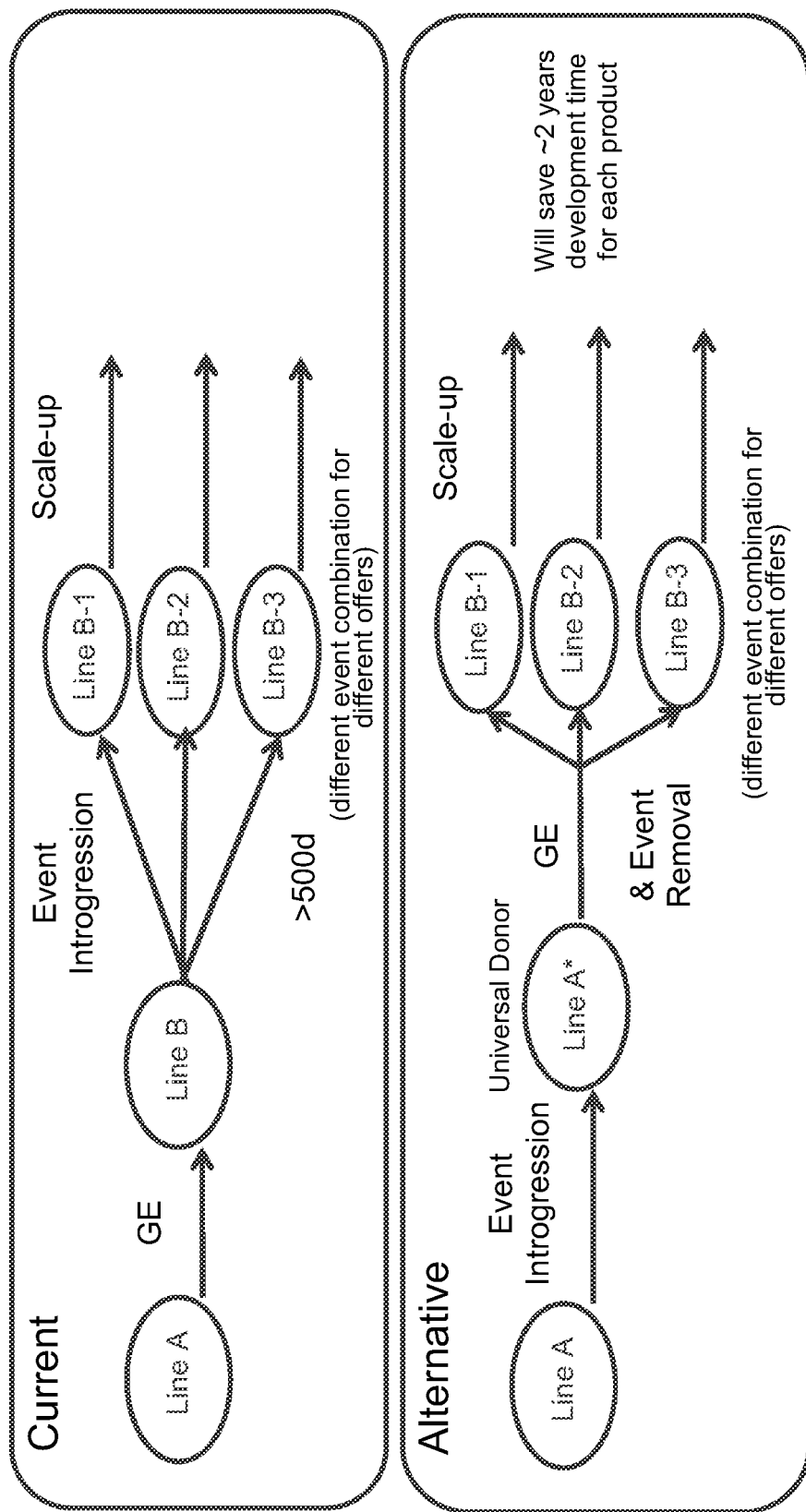

FIG. 2 shows a schematic diagram which compares current breeding strategies for introgression of transgenic events (i.e., transgenic loci) to alternative breeding strategies for introgression of transgenic events where the transgenic events (i.e., transgenic loci) can be removed following introgression to provide different combinations of transgenic traits. In FIG. 2, "GE" refers to genome editing (e.g., including introduction of targeted genetic changes with genome editing molecules and "Event Removal" refers to excision of a transgenic locus (i.e., an "Event") with genome editing molecules.

Figure 3A:
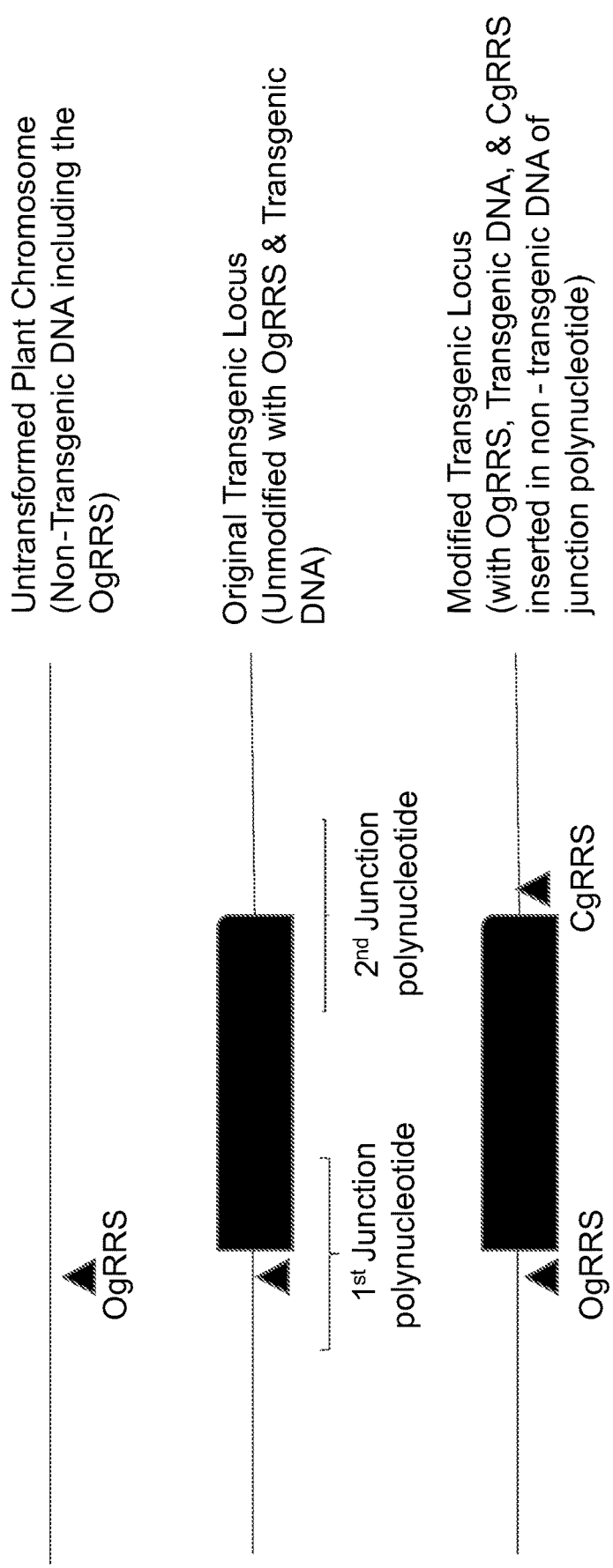
Figure 3B:
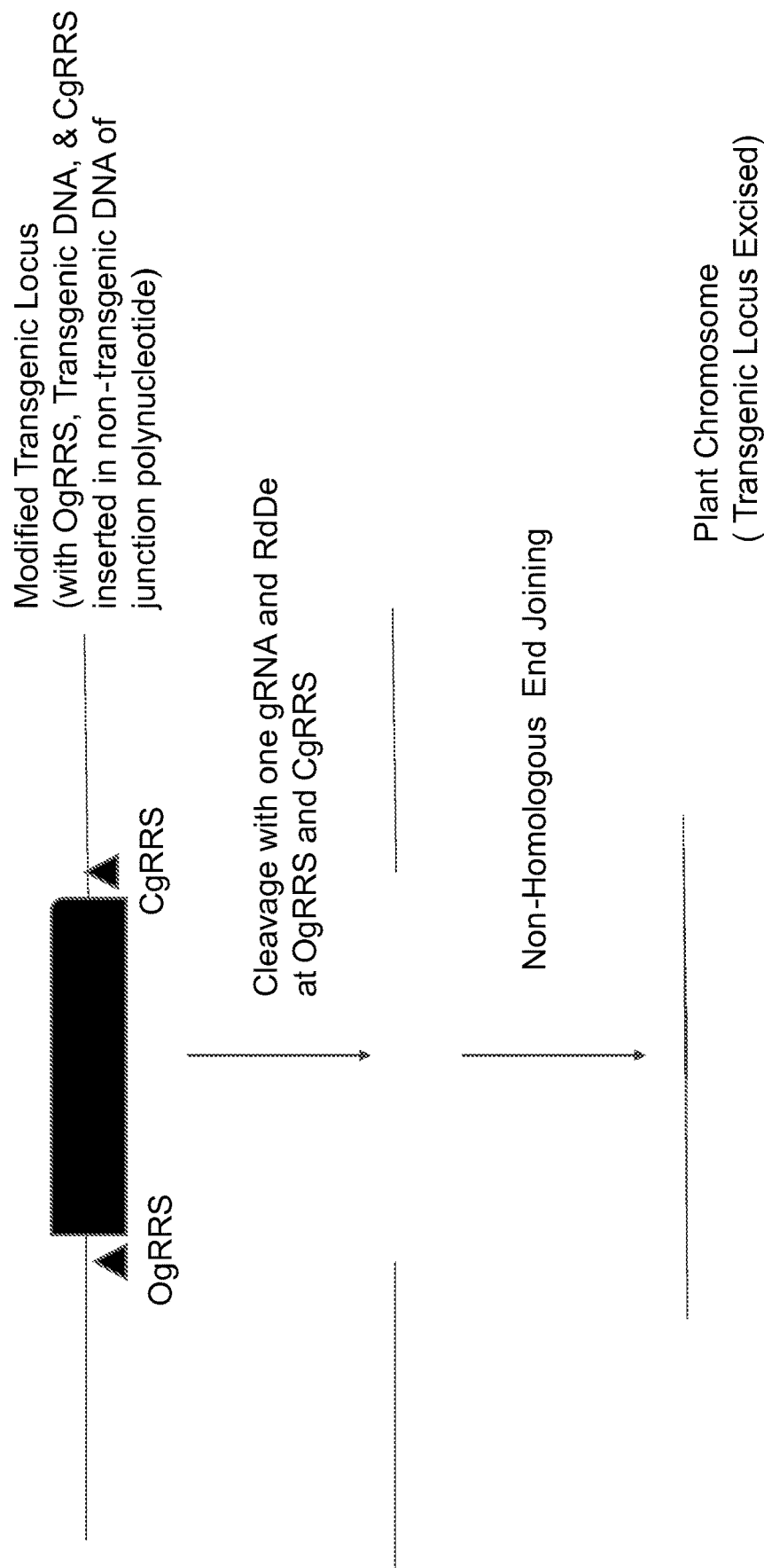
Figure 3C:
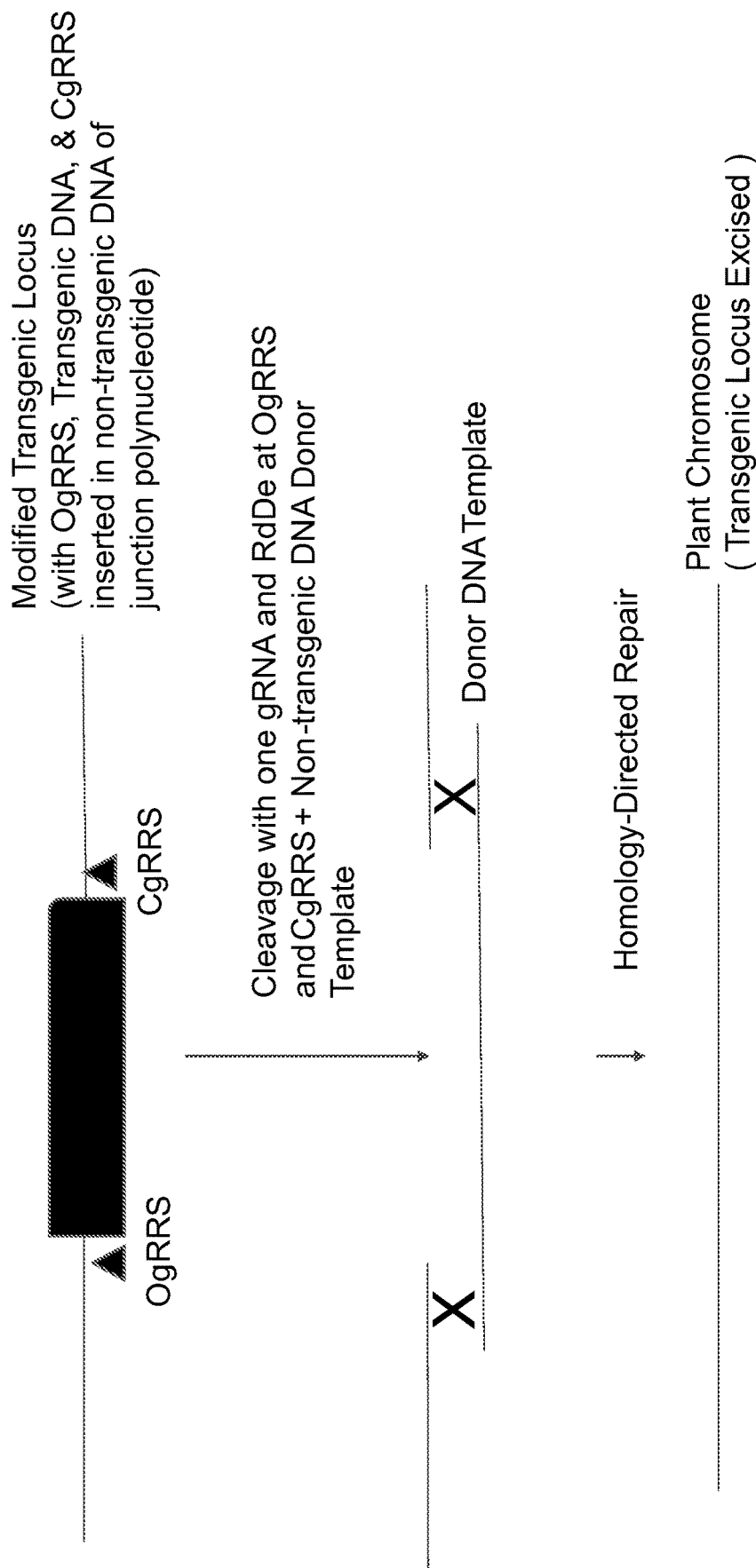

FIG. 3A, B, C. FIG. 3A shows a schematic diagram of a non-limiting example of: (i) an untransformed plant chromosome containing non-transgenic DNA which includes the originator guide RNA recognition site (OgRRS) (top); (ii) the original transgenic locus with the OgRRS in the non-transgenic DNA of the $1^{st}$ junction polynucleotide (middle); and (iii) the modified transgenic locus with a cognate guide RNA inserted into the non-transgenic DNA of the $2^{nd}$ junction polynucleotide (bottom). FIG. 3B shows a schematic diagram of a non-limiting example of a process where a modified transgenic locus with a cognate guide RNA inserted into the non-transgenic DNA of the $2^{nd}$ junction polynucleotide (top) is subjected to cleavage at the OgRRS and CgRRS with one guide RNA (gRNA) that hybridizes to gRNA hybridization site in both the OgRRS and the CgRRS and an RNA dependent DNA endonuclease (RdDe) that recognizes and cleaves the gRNA/OgRRS and the gRNA/CgRRS complex followed by non-homologous end joining processes to provide a plant chromosome where the transgenic locus is excised. FIG. 3C shows a schematic diagram of a non-limiting example of a process where a modified transgenic locus with a cognate guide RNA inserted into the non-transgenic DNA of the $2^{nd}$ junction polynucleotide (top) is subjected to cleavage at the OgRRS and CgRRS with one guide RNA (gRNA) that hybridizes to the gRNA hybridization site in both the OgRRS and the CgRRS and an RNA dependent DNA endonuclease (RdDe) that recognizes and cleaves the gRNA/OgRRS and the gRNA/CgRRS complex in the presence of a donor DNA template. In FIG. 3C, cleavage of the modified transgenic locus in the presence of the donor DNA template which has homology to non-transgenic DNA but lacks the OgRRS in the $1^{st}$ and $2^{nd}$ junction polynucleotides followed by homology-directed repair processes to provide a plant chromosome where the transgenic locus is excised and non-transgenic DNA present in the untransformed plant chromosome is at least partially restored.

DETAILED DESCRIPTION

Unless otherwise stated, nucleic acid sequences in the text of this specification are given, when read from left to right, in the 5' to 3' direction. Nucleic acid sequences may be provided as DNA or as RNA, as specified; disclosure of one necessarily defines the other, as well as necessarily defines the exact complements, as is known to one of ordinary skill in the art.

Where a term is provided in the singular, the inventors also contemplate embodiments described by the plural of that term.

The term "about" as used herein means a value or range of values which would be understood as an equivalent of a stated value and can be greater or lesser than the value or range of values stated by 10 percent. Each value or range of values preceded by the term "about" is also intended to encompass the embodiment of the stated absolute value or range of values.

The phrase "allelic variant" as used herein refers to a polynucleotide or polypeptide sequence variant that occurs in a different strain, variety, or isolate of a given organism.

The term "and/or" where used herein is to be taken as specific disclosure of each of the two specified features or components with or without the other. Thus, the term and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

As used herein, the phrase "approved transgenic locus" is a genetically modified plant event which has been authorized, approved, and/or de-regulated for any one of field testing, cultivation, human consumption, animal consumption, and/or import by a governmental body. Illustrative and non-limiting examples of governmental bodies which provide such approvals include the Ministry of Agriculture of Argentina, Food Standards Australia New Zealand, National Biosafety Technical Committee (CTNBio) of Brazil, Canadian Food Inspection Agency, China Ministry of Agriculture Biosafety Network, European Food Safety Authority, US Department of Agriculture, US Department of Environmental Protection, and US Food and Drug Administration.

The term "backcross", as used herein, refers to crossing an F1 plant or plants with one of the original parents. A backcross is used to maintain or establish the identity of one parent (species) and to incorporate a particular trait from a second parent (species). The term "backcross generation", as used herein, refers to the offspring of a backcross.

As used herein, the phrase "biological sample" refers to either intact or non-intact (e.g., milled seed or plant tissue, chopped plant tissue, lyophilized tissue) plant tissue. It may also be an extract comprising intact or non-intact seed or plant tissue. The biological sample can comprise flour, meal, syrup, oil, starch, and cereals manufactured in whole or in part to contain crop plant by-products. In certain embodiments, the biological sample is "non-regenerable" (i.e., incapable of being regenerated into a plant or plant part). In certain embodiments, the biological sample refers to a homogenate, an extract, or any fraction thereof containing genomic DNA of the organism from which the biological sample was obtained, wherein the biological sample does not comprise living cells.

As used herein, the terms "correspond," "corresponding," and the like, when used in the context of an nucleotide position, mutation, and/or substitution in any given polynucleotide (e.g., an allelic variant of SEQ ID NO: 1) with respect to the reference polynucleotide sequence (e.g., SEQ ID NO: 1) all refer to the position of the polynucleotide residue in the given sequence that has identity to the residue in the reference nucleotide sequence when the given polynucleotide is aligned to the reference polynucleotide sequence using a pairwise alignment algorithm (e.g., CLUSTAL O 1.2.4 with default parameters).

As used herein, the terms "Cpf1" and "Cas12a" are used interchangeably to refer to the same RNA dependent DNA endonuclease (RdDe). A Cas12a protein provided herein includes the protein of SEQ ID NO: 18.

The term "crossing" as used herein refers to the fertilization of female plants (or gametes) by male plants (or gametes). The term "gamete" refers to the haploid reproductive cell (egg or pollen) produced in plants by meiosis from a gametophyte and involved in sexual reproduction, during which two gametes of opposite sex fuse to form a diploid zygote. The term generally includes reference to a pollen (including the sperm cell) and an ovule (including the ovum). When referring to crossing in the context of achieving the introgression of a genomic region or segment, the skilled person will understand that in order to achieve the introgression of only a part of a chromosome of one plant into the chromosome of another plant, random portions of the genomes of both parental lines recombine during the cross due to the occurrence of crossing-over events in the production of the gametes in the parent lines. Therefore, the genomes of both parents must be combined in a single cell by a cross, where after the production of gametes from the cell and their fusion in fertilization will result in an introgression event.

As used herein, the phrases "DNA junction polynucleotide" and "junction polynucleotide" refers to a polynucleotide of about 18 to about 500 base pairs in length comprised of both endogenous chromosomal DNA of the plant genome and heterologous transgenic DNA which is inserted in the plant genome. A junction polynucleotide can thus comprise about 8, 10, 20, 50, 100, 200, 250, 500, or 1000 base pairs of endogenous chromosomal DNA of the plant genome and about 8, 10, 20, 50, 100, 200, 250, 500, or 1000 base pairs of heterologous transgenic DNA which span the one end of the transgene insertion site in the plant chromosomal DNA. Transgene insertion sites in chromosomes will typically contain both a 5' junction polynucleotide and a 3' junction polynucleotide. In embodiments set forth herein in SEQ ID NO: 1, the 5' junction polynucleotide is located at the 5' end of the sequence and the 3' junction polynucleotide is located at the 3' end of the sequence. In a non-limiting and illustrative example, a 5' junction polynucleotide of a transgenic locus is telomere proximal in a chromosome arm and the 3' junction polynucleotide of the transgenic locus is centromere proximal in the same chromosome arm. In another non-limiting and illustrative example, a 5' junction polynucleotide of a transgenic locus is centromere proximal in a chromosome arm and the 3' junction polynucleotide of the transgenic locus is telomere proximal in the same chromosome arm. The junction polynucleotide which is telomere proximal and the junction polynucleotide which is centromere proximal can be determined by comparing non-transgenic genomic sequence of a sequenced non-transgenic plant genome to the non-transgenic DNA in the junction polynucleotides.

The term "donor," as used herein in the context of a plant, refers to the plant or plant line from which the trait, transgenic event, or genomic segment originates, wherein the donor can have the trait, introgression, or genomic segment in either a heterozygous or homozygous state.

As used herein, the term "DAS59122-7" is used to refer to any of a transgenic maize locus, transgenic maize plants and parts thereof including seed set forth in U.S. Pat. No. 7,956,246, which is incorporated herein by reference in its entirety. Representative DAS59122-7 transgenic maize seed have been deposited with American Type Culture Collection (ATCC, Manassas, Va. 20110-2209 USA) under Accession No. PTA-11384. DAS59122-7 transgenic loci include loci having the sequence of SEQ ID NO:1, the sequence of the DAS59122-7 locus in the deposited seed of Accession No. PTA-11384 and any progeny thereof, as well as allelic variants and other variants of SEQ ID NO:1

As used herein, the terms "excise" and "delete," when used in the context of a DNA molecule, are used interchangeably to refer to the removal of a given DNA segment or element (e.g., transgene element or transgenic locus or portion thereof) of the DNA molecule.

As used herein, the phrase "elite crop plant" refers to a plant which has undergone breeding to provide one or more trait improvements. Elite crop plant lines include plants which are an essentially homozygous, e.g., inbred or doubled haploid. Elite crop plants can include inbred lines used as is or used as pollen donors or pollen recipients in hybrid seed production (e.g., used to produce F1 plants). Elite crop plants can include inbred lines which are selfed to produce non-hybrid cultivars or varieties or to produce (e.g., bulk up) pollen donor or recipient lines for hybrid seed production. Elite crop plants can include hybrid F1 progeny of a cross between two distinct elite inbred or doubled haploid plant lines.

As used herein, an "event," "a transgenic event," "a transgenic locus" and related phrases refer to an insertion of one or more transgenes at a unique site in the genome of a plant as well as to DNA fragments, plant cells, plants, and plant parts (e.g., seeds) comprising genomic DNA containing the transgene insertion. Such events typically comprise both a 5' and a 3' DNA junction polynucleotide and confer one or more useful traits including herbicide tolerance, insect resistance, male sterility, and the like.

As used herein, the phrases "endogenous sequence," "endogenous gene," "endogenous DNA," "endogenous polynucleotide," and the like refer to the native form of a polynucleotide, gene or polypeptide in its natural location in the organism or in the genome of an organism.

The terms "exogenous" and "heterologous" as are used synonymously herein to refer to any polynucleotide (e.g., DNA molecule) that has been inserted into a new location in the genome of a plant. Non-limiting examples of an exogenous or heterologous DNA molecule include a synthetic DNA molecule, a non-naturally occurring DNA molecule, a DNA molecule found in another species, a DNA molecule found in a different location in the same species, and/or a DNA molecule found in the same strain or isolate of a species, where the DNA molecule has been inserted into a new location in the genome of a plant.

As used herein, the term "F1" refers to any offspring of a cross between two genetically unlike individuals.

The term "gene," as used herein, refers to a hereditary unit consisting of a sequence of DNA that occupies a specific location on a chromosome and that contains the genetic instruction for a particular characteristics or trait in an organism. The term "gene" thus includes a nucleic acid (for example, DNA or RNA) sequence that comprises coding sequences necessary for the production of an RNA, or a polypeptide or its precursor. A functional polypeptide can be encoded by a full length coding sequence or by any portion of the coding sequence as long as the desired activity or functional properties (e.g., enzymatic activity, pesticidal activity, ligand binding, and/or signal transduction) of the RNA or polypeptide are retained.

The term "identifying," as used herein with respect to a plant, refers to a process of establishing the identity or distinguishing character of a plant, including exhibiting a certain trait, containing one or more transgenes, and/or containing one or more molecular markers.

As used herein, the term "INIR4" is used to refer either individually collectively to items that include any or all of the DAS59122-7 transgenic maize loci which have been modified as disclosed herein, modified DAS59122-7 transgenic maize plants and parts thereof including seed, and DNA obtained therefrom.

The term "isolated" as used herein means having been removed from its natural environment.

As used herein, the terms "include," "includes," and "including" are to be construed as at least having the features to which they refer while not excluding any additional unspecified features.

As used herein, the phrase "introduced transgene" is a transgene not present in the original transgenic locus in the genome of an initial transgenic event or in the genome of a progeny line obtained from the initial transgenic event. Examples of introduced transgenes include exogenous transgenes which are inserted in a resident original transgenic locus.

As used herein, the terms "introgression", "introgressed" and "introgressing" refer to both a natural and artificial process, and the resulting plants, whereby traits, genes or DNA sequences of one species, variety or cultivar are moved into the genome of another species, variety or cultivar, by crossing those species. The process may optionally be completed by backcrossing to the recurrent parent. Examples of introgression include entry or introduction of a gene, a transgene, a regulatory element, a marker, a trait, a trait locus, or a chromosomal segment from the genome of one plant into the genome of another plant.

The phrase "marker-assisted selection", as used herein, refers to the diagnostic process of identifying, optionally followed by selecting a plant from a group of plants using the presence of a molecular marker as the diagnostic characteristic or selection criterion. The process usually involves detecting the presence of a certain nucleic acid sequence or polymorphism in the genome of a plant.

The phrase "molecular marker", as used herein, refers to an indicator that is used in methods for visualizing differences in characteristics of nucleic acid sequences. Examples of such indicators are restriction fragment length polymorphism (RFLP) markers, amplified fragment length polymorphism (AFLP) markers, single nucleotide polymorphisms (SNPs), microsatellite markers (e.g. SSRs), sequence-characterized amplified region (SCAR) markers, Next Generation Sequencing (NGS) of a molecular marker, cleaved amplified polymorphic sequence (CAPS) markers or isozyme markers or combinations of the markers described herein which defines a specific genetic and chromosomal location.

As used herein the terms "native" or "natural" define a condition found in nature. A "native DNA sequence" is a DNA sequence present in nature that was produced by natural means or traditional breeding techniques but not generated by genetic engineering (e.g., using molecular biology/transformation techniques).

The term "offspring", as used herein, refers to any progeny generation resulting from crossing, selfing, or other propagation technique.

The phrase "operably linked" refers to a juxtaposition wherein the components so described are in a relationship permitting them to function in their intended manner. For instance, a promoter is operably linked to a coding sequence if the promoter affects its transcription or expression. When the phrase "operably linked" is used in the context of a PAM site and a guide RNA hybridization site, it refers to a PAM site which permits cleavage of at least one strand of DNA in a polynucleotide with an RNA dependent DNA endonuclease or RNA dependent DNA nickase which recognize the PAM site when a guide RNA complementary to guide RNA hybridization site sequences adjacent to the PAM site is present. A OgRRS and its CgRRS are operably linked to junction polynucleotides when they can be recognized by a gRNA and an RdDe to provide for excision of the transgenic locus or portion thereof flanked by the junction polynucleotides.

As used herein, the term "plant" includes a whole plant and any descendant, cell, tissue, or part of a plant. The term "plant parts" include any part(s) of a plant, including, for example and without limitation: seed (including mature seed and immature seed); a plant cutting; a plant cell; a plant cell culture; or a plant organ (e.g., pollen, embryos, flowers, fruits, shoots, leaves, roots, stems, and explants). A plant tissue or plant organ may be a seed, protoplast, callus, or any other group of plant cells that is organized into a structural or functional unit. A plant cell or tissue culture may be capable of regenerating a plant having the physiological and morphological characteristics of the plant from which the cell or tissue was obtained, and of regenerating a plant having substantially the same genotype as the plant. Regenerable cells in a plant cell or tissue culture may be embryos, protoplasts, meristematic cells, callus, pollen, leaves, anthers, roots, root tips, silk, flowers, kernels, ears, cobs, husks, or stalks. In contrast, some plant cells are not capable of being regenerated to produce plants and are referred to herein as "non-regenerable" plant cells.

The term "purified," as used herein defines an isolation of a molecule or compound in a form that is substantially free of contaminants normally associated with the molecule or compound in a native or natural environment and means having been increased in purity as a result of being separated from other components of the original composition. The term "purified nucleic acid" is used herein to describe a nucleic acid sequence which has been separated from other compounds including, but not limited to polypeptides, lipids and carbohydrates.

The term "recipient", as used herein, refers to the plant or plant line receiving the trait, transgenic event or genomic segment from a donor, and which recipient may or may not have the have trait, transgenic event or genomic segment itself either in a heterozygous or homozygous state.

As used herein the term "recurrent parent" or "recurrent plant" describes an elite line that is the recipient plant line in a cross and which will be used as the parent line for successive backcrosses to produce the final desired line.

As used herein the term "recurrent parent percentage" relates to the percentage that a backcross progeny plant is identical to the recurrent parent plant used in the backcross. The percent identity to the recurrent parent can be determined experimentally by measuring genetic markers such as SNPs and/or RFLPs or can be calculated theoretically based on a mathematical formula.

The terms "selfed," "selfing," and "self," as used herein, refer to any process used to obtain progeny from the same plant or plant line as well as to plants resulting from the process. As used herein, the terms thus include any fertilization process wherein both the ovule and pollen are from the same plant or plant line and plants resulting therefrom. Typically, the terms refer to self-pollination processes and progeny plants resulting from self-pollination.

The term "selecting", as used herein, refers to a process of picking out a certain individual plant from a group of individuals, usually based on a certain identity, trait, characteristic, and/or molecular marker of that individual.

As used herein, the phrase "originator guide RNA recognition site" or the acronym "OgRRS" refers to an endogenous DNA polynucleotide comprising a protospacer adjacent motif (PAM) site operably linked to a guide RNA hybridization site. In certain embodiments, an OgRRS can be located in an untransformed plant chromosome or in non-transgenic DNA of a DNA junction polynucleotide of both an original transgenic locus and a modified transgenic locus. In certain embodiments, an OgRRS can be located in transgenic DNA of a DNA junction polynucleotide of both an original transgenic locus and a modified transgenic locus. In certain embodiments, an OgRRS can be located in both transgenic DNA and non-transgenic DNA of a DNA junction polynucleotide of both an original transgenic locus and a modified transgenic locus (i.e., can span transgenic and non-transgenic DNA in a DNA junction polynucleotide).

As used herein the phrase "cognate guide RNA recognition site" or the acronym "CgRRS" refer to a DNA polynucleotide comprising a PAM site operably linked to a guide RNA hybridization site, where the CgRRS is absent from transgenic plant genomes comprising a first original transgenic locus that is unmodified and where the CgRRS and its corresponding OgRRS can hybridize to a single gRNA. A CgRRS can be located in transgenic DNA of a DNA junction polynucleotide of a modified transgenic locus, in transgenic DNA of a DNA junction polynucleotide of a modified transgenic locus, or in both transgenic and non-transgenic DNA of a modified transgenic locus (i.e., can span transgenic and non-transgenic DNA in a DNA junction polynucleotide).

As used herein, the phrase "a transgenic locus excision site" refers to the DNA which remains in the genome of a plant or in a DNA molecule (e.g., an isolated or purified DNA molecule) wherein a segment comprising, consisting essentially of, or consisting of a transgenic locus has been deleted. In a non-limiting and illustrative example, a transgenic locus excision site can thus comprise a contiguous segment of DNA comprising at least 10 base pairs of DNA that is telomere proximal to the deleted transgenic locus or to the deleted segment of the transgenic locus and at least 10 base pairs of DNA that is centromere proximal to the deleted transgenic locus or to the deleted segment of the transgenic locus.

As used herein, the phrase "transgene element" refers to a segment of DNA comprising, consisting essentially of, or consisting of a promoter, a 5' UTR, an intron, a coding region, a 3'UTR, or a polyadenylation signal. Polyadenylation signals include transgene elements referred to as "terminators" (e.g., NOS, pinII, rbcs, Hsp17, TubA).

To the extent to which any of the preceding definitions is inconsistent with definitions provided in any patent or non-patent reference incorporated herein by reference, any patent or non-patent reference cited herein, or in any patent or non-patent reference found elsewhere, it is understood that the preceding definition will be used herein.

Various sequences set forth in the sequence listing are described in the following table.

TABLE 1

Description of sequences.

| SEQ ID NO | Description |
| --- | --- |
| 1 | DAS59122-7 Complete Transgenic Locus comprising 5' flanking plant genomic DNA, 5' junction, cry34Ab1 expression cassette, cry35Ab1 expression cassette, 3' junction, and 3' flanking plant genomic DNA. The 5' flanking plant genomic DNA comprises nucleotides 1-2593, the transgenic insert spans nucleotides 2594-9936, and the 3' flanking plant genomic DNA comprises nucleotides 9937-11922. |
| 2 | INIR4-1 (with gRNA-1 Cut resulting in a deletion of nucleotides in a DAS59122-7 5' junction polynucleotide sequence) |
| 3 | INIR4-2 (Insertion of 27 bp CgRRS with gRNA-2 cut with SEQ ID NO: 24 donor DNA template) |
| 4 | gRNA-1 coding |
| 5 | gRNA-2 coding |
| 6 | gRNA-3 coding |
| 7 | OgRRS |
| 8 | CgRRS + Flanking DNA (G1 Insert) |
| 9 | CgRRS + Flanking DNA (G2 Insert) |
| 10 | CgRRS + Flanking DNA (G3 and G4 Insert) |
| 11 | DAS59122-7 CgRRS DNA donor template sequence containing the SEQ ID NO: 8 CgRRS |
| 12 | DAS59122-7 5' target insertion site |
| 13 | DAS59122-7 -gRNA spacer coding sequence that targets CgRRS of SEQ ID NO: 8, 9, 10 and OgRRS of SEQ ID NO: 7 |
| 14 | DAS59122-7 5' primer |
| 15 | DAS59122-7 3' primer |
| 16 | DAS59122-7 CgRRS and flank PCR amplicon from SEQ ID NO: 17 template using SEQ ID NO: 14 and 15 primers |
| 17 | INIR4-3 (Insertion of 27 bp CgRRS with gRNA-1 cut and SEQ ID NO: 11 donor DNA template) |
| 18 | (Cas 12a Nuclease ) (>sp|U2UMQ6|CS12A_ACISB CRISPR-associated endonuclease Cas12a OS = *Acidaminococcus* sp. (strain BV3L6) OX = 1111120 GN = cas12a PE = 1 SV = 1) |
| 19 | DAS59122-7 transgenic locus 5' Junction Polynucleotide |
| 20 | DAS59122-7 transgenic locus 5' plant genomic flanking |
| 21 | DAS59122-7 transgenic locus 3' Junction Polynucleotide |
| 22 | DAS59122-7 transgenic locus 3' plant genomic flanking |
| 23 | INIR4-4 (with gRNA-2 cut resulting in a deletion of nucleotides in a DAS59122-7 5' junction polynucleotide sequence) |
| 24 | DAS59122-7 CgRRS DNA donor template for generating INIR4-2 containing the SEQ ID NO: 9 CgRRS |

TABLE 1-continued

Description of sequences.

| SEQ ID NO | Description |
|---|---|
| 25 | gRNA-4 coding |
| 26 | INIR4-5 (gRNA-3 and gRNA-4 cuts resulting in a deletion of nucleotides in a DAS59122-7 5' junction polynucleotide sequence) |
| 27 | INIR4-6 (Insertion of 27 bp CgRRS with gRNA-3 and gRNA-4 cuts with SEQ ID NO: 28 donor DNA template) |
| 28 | DAS59122-7 CgRRS DNA donor template for generating INIR4-6 containing the SEQ ID NO: 10 CgRRS |

Genome editing molecules can permit introduction of targeted genetic change conferring desirable traits in a variety of crop plants (Zhang et al. Genome Biol. 2018; 19: 210; Schindele et al. FEBS Lett. 2018; 592(12):1954). Desirable traits introduced into crop plants such as maize and soybean include herbicide tolerance, improved food and/or feed characteristics, male-sterility, and drought stress tolerance. Nonetheless, full realization of the potential of genome editing methods for crop improvement will entail efficient incorporation of the targeted genetic changes in germplasm of different elite crop plants adapted for distinct growing conditions. Such elite crop plants will also desirably comprise useful transgenic loci which confer various traits including herbicide tolerance, pest resistance (e.g.; insect, nematode, fungal disease, and bacterial disease resistance), conditional male sterility systems for hybrid seed production, abiotic stress tolerance (e.g., drought tolerance), improved food and/or feed quality, and improved industrial use (e.g., biofuel). Provided herein are methods whereby targeted genetic changes are efficiently combined with desired subsets of transgenic loci in elite progeny plant lines (e.g., elite inbreds used for hybrid seed production or for inbred varietal production). Also provided are plant genomes containing modified transgenic loci which can be selectively excised with a single gRNA molecule. Such modified transgenic loci comprise an originator guide RNA recognition site (OgRRS) which is identified in non-transgenic DNA of a first junction polynucleotide of the transgenic locus and cognate guide RNA recognition site (CgRRS) which is introduced (e.g., by genome editing methods) into a second junction polynucleotide of the transgenic locus and which can hybridize to the same gRNA as the OgRRS, thereby permitting excision of the modified transgenic locus with a single guide RNA. An originator guide RNA recognition site (OgRRS) comprises endogenous DNA found in untransformed plants and in endogenous non-transgenic DNA of junction polynucleotides of transgenic plants containing a modified or unmodified transgenic locus. The OgRRS located in non-transgenic DNA of a first DNA junction polynucleotide is used to design a related cognate guide RNA recognition site (CgRRS) which is introduced (e.g., by genome editing methods) into the second junction polynucleotide of the transgenic locus. A CgRRS is thus present in junction polynucleotides of modified transgenic loci provided herein and is absent from endogenous DNA found in untransformed plants and absent from endogenous non-transgenic DNA found in junction sequences of transgenic plants containing an unmodified transgenic locus. Also provided are unique transgenic locus excision sites created by excision of such modified transgenic loci, DNA molecules comprising the modified transgenic loci, unique transgenic locus excision sites and/or plants comprising the same, biological samples containing the DNA, nucleic acid markers adapted for detecting the DNA molecules, and related methods of identifying the elite crop plants comprising unique transgenic locus excision sites.

Also provided herein are methods whereby targeted genetic changes are efficiently combined with desired subsets of transgenic loci in elite progeny plant lines (e.g., elite inbreds used for hybrid seed production or for inbred varietal production). Examples of such methods include those illustrated in FIG. 2. In certain embodiments, INIR4 transgenic loci provided here are characterized by polynucleotide sequences that can facilitate as necessary the removal of the INIR4 transgenic loci from the genome. Useful applications of such INIR4 transgenic loci and related methods of making include targeted excision of a INIR4 transgenic locus or portion thereof in certain breeding lines to facilitate recovery of germplasm with subsets of transgenic traits tailored for specific geographic locations and/or grower preferences. Other useful applications of such INIR4 transgenic loci and related methods of making include removal of transgenic traits from certain breeding lines when it is desirable to replace the trait in the breeding line without disrupting other transgenic loci and/or non-transgenic loci. In certain embodiments, maize genomes containing INIR4 transgenic loci or portions thereof which can be selectively excised with one or more gRNA molecules and RdDe (RNA dependent DNA endonucleases) which form gRNA/target DNA complexes. Such selectively excisable INIR4 transgenic loci can comprise an originator guide RNA recognition site (OgRRS) which is identified in non-transgenic DNA, transgenic DNA, or a combination thereof in of a first junction polynucleotide of the transgenic locus and cognate guide RNA recognition site (CgRRS) which is introduced (e.g., by genome editing methods) into a second junction polynucleotide of the transgenic locus and which can hybridize to the same gRNA as the OgRRS, thereby permitting excision of the modified transgenic locus or portions thereof with a single guide RNA (e.g., as shown in FIGS. 3A and B). In certain embodiments, an originator guide RNA recognition site (OgRRS) comprises endogenous DNA found in untransformed plants and in endogenous non-transgenic DNA of junction polynucleotides of transgenic plants containing a modified or unmodified transgenic locus. In certain embodiments, an originator guide RNA recognition site (OgRRS) comprises exogenous transgenic DNA of junction polynucleotides of transgenic plants containing a modified or unmodified transgenic locus. The OgRRS located in non-transgenic DNA transgenic DNA, or a combination thereof in of a first DNA junction polynucleotide is used to design a related cognate guide RNA recognition site (CgRRS) which is introduced (e.g., by genome editing methods) into the second junction polynucleotide of the transgenic locus. A CgRRS is thus present in junction polynucleotides of modified transgenic loci provided herein and is absent from endogenous DNA found in untransformed plants and absent from junction sequences of transgenic plants containing an unmodified transgenic locus. A CgRRS is also absent from a combination of non-transgenic and transgenic DNA found in junction sequences of transgenic plants containing an unmodified transgenic locus. Examples of OgRRS polynucleotide sequences in or near a 3' junction polynucleotide in an DAS59122-7 transgenic locus include SEQ ID NO: 7. OgRRS polynucleotide sequences located in a first junction polynucleotide can be introduced into the second junction polynucleotide using donor DNA templates as described herein. A donor DNA template for introducing the SEQ ID NO: 7 OgRRS into the 5' junction polynucleotide of an DAS59122-7 locus includes the donor DNA template of SEQ ID NO: 11 which comprises the SEQ ID NO: 8 CgRRS. Similar donor DNA templates comprising the SEQ ID NO: 9 or SEQ ID NO: 10 CgRRS elements and similar homology arms that target the DAS59122-7 5' junction polynucleotide target sequence (e.g. SEQ ID NO: 12) can be used to obtain INIR4 transgenic loci comprising the SEQ ID NO: 9 or SEQ ID NO: 10 CgRRS elements. Double stranded breaks in a 5' junction polynucleotide of SEQ ID NO: 1 can be introduced with gRNAs encoded by SEQ ID NO: 4, 5, and/or 6 and a Cas12a nuclease. Integration of the SEQ ID NO: 24 or 28 donor DNA template into the 5' junction polynucleotide of an DAS59122-7 locus at the double stranded breaks introduced by the gRNAs encoded by SEQ ID NO: 4, 5, and/or 6 and a Cas12a nuclease can provide an INIR4 locus comprising the CgRRS sequence set forth in SEQ ID NO: 9, or 10. Double stranded breaks in a 5' junction polynucleotide of SEQ ID NO: 1 can be introduced with gRNAs encoded by SEQ ID NO: 4, 5, and/or 6. Another donor DNA template adapted for insertion of the OgRRS of SEQ ID NO: 7 in a 5' junction polynucleotide of a DAS59122-7 transgenic locus can comprise SEQ ID NO: 24 or 28. Double stranded breaks in a 5' junction polynucleotide of SEQ ID NO: 1 can be introduced with gRNAs encoded by SEQ ID NO: 4 and a Cas12a nuclease. A donor DNA template of SEQ ID NO: 11 or the equivalent thereof having longer or shorter homology arms can be used to obtain the CgRRS insertion in the 5' junction polynucleotide that is set forth in SEQ ID NO: 16. An INIR4-3 transgenic locus containing this CgRRS insertion is set forth in SEQ ID NO: 17. An INIR4-2 transgenic locus containing the CgRRS insertion of SEQ ID NO: 9 is set forth in SEQ ID NO: 3. The INIR4-2 transgenic locus of SEQ ID NO: 3 can be obtained by using gRNA-2 (SEQ ID NO: 5) with a Cas12A nuclease and the donor DNA template of SEQ ID NO: 24. An INIR4-6 transgenic locus containing the CgRRS insertion of SEQ ID NO: 10 is set forth in SEQ ID NO: 27. The INIR4-6 transgenic locus of SEQ ID NO: 27 can be obtained by using gRNA-3 (SEQ ID NO: 6) and gRNA-4 (SEQ ID NO: 25) with a Cas12A nuclease and the donor DNA template of SEQ ID NO: 28.

Also provided are unique transgenic locus excision sites created by excision of INIR4 transgenic loci or selectively excisable INIR4 transgenic loci, DNA molecules comprising the INIR4 transgenic loci or unique fragments thereof (i.e., fragments of an INIR4 locus which are not found in an DAS59122-7 transgenic locus), INIR4 plants comprising the same, biological samples containing the DNA, nucleic acid markers adapted for detecting the DNA molecules, and related methods of identifying maizew plants comprising unique INIR4 transgenic locus excision sites and unique fragments of a INIR4 transgenic locus. DNA molecules comprising unique fragments of an INIR4 transgenic locus are diagnostic for the presence of an INIR4 transgenic locus or fragments thereof in a maize plant, maize cell, maize seed, products obtained therefrom (e.g., seed meal or stover), and biological samples. DNA molecules comprising unique fragments of an INIR4 transgenic locus include DNA molecules comprising Methods provided herein can be used to excise any transgenic locus where the first and second junction sequences comprising the endogenous non-transgenic genomic DNA and the heterologous transgenic DNA which are joined at the site of transgene insertion in the plant genome are known or have been determined. In certain embodiments provided herein, transgenic loci can be removed from crop plant lines to obtain crop plant lines with tailored combinations of transgenic loci and optionally targeted genetic changes. Such first and second junction sequences are readily identified in new transgenic events by inverse PCR techniques using primers which are complementary the inserted transgenic sequences. In certain embodiments, the first and second junction sequences of transgenic loci are published. An example of a transgenic locus which can be improved and used in the methods provided herein is the maize DAS59122-7 transgenic locus. The maize DAS59122-7 transgenic locus and its transgenic junction sequences are also depicted in FIG. 1. Maize plants comprising the DAS59122-7 transgenic locus and seed thereof have been cultivated, been placed in commerce, and have been described in a variety of publications by various governmental bodies. Databases which have compiled descriptions of the DAS59122-7 transgenic locus include the International Service for the Acquisition of Agri-biotech Applications (ISAAA) database (available on the world wide web internet site "isaaa.org/gmapprovaldatabase/event"), the GenBit LLC database (available on the world wide web internet site "genbitgroup.com/en/gmo/gmodatabase"), and the Biosafety Clearing-House (BCH) database (available on the http internet site "bch.cbd.int/database/organisms").

Sequences of the junction polynucleotides as well as the transgenic insert(s) of the DAS59122-7 transgenic locus which can be improved by the methods provided herein are set forth or otherwise provided in SEQ ID NO: 1, U.S. Pat. No. 7,956,246, the sequence of the DAS59122-7 locus in the deposited seed of ATCC accession No. PTA-11384, and elsewhere in this disclosure. In certain embodiments provided herein, the DAS59122-7 transgenic locus set forth in SEQ ID NO: 1 or present in the deposited seed of ATCC accession No. PTA-11384 is referred to as an "original DAS59122-7 transgenic locus." Allelic or other variants of the sequence set forth SEQ ID NO: 1, the patent references set forth therein and incorporated herein by reference in their entireties, and elsewhere in this disclosure which may be present in certain variant DAS59122-7 transgenic plant loci (e.g., progeny of deposited seed of accession No. PTA-11384 which contain allelic variants of SEQ ID NO:1 or progeny originating from transgenic plant cells comprising the original DAS59122-7 transgenic set forth in U.S. Pat. No. 7,956,246) can also be improved by identifying sequences in the variants that correspond to the SEQ ID NO: 1 by performing a pairwise alignment (e.g., using CLUSTAL O 1.2.4 with default parameters) and making corresponding changes in the allelic or other variant sequences. Such allelic or other variant sequences include sequences having at least 85%, 90%, 95%, 98%, or 99% sequence identity across the entire length or at least 20, 40, 100, 500, 1,000, 2,000, 4,000, 8,000, 10,000, or 12,282 nucleotides of SEQ ID NO: 1. Also provided are plants, plant parts including seeds, genomic DNA, and/or DNA obtained from INIR4 plants which comprise one or more modifications (e.g., via insertion of a CgRRS in a junction polynucleotide sequence) which provide for selective excision of the INIR4 transgenic locus or a portion thereof. Also provided herein are methods of detecting plants, genomic DNA, and/or DNA obtained from plants comprising a INIR4 transgenic locus which contains one or more of a CgRRS, deletions of selectable marker genes, deletions of non-essential DNA, and/or a transgenic locus excision site. A first junction polynucleotide of a DAS59122-7 transgenic locus can comprise either one of the junction polynucleotides found at the 5' end or the 3' end of any one of the sequences set forth in SEQ ID NO: 1, allelic variants thereof, or other variants thereof. An OgRRS can be found within non-transgenic DNA, transgenic DNA, or a combination thereof in either one of the junction polynucleotides of any one of SEQ ID NO: 1, allelic variants thereof, or other variants thereof. A second junction polynucleotide of a transgenic locus can comprise either one of the junction polynucleotides found at the 5' or 3' end of any one of the sequences set forth in SEQ ID NO: 1, allelic variants thereof, or other variants thereof. A CgRRS can be introduced within transgenic, non-transgenic DNA, or a combination thereof of either one of the junction polynucleotides of any one of SEQ ID NO: 1, allelic variants thereof, or other variants thereof to obtain an INIR4 transgenic locus. In certain embodiments, the OgRRS is found in non-transgenic DNA or transgenic DNA of the 5' junction polynucleotide of a transgenic locus of any one of SEQ ID NO: 1, allelic variants thereof, or other variants thereof and the corresponding CgRRS is introduced into the transgenic DNA, non-transgenic DNA, or a combination thereof in the 3' junction polynucleotide of the DAS59122-7 transgenic locus of SEQ ID NO: 1, allelic variants thereof, or other variants thereof to obtain an INIR4 transgenic locus. In other embodiments, the OgRRS is found in non-transgenic DNA or transgenic DNA of the 3' junction polynucleotide of the DAS59122-7 transgenic locus of any one of SEQ ID NO: 1, allelic variants thereof, or other variants thereof and the corresponding CgRRS is introduced into the transgenic DNA, non-transgenic DNA, or a combination thereof in the 5' junction polynucleotide of the transgenic locus of SEQ ID NO: 1, allelic variants thereof, or other variants thereof to obtain an INIR4 transgenic locus.

Also provided herein are allelic variants of any of the INIR4 transgenic loci and DNA molecules provided herein. In certain embodiments, such allelic variants of INIR4 transgenic loci include sequences having at least 85%, 90%, 95%, 98%, or 99% sequence identity across the entire length or at least 20, 40, 100, 500, 1,000, 2,000, 4,000, or nucleotides of SEQ ID NO: 2, 3, 17, 23, 26, 27, 28, 29, 30, or 31. In certain embodiments, such allelic variants of INIR4 DNA molecules include sequences having at least 85%, 90%, 95%, 98%, or 99% sequence identity across the entire length of 2, 3, 8, 9, 10, 11, 17, 23, 24, 26, 27, or 28.

In certain embodiments, the CgRRS is comprised in whole or in part of an exogenous DNA molecule that is introduced into a DNA junction polynucleotide by genome editing. In certain embodiments, the guide RNA hybridization site of the CgRRS is operably linked to a pre-existing PAM site in the transgenic DNA or non-transgenic DNA of the transgenic plant genome. In other embodiments, the guide RNA hybridization site of the CgRRS is operably linked to a new PAM site that is introduced in the DNA junction polynucleotide by genome editing. A CgRRS can be located in non-transgenic plant genomic DNA of a DNA junction polynucleotide of an INIR4 transgenic locus, in transgenic DNA of a DNA junction polynucleotide of an INIR4 transgenic locus, or can span the junction of the transgenic and non-transgenic DNA of a DNA junction polynucleotide of an INIR4 transgenic locus. An OgRRS can likewise be located in non-transgenic plant genomic DNA of a DNA junction polynucleotide of an INIR4 transgenic locus, in transgenic DNA of a DNA junction polynucleotide of an INIR4 transgenic locus, or can span the junction of the transgenic and non-transgenic DNA of a DNA junction polynucleotide of an INIR4 transgenic locus Methods provided herein can be used in a variety of breeding schemes to obtain elite crop plants comprising subsets of desired modified transgenic loci comprising an OgRRS and a CgRRS operably linked to junction polynucleotide sequences and transgenic loci excision sites where undesired transgenic loci or portions thereof have been removed (e.g., by use of the OgRRS and a CgRRS). Such methods are useful at least insofar as they allow for production of distinct useful donor plant lines each having unique sets of modified transgenic loci and, in some instances, targeted genetic changes that are tailored for distinct geographies and/or product offerings. In an illustrative and non-limiting example, a different product lines comprising transgenic loci conferring only two of three types of herbicide tolerance (e.g., glyphosate, glufosinate, and dicamba) can be obtained from a single donor line comprising three distinct transgenic loci conferring resistance to all three herbicides. In certain aspects, plants comprising the subsets of undesired transgenic loci and transgenic loci excision sites can further comprise targeted genetic changes. Such elite crop plants can be inbred plant lines or can be hybrid plant lines. In certain embodiments, at least two transgenic loci (e.g., transgenic loci including an INIR4 and another modified transgenic locus wherein an OgRRS and a CgRRS site is operably linked to a first and a second junction sequence and optionally a selectable marker gene and/or non-essential DNA are deleted) are introgressed into a desired donor line comprising elite crop plant germplasm and then subjected to genome editing molecules to recover plants comprising one of the two introgressed transgenic loci as well as a transgenic loci excision site introduced by excision of the other transgenic locus or portion thereof by the genome editing molecules. In certain embodiments, the genome editing molecules can be used to remove a transgenic locus and introduce targeted genetic changes in the crop plant genome. Introgression can be achieved by backcrossing plants comprising the transgenic loci to a recurrent parent comprising the desired elite germplasm and selecting progeny with the transgenic loci and recurrent parent germplasm. Such backcrosses can be repeated and/or supplemented by molecular assisted breeding techniques using SNP or other nucleic acid markers to select for recurrent parent germplasm until a desired recurrent parent percentage is obtained (e.g., at least about 95%, 96%, 97%, 98%, or 99% recurrent parent percentage). A non-limiting, illustrative depiction of a scheme for obtaining plants with both subsets of transgenic loci and the targeted genetic changes is shown in the FIG. 2 (bottom "Alternative" panel), where two or more of the transgenic loci ("Event" in FIG. 2) are provided in Line A and then moved into elite crop plant germplasm by introgression. In the non-limiting FIG. 2 illustration, introgression can be achieved by crossing a "Line A" comprising two or more of the modified transgenic loci to the elite germplasm and then backcrossing progeny of the cross comprising the transgenic loci to the elite germplasm as the recurrent parent) to obtain a "Universal Donor" (e.g., Line A+ in FIG. 2) comprising two or more of the modified transgenic loci. This elite germplasm containing the modified transgenic loci (e.g., "Universal Donor" of FIG. 2) can then be subjected to genome editing molecules which can excise at least one of the transgenic loci ("Event Removal" in FIG. 2) and introduce other targeted genetic changes ("GE" in FIG. 2) in the genomes of the elite crop plants containing one of the transgenic loci and a transgenic locus excision site corresponding to the removal site of one of the transgenic loci. Such selective excision of transgenic loci or portion thereof can be effected by contacting the genome of the plant comprising two transgenic loci with gene editing molecules (e.g., RdDe and gRNAs, TALENS, and/or ZFN) which recognize one transgenic loci but not another transgenic loci. Genome editing molecules that provide for selective excision of a first modified transgenic locus comprising an OgRRS and a CgRRS include a gRNA that hybridizes to the OgRRS and CgRRS of the first modified transgenic locus and an RdDe that recognizes the gRNA/OgRRS and gRNA/CgRRS complexes. Distinct plant lines with different subsets of transgenic loci and desired targeted genetic changes are thus recovered (e.g., "Line B-1," "Line B-2," and "Line B-3" in FIG. 2). In certain embodiments, it is also desirable to bulk up populations of inbred elite crop plants or their seed comprising the subset of transgenic loci and a transgenic locus excision site by selfing. In certain embodiments, inbred progeny of the selfed maize plants comprising the INIR4 transgenic loci can be used as a pollen donor or recipient for hybrid seed production. Such hybrid seed and the progeny grown therefrom can comprise a subset of desired transgenic loci and a transgenic loci excision site.

Hybrid plant lines comprising elite crop plant germplasm, at least one transgenic locus and at least one transgenic locus excision site, and in certain aspects, additional targeted genetic changes are also provided herein. Methods for production of such hybrid seed can comprise crossing elite crop plant lines where at least one of the pollen donor or recipient comprises at least the transgenic locus and a transgenic locus excision site and/or additional targeted genetic changes. In certain embodiments, the pollen donor and recipient will comprise germplasm of distinct heterotic groups and provide hybrid seed and plants exhibiting heterosis. In certain embodiments, the pollen donor and recipient can each comprise a distinct transgenic locus which confers either a distinct trait (e.g., herbicide tolerance or insect resistance), a different type of trait (e.g., tolerance to distinct herbicides or to distinct insects such as coleopteran or lepidopteran insects), or a different mode-of-action for the same trait (e.g., resistance to coleopteran insects by two distinct modes-of-action or resistance to lepidopteran insects by two distinct modes-of-action). In certain embodiments, the pollen recipient will be rendered male sterile or conditionally male sterile. Methods for inducing male sterility or conditional male sterility include emasculation (e.g., detasseling), cytoplasmic male sterility, chemical hybridizing agents or systems, a transgenes or transgene systems, and/or mutation(s) in one or more endogenous plant genes. Descriptions of various male sterility systems that can be adapted for use with the elite crop plants provided herein are described in Wan et al. Molecular Plant; 12, 3, (2019):321-342 as well as in U.S. Pat. No. 8,618,358; US 20130031674; and US 2003188347.

In certain embodiments, it will be desirable to use genome editing molecules to make modified transgenic loci by introducing a CgRRS into the transgenic loci, to excise modified transgenic loci comprising an OgRRS and a CgRRS, and/or to make targeted genetic changes in elite crop plant or other germplasm. Techniques for effecting genome editing in crop plants (e.g., maize,) include use of morphogenic factors such as Wuschel (WUS), Ovule Development Protein (ODP), and/or Babyboom (BBM) which can improve the efficiency of recovering plants with desired genome edits. In some aspects, the morphogenic factor comprises WUS1, WUS2, WUS3, WOX2A, WOX4, WOX5, WOX9, BBM2, BMN2, BMN3, and/or ODP2. In certain embodiments, compositions and methods for using WUS, BBM, and/or ODP, as well as other techniques which can be adapted for effecting genome edits in elite crop plant and other germplasm, are set forth in US 20030082813, US 20080134353, US 20090328252, US 20100100981, US 20110165679, US 20140157453, US 20140173775, and US 20170240911, which are each incorporated by reference in their entireties. In certain embodiments, the genome edits can be effected in regenerable plant parts (e.g., plant embryos) of elite crop plants by transient provision of gene editing molecules or polynucleotides encoding the same and do not necessarily require incorporating a selectable marker gene into the plant genome (e.g., US 20160208271 and US 20180273960, both incorporated herein by reference in their entireties; Svitashev et al. Nat Commun. 2016; 7:13274).

In certain embodiments, edited transgenic plant genomes, transgenic plant cells, parts, or plants containing those genomes, and DNA molecules obtained therefrom, can comprise a desired subset of transgenic loci and/or comprise at least one transgenic locus excision site. In certain embodiments, a segment comprising an INIR4 transgenic locus comprising an OgRRS in non-transgenic DNA of a 1st junction polynucleotide sequence and a CgRRS in a 2nd junction polynucleotide sequence is deleted with a gRNA and RdDe that recognize the OgRRS and the CgRRS to produce an INIR4 transgenic locus excision site. In certain embodiments, the transgenic locus excision site can comprise a contiguous segment of DNA comprising at least 10 base pairs of DNA that is telomere proximal to the deleted segment of the transgenic locus and at least 10 base pairs of DNA that is centromere proximal to the deleted segment of the transgenic locus wherein the transgenic DNA (i.e., the heterologous DNA) that has been inserted into the crop plant genome has been deleted. In certain embodiments where a segment comprising a transgenic locus has been deleted, the transgenic locus excision site can comprise a contiguous segment of DNA comprising at least 10 base pairs DNA that is telomere proximal to the deleted segment of the transgenic locus and at least 10 base pairs of DNA that is centromere proximal DNA to the deleted segment of the transgenic locus wherein the heterologous transgenic DNA and at least 1, 2, 5, 10, 20, 50, or more base pairs of endogenous DNA located in a 5' junction sequence and/or in a 3' junction sequence of the original transgenic locus that has been deleted. In such embodiments where DNA comprising the transgenic locus is deleted, a transgenic locus excision site can comprise at least 10 base pairs of DNA that is telomere proximal to the deleted segment of the transgenic locus and at least 10 base pairs of DNA that is centromere proximal to the deleted segment of the transgenic locus wherein all of the transgenic DNA is absent and either all or less than all of the endogenous DNA flanking the transgenic DNA sequences are present. In certain embodiments where a segment consisting essentially of an original transgenic locus has been deleted, the transgenic locus excision site can be a contiguous segment of at least 10 base pairs of DNA that is telomere proximal to the deleted segment of the transgenic locus and at least 10 base pairs of DNA that is centromere proximal to the deleted segment of the transgenic locus wherein less than all of the heterologous transgenic DNA that has been inserted into the crop plant genome is excised. In certain aforementioned embodiments where a segment consisting essentially of an original transgenic locus has been deleted, the transgenic locus excision site can thus contain at least 1 base pair of DNA or 1 to about 2 or 5, 8, 10, 20, or 50 base pairs of DNA comprising the telomere proximal and/or centromere proximal heterologous transgenic DNA that has been inserted into the crop plant genome. In certain embodiments where a segment consisting of an original transgenic locus has been deleted, the transgenic locus excision site can contain a contiguous segment of DNA comprising at least 10 base pairs of DNA that is telomere proximal to the deleted segment of the transgenic locus and at least 10 base pairs of DNA that is centromere proximal to the deleted segment of the transgenic locus wherein the heterologous transgenic DNA that has been inserted into the crop plant genome is deleted. In certain embodiments where DNA consisting of the transgenic locus is deleted, a transgenic locus excision site can comprise at least 10 base pairs of DNA that is telomere proximal to the deleted segment of the transgenic locus and at least 10 base pairs of DNA that is centromere proximal to the deleted segment of the transgenic locus wherein all of the heterologous transgenic DNA that has been inserted into the crop plant genome is deleted and all of the endogenous DNA flanking the heterologous sequences of the transgenic locus is present. In any of the aforementioned embodiments or in other embodiments, the continuous segment of DNA comprising the transgenic locus excision site can further comprise an insertion of 1 to about 2, 5, 10, 20, or more nucleotides between the DNA that is telomere proximal to the deleted segment of the transgenic locus and the DNA that is centromere proximal to the deleted segment of the transgenic locus. Such insertions can result either from endogenous DNA repair and/or recombination activities at the double stranded breaks introduced at the excision site and/or from deliberate insertion of an oligonucleotide. Plants, edited plant genomes, biological samples, and DNA molecules (e.g., including isolated or purified DNA molecules) comprising the INIR4 transgenic loci excision sites are provided herein.

In other embodiments, a segment comprising a INIR4 transgenic locus (e.g., a transgenic locus comprising an OgRRS in non-transgenic DNA of a $1^{st}$ junction sequence and a CgRRS in a $2^{nd}$ junction sequence) can be deleted with a gRNA and RdDe that recognize the OgRRS and the CgRRS and replaced with DNA comprising the endogenous non-transgenic plant genomic DNA present in the genome prior to transgene insertion. A non-limiting example of such replacements can be visualized in FIG. 3C, where the donor DNA template can comprise the endogenous non-transgenic plant genomic DNA present in the genome prior to transgene insertion along with sufficient homology to non-transgenic DNA on each side of the excision site to permit homology-directed repair. In certain embodiments, the endogenous non-transgenic plant genomic DNA present in the genome prior to transgene insertion can be at least partially restored. In certain embodiments, the endogenous non-transgenic plant genomic DNA present in the genome prior to transgene insertion can be essentially restored such that no more than about 5, 10, or 20 to about 50, 80, or 100 nucleotides are changed relative to the endogenous DNA at the essentially restored excision site.

In certain embodiments, edited transgenic plant genomes and transgenic plant cells, plant parts, or plants containing those edited genomes, comprising a modification of an original transgenic locus, where the modification comprises an OgRRS and a CgRRS which are operably linked to a $1^{st}$ and a $2^{nd}$ junction sequence, respectively or irrespectively, and optionally further comprise a deletion of a segment of the original transgenic locus. In certain embodiments, the modification comprises two or more separate deletions and/or there is a modification in two or more original transgenic plant loci. In certain embodiments, the deleted segment comprises, consists essentially of, or consists of a segment of non-essential DNA in the transgenic locus. Illustrative examples of non-essential DNA include but are not limited to synthetic cloning site sequences, duplications of transgene sequences; fragments of transgene sequences, and *Agrobacterium* right and/or left border sequences. In certain embodiments, the non-essential DNA is a duplication and/or fragment of a promoter sequence and/or is not the promoter sequence operably linked in the cassette to drive expression of a transgene. In certain embodiments, excision of the non-essential DNA improves a characteristic, functionality, and/or expression of a transgene of the transgenic locus or otherwise confers a recognized improvement in a transgenic plant comprising the edited transgenic plant genome. In certain embodiments, the non-essential DNA does not comprise DNA encoding a selectable marker gene. In certain embodiments of an edited transgenic plant genome, the modification comprises a deletion of the non-essential DNA and a deletion of a selectable marker gene. The modification producing the edited transgenic plant genome could occur by excising both the non-essential DNA and the selectable marker gene at the same time, e.g., in the same modification step, or the modification could occur step-wise. For example, an edited transgenic plant genome in which a selectable marker gene has previously been removed from the transgenic locus can comprise an original transgenic locus from which a non-essential DNA is further excised and vice versa. In certain embodiments, the modification comprising deletion of the non-essential DNA and deletion of the selectable marker gene comprises excising a single segment of the original transgenic locus that comprises both the non-essential DNA and the selectable marker gene. Such modification would result in one excision site in the edited transgenic genome corresponding to the deletion of both the non-essential DNA and the selectable marker gene. In certain embodiments, the modification comprising deletion of the non-essential DNA and deletion of the selectable marker gene comprises excising two or more segments of the original transgenic locus to achieve deletion of both the non-essential DNA and the selectable marker gene. Such modification would result in at least two excision sites in the edited transgenic genome corresponding to the deletion of both the non-essential DNA and the selectable marker gene. In certain embodiments of an edited transgenic plant genome, prior to excision, the segment to be deleted is flanked by operably linked protospacer adjacent motif (PAM) sites in the original or unmodified transgenic locus and/or the segment to be deleted encompasses an operably linked PAM site in the original or unmodified transgenic locus. In certain embodiments, following excision of the segment, the resulting edited transgenic plant genome comprises PAM sites flanking the deletion site in the modified transgenic locus. In certain embodiments of an edited transgenic plant genome, the modification comprises a modification of a DAS59122-7 transgenic locus.

In certain embodiments, improvements in a transgenic plant locus are obtained by introducing a new cognate guide RNA recognition site (CgRRS) which is operably linked to a DNA junction polynucleotide of the transgenic locus in the transgenic plant genome. Such CgRRS sites can be recognized by RdDe and a single suitable guide RNA directed to the CgRRS and the originator gRNA Recognition Site (OgRRS) to provide for cleavage within the junction polynucleotides which flank an INIR4 transgenic locus. In certain embodiments, the CgRRS/gRNA and OgRRS/gRNA hybridization complexes are recognized by the same class of RdDe (e.g., Class 2 type II or Class 2 type V) or by the same RdDe (e.g., both the CgRRS/gRNA and OgRRS/gRNA hybridization complexes recognized by the same Cas9 or Cas 12 RdDe). Such CgRRS and OgRRS can be recognized by RdDe and suitable guide RNAs containing crRNA sufficiently complementary to the guide RNA hybridization site DNA sequences adjacent to the PAM site of the CgRRS and the OgRRS to provide for cleavage within or near the two junction polynucleotides. Suitable guide RNAs can be in the form of a single gRNA comprising a crRNA or in the form of a crRNA/tracrRNA complex. In the case of the OgRRS site, the PAM and guide RNA hybridization site are endogenous DNA polynucleotide molecules found in the plant genome. In certain embodiments where the CgRRS is introduced into the plant genome by genome editing, gRNA hybridization site polynucleotides introduced at the CgRRS are at least 17 or 18 nucleotides in length and are complementary to the crRNA of a guide RNA. In certain embodiments, the gRNA hybridization site sequence of the OgRRS and/or the CgRRS is about 17 or 18 to about 24 nucleotides in length. The gRNA hybridization site sequence of the OgRRS and the gRNA hybridization site of the CgRRS can be of different lengths or comprise different sequences so long as there is sufficient complementarity to permit hybridization by a single gRNA and recognition by a RdDe that recognizes and cleaves DNA at the gRNA/OgRRS and gRNA/CgRRS complex. In certain embodiments, the guide RNA hybridization site of the CgRRS comprise about a 17 or 18 to about 24 nucleotide sequence which is identical to the guide RNA hybridization site of the OgRRS. In other embodiments, the guide RNA hybridization site of the CgRRS comprise about a 17 or 18 to about 24 nucleotide sequence which has one, two, three, four, or five nucleotide insertions, deletions or substitutions when compared to the guide RNA hybridization site of the OgRRS. Certain CgRRS comprising a gRNA hybridization site containing has one, two, three, four, or five nucleotide insertions, deletions or substitutions when compared to the guide RNA hybridization site of the OgRRS can undergo hybridization with a gRNA which is complementary to the OgRRS gRNA hybridization site and be cleaved by certain RdDe. Examples of mismatches between gRNAs and guide RNA hybridization sites which allow for RdDe recognition and cleavage include mismatches resulting from both nucleotide insertions and deletions in the DNA which is hybridized to the gRNA (e.g., Lin et al., doi: 10.1093/nar/gku402). In certain embodiments, an operably linked PAM site is co-introduced with the gRNA hybridization site polynucleotide at the CgRRS. In certain embodiments, the gRNA hybridization site polynucleotides are introduced at a position adjacent to a resident endogenous PAM sequence in the junction polynucleotide sequence to form a CgRRS where the gRNA hybridization site polynucleotides are operably linked to the endogenous PAM site. In certain embodiments, non-limiting features of the OgRRS, CgRRS, and/or the gRNA hybridization site polynucleotides thereof include: (i) absence of significant homology or sequence identity (e.g., less than 50% sequence identity across the entire length of the OgRRS, CgRRS, and/or the gRNA hybridization site sequence) to any other endogenous or transgenic sequences present in the transgenic plant genome or in other transgenic genomes of the maize plant being transformed and edited; (ii) absence of significant homology or sequence identity (e.g., less than 50% sequence identity across the entire length of the sequence) of a sequence of a first OgRRS and a first CgRRS to a second OgRRS and a second CgRRS which are operably linked to junction polynucleotides of a distinct transgenic locus; (iii) the presence of some sequence identity (e.g., about 25%, 40%, or 50% to about 60%, 70%, or 80%) between the OgRRS sequence and endogenous sequences present at the site where the CgRRS sequence is introduced; and/or (iv) optimization of the gRNA hybridization site polynucleotides for recognition by the RdDe and guide RNA when used in conjunction with a particular PAM sequence. In certain embodiments, the first and second OgRRS as well as the first and second CgRRS are recognized by the same class of RdDe (e.g., Class 2 type II or Class 2 type V) or by the same RdDe (e.g., Cas9 or Cas 12 RdDe). In certain embodiments, the first OgRRS site in a first junction polynucleotide and the CgRRS introduced in the second junction polynucleotide to permit excision of a first transgenic locus by a first single guide RNA and a single RdDe. Such nucleotide insertions or genome edits used to introduce CgRRS in a transgenic plant genome can be effected in the plant genome by using gene editing molecules (e.g., RdDe and guide RNAs, RNA dependent nickases and guide RNAs, Zinc Finger nucleases or nickases, or TALE nucleases or nickases) which introduce blunt double stranded breaks or staggered double stranded breaks in the DNA junction polynucleotides. In the case of DNA insertions, the genome editing molecules can also in certain embodiments further comprise a donor DNA template or other DNA template which comprises the heterologous nucleotides for insertion to form the CgRRS. Guide RNAs can be directed to the junction polynucleotides by using a pre-existing PAM site located within or adjacent to a junction polynucleotide of the transgenic locus. Non-limiting examples of such pre-existing PAM sites present in junction polynucleotides, which can be used either in conjunction with an inserted heterologous sequence to form a CgRRS or which can be used to create a double stranded break to insert or create a CgRRS, include PAM sites recognized by a Cas12a enzyme. Non-limiting examples where a CgRRS are created in a DNA sequence are illustrated in Example 2.

Transgenic loci comprising OgRRS and CgRRS in a first and a second junction polynucleotides can be excised from the genomes of transgenic plants by contacting the transgenic loci with RdDe or RNA directed nickases, and a suitable guide RNA directed to the OgRRS and CgRRS. A non-limiting example where a modified transgenic locus is excised from a plant genome by use of a gRNA and an RdDe that recognizes an OgRRS/gRNA and a CgRRS/gRNA complex and introduces dsDNA breaks in both junction polynucleotides nd repaired by NHEJ is depicted in FIG. 3B. In the depicted example set forth in FIG. 3B, the OgRRS site and the CgRRS site are absent from the plant chromosome comprising the transgene excision site that results from the process. In other embodiments provided herein where a modified transgenic locus is excised from a plant genome by use of a gRNA and an RdDe that recognizes an OgRRS/gRNA and a CgRRS/gRNA complex and repaired by NHEJ or microhomology-mediated end joining (MMEJ), the OgRRS and/or other non-transgenic sequences that were originally present prior to transgene insertion are partially or essentially restored.

In certain embodiments, edited transgenic plant genomes provided herein can lack one or more selectable and/or scoreable markers found in an original event (transgenic locus). Original DAS59122-7 transgenic loci (events), including those set forth in SEQ ID NO: 1), U.S. Pat. No. 7,956,246, the sequence of the DAS59122-7 locus in the deposited seed of accession No. PTA-11384 and progeny thereof, contain a selectable marker gene encoding a phosphinotricin acetyl transferase (PAT) protein which confers tolerance to the herbicide glufosinate. In certain embodiments provided herein, the DNA element comprising, consisting essentially of, or consisting of the PAT selectable marker gene of an DAS59122-7 transgenic locus is absent from an INIR4 transgenic locus. The PAT selectable marker cassette can be excised from an original DAS59122-7 transgenic locus by contacting the transgenic locus with one or more gene editing molecules which introduce double stranded breaks in the transgenic locus at the 5' and 3' end of the expression cassette comprising the PAT selectable marker transgene (e.g., an RdDe and guide RNAs directed to PAM sites located at the 5' and 3' end of the expression cassette comprising the PAT selectable marker transgene) and selecting for plant cells, plant parts, or plants wherein the selectable marker has been excised. In certain embodiments, the selectable or scoreable marker transgene can be inactivated. Inactivation can be achieved by modifications including insertion, deletion, and/or substitution of one or more nucleotides in a promoter element, 5' or 3' untranslated region (UTRs), intron, coding region, and/or 3' terminator and/or polyadenylation site of the selectable marker transgene. Such modifications can inactivate the selectable marker transgene by eliminating or reducing promoter activity, introducing a missense mutation, and/or introducing a pre-mature stop codon. In certain embodiments, the selectable PAT marker transgene can be replaced by an introduced transgene. In certain embodiments, an original transgenic locus that was contacted with gene editing molecules which introduce double stranded breaks in the transgenic locus at the 5' and 3' end of the expression cassette comprising the PAT selectable marker transgene can also be contacted with a suitable donor DNA template comprising an expression cassette flanked by DNA homologous to remaining DNA in the transgenic locus located 5' and 3' to the selectable marker excision site. In certain embodiments, a coding region of the PAT selectable marker transgene can be replaced with another coding region such that the replacement coding region is operably linked to the promoter and 3' terminator or polyadenylation site of the PAT selectable marker transgene.

In certain embodiments, edited transgenic plant genomes provided herein can comprise additional new introduced transgenes (e.g., expression cassettes) inserted into the transgenic locus of a given event. Introduced transgenes inserted at the transgenic locus of an event subsequent to the event's original isolation can be obtained by inducing a double stranded break at a site within an original transgenic locus (e.g., with genome editing molecules including an RdDe and suitable guide RNA(s); a suitable engineered zinc-finger nuclease; a TALEN protein and the like) and providing an exogenous transgene in a donor DNA template which can be integrated at the site of the double stranded break (e.g. by homology-directed repair (HDR) or by non-homologous end-joining (NHEJ)). In certain embodiments, an OgRRS and a CgRRS located in a $1^{st}$ junction polynucleotide and a $2^{nd}$ junction polynucleotide, respectively, can be used to delete the transgenic locus and replace it with one or more new expression cassettes. In certain embodiments, such deletions and replacements are effected by introducing dsDNA breaks in both junction polynucleotides and providing the new expression cassettes on a donor DNA template. Suitable expression cassettes for insertion include DNA molecules comprising promoters which are operably linked to DNA encoding proteins and/or RNA molecules which confer useful traits which are in turn operably linked to polyadenylation sites or terminator elements. In certain embodiments, such expression cassettes can also comprise 5' UTRs, 3' UTRs, and/or introns. Useful traits include biotic stress tolerance (e.g., insect resistance, nematode resistance, or disease resistance), abiotic stress tolerance (e.g., heat, cold, drought, and/or salt tolerance), herbicide tolerance, and quality traits (e.g., improved fatty acid compositions, protein content, starch content, and the like). Suitable expression cassettes for insertion include expression cassettes which confer insect resistance, herbicide tolerance, biofuel use, or male sterility traits contained in any of the transgenic events set forth in US Patent Application Public. Nos. 20090038026, 20130031674, 20150361446, 20170088904, 20150267221, 201662346688, and 20200190533 as well as in U.S. Pat. Nos. 6,342,660, 7,323,556, 6,040,497, 8,759, 618, 7,157,281, 6,852,915, 7,705,216, 10,316,330, 8,618, 358, 8,450,561, 8,212,113, 9,428,765, 7,897,748, 8,273,959, 8,093,453, 8,901,378, 9,994,863, 7,928,296, and 8,466,346, each of which are incorporated herein by reference in their entireties.

In certain embodiments, INIR4 plants provided herein, including plants with one or more transgenic loci, modified transgenic loci, and/or comprising transgenic loci excision sites can further comprise one or more targeted genetic changes introduced by one or more of gene editing molecules or systems. Also provided are methods where the targeted genetic changes are introduced and one or more transgenic loci are removed from plants either in series or in parallel (e.g., as set forth in the non-limiting illustration in FIG. 2, bottom "Alternative" panel, where "GE" can represent targeted genetic changes induced by gene editing molecules and "Event Removal" represents excision of one or more transgenic loci with gene editing molecules). Such targeted genetic changes include those conferring traits such as improved yield, improved food and/or feed characteristics (e.g., improved oil, starch, protein, or amino acid quality or quantity), improved nitrogen use efficiency, improved biofuel use characteristics (e.g., improved ethanol production), male sterility/conditional male sterility systems (e.g., by targeting endogenous MS26, MS45 and MSCA1 genes), herbicide tolerance (e.g., by targeting endogenous ALS, EPSPS, HPPD, or other herbicide target genes), delayed flowering, non-flowering, increased biotic stress resistance (e.g., resistance to insect, nematode, bacterial, or fungal damage), increased abiotic stress resistance (e.g., resistance to drought, cold, heat, metal, or salt), enhanced lodging resistance, enhanced growth rate, enhanced biomass, enhanced tillering, enhanced branching, delayed flowering time, delayed senescence, increased flower number, improved architecture for high density planting, improved photosynthesis, increased root mass, increased cell number, improved seedling vigor, improved seedling size, increased rate of cell division, improved metabolic efficiency, and increased meristem size in comparison to a control plant lacking the targeted genetic change. Types of targeted genetic changes that can be introduced include insertions, deletions, and substitutions of one or more nucleotides in the crop plant genome. Sites in endogenous plant genes for the targeted genetic changes include promoter, coding, and non-coding regions (e.g., 5' UTRs, introns, splice donor and acceptor sites and 3' UTRs). In certain embodiments, the targeted genetic change comprises an insertion of a regulatory or other DNA sequence in an endogenous plant gene. Non-limiting examples of regulatory sequences which can be inserted into endogenous plant genes with gene editing molecules to effect targeted genetic changes which confer useful phenotypes include those set forth in US Patent Application Publication 20190352655, which is incorporated herein by example, such as: (a) auxin response element (AuxRE) sequence; (b) at least one D1-4 sequence (Ulmasov et al. (1997) Plant Cell, 9:1963-1971), (c) at least one DR5 sequence (Ulmasov et al. (1997) Plant Cell, 9:1963-1971); (d) at least one m5-DR5 sequence (Ulmasov et al. (1997) Plant Cell, 9:1963-1971); (e) at least one P3 sequence; (f) a small RNA recognition site sequence bound by a corresponding small RNA (e.g., an siRNA, a microRNA (miRNA), a trans-acting siRNA as described in U.S. Pat. No. 8,030,473, or a phased sRNA as described in U.S. Pat. No. 8,404,928; both of these cited patents are incorporated by reference herein); (g) a microRNA (miRNA) recognition site sequence; (h) the sequence recognizable by a specific binding agent includes a microRNA (miRNA) recognition sequence for an engineered miRNA wherein the specific binding agent is the corresponding engineered mature miRNA; (i) a transposon recognition sequence; (j) a sequence recognized by an ethylene-responsive element binding-factor-associated amphiphilic repression (EAR) motif; (k) a splice site sequence (e.g., a donor site, a branching site, or an acceptor site; see, for example, the splice sites and splicing signals set forth in the internet site lemur[dot]amu[dot]edu[dot]pl/share/ERISdb/home.html); (l) a recombinase recognition site sequence that is recognized by a site-specific recombinase; (m) a sequence encoding an RNA or amino acid aptamer or an RNA riboswitch, the specific binding agent is the corresponding ligand, and the change in expression is upregulation or downregulation; (n) a hormone responsive element recognized by a nuclear receptor or a hormone-binding domain thereof; (o) a transcription factor binding sequence; and (p) a polycomb response element (see Xiao et al. (2017) Nature Genetics, 49:1546-1552, doi: 10.1038/ng.3937). Non limiting examples of target maize genes that can be subjected to targeted gene edits to confer useful traits include: (a) ZmIPK1 (herbicide tolerant and phytate reduced maize; Shukla et al., Nature. 2009; 459:437-41); (b) ZmGL2 (reduced epicuticular wax in leaves; Char et al. Plant Biotechnol J. 2015; 13:1002); (c) ZmMTL (induction of haploid plants; Kelliher et al. Nature. 2017; 542:105); (d) Wx1 (high amylopectin content; US 20190032070; incorporated herein by reference in its entirety); (e) TMSS (thermosensitive male sterile; Li et al. J Genet Genomics. 2017; 44:465-8); (f) ALS (herbicide tolerance; Svitashev et al.; Plant Physiol. 2015; 169:931-45); and (g) ARGOS8 (drought stress tolerance; Shi et al., Plant Biotechnol J. 2017; 15:207-16). Non-limiting examples of target genes in crop plants including maize which can be subjected to targeted genetic changes which confer useful phenotypes include those set forth in US Patent Application Nos. 20190352655, 20200199609, 20200157554, and 20200231982, which are each incorporated herein in their entireties; and Zhang et al. (Genome Biol. 2018; 19: 210).

Gene editing molecules of use in methods provided herein include molecules capable of introducing a double-strand break ("DSB") or single-strand break ("SSB") in double-stranded DNA, such as in genomic DNA or in a target gene located within the genomic DNA as well as accompanying guide RNA or donor DNA template polynucleotides. Examples of such gene editing molecules include: (a) a nuclease comprising an RNA-guided nuclease, an RNA-guided DNA endonuclease or RNA directed DNA endonuclease (RdDe), a class 1 CRISPR type nuclease system, a type II Cas nuclease, a Cas9, a nCas9 nickase, a type V Cas nuclease, a Cas12a nuclease, a nCas12a nickase, a Cas12d (CasY), a Cas12e (CasX), a Cas12b (C2c1), a Cas12c (C2c3), a Cas12i, a Cas12j, a Cas14, an engineered nuclease, a codon-optimized nuclease, a zinc-finger nuclease (ZFN) or nickase, a transcription activator-like effector nuclease (TAL-effector nuclease or TALEN) or nickase (TALE-nickase), an Argonaute, and a meganuclease or engineered meganuclease; (b) a polynucleotide encoding one or more nucleases capable of effectuating site-specific alteration (including introduction of a DSB or SSB) of a target nucleotide sequence; (c) a guide RNA (gRNA) for an RNA-guided nuclease, or a DNA encoding a gRNA for an RNA-guided nuclease; (d) donor DNA template polynucleotides; and (e) other DNA templates (dsDNA, ssDNA, or combinations thereof) suitable for insertion at a break in genomic DNA (e.g., by non-homologous end joining (NHEJ) or microhomology-mediated end joining (MMEJ).

CRISPR-type genome editing can be adapted for use in the plant cells and methods provided herein in several ways. CRISPR elements, e.g., gene editing molecules comprising CRISPR endonucleases and CRISPR guide RNAs including single guide RNAs or guide RNAs in combination with tracrRNAs or scoutRNA, or polynucleotides encoding the same, are useful in effectuating genome editing without remnants of the CRISPR elements or selective genetic markers occurring in progeny. In certain embodiments, the CRISPR elements are provided directly to the eukaryotic cell (e.g., plant cells), systems, methods, and compositions as isolated molecules, as isolated or semi-purified products of a cell free synthetic process (e.g., in vitro translation), or as isolated or semi-purified products of in a cell-based synthetic process (e.g., such as in a bacterial or other cell lysate). In certain embodiments, genome-inserted CRISPR elements are useful in plant lines adapted for use in the methods provide herein. In certain embodiments, plants or plant cells used in the systems, methods, and compositions provided herein can comprise a transgene that expresses a CRISPR endonuclease (e.g., a Cas9, a Cpf1-type or other CRISPR endonuclease). In certain embodiments, one or more CRISPR endonucleases with unique PAM recognition sites can be used. Guide RNAs (sgRNAs or crRNAs and a tracrRNA) to form an RNA-guided endonuclease/guide RNA complex which can specifically bind sequences in the gDNA target site that are adjacent to a protospacer adjacent motif (PAM) sequence. The type of RNA-guided endonuclease typically informs the location of suitable PAM sites and design of crRNAs or sgRNAs. G-rich PAM sites, e.g., 5'-NGG are typically targeted for design of crRNAs or sgRNAs used with Cas9 proteins. Examples of PAM sequences include 5'-NGG (*Streptococcus pyogenes*), 5'-NNAGAA (*Streptococcus thermophilus* CRISPR1), 5'-NGGNG (*Streptococcus thermophilus* CRISPR3), 5'-NNGRRT or 5'-NNGRR (*Staphylococcus aureus* Cas9, SaCas9), and 5'-NNNGATT (*Neisseria meningitidis*). T-rich PAM sites (e.g., 5'-TTN or 5'-TTTV, where "V" is A, C, or G) are typically targeted for design of crRNAs or sgRNAs used with Cas12a proteins. In some instances, Cas12a can also recognize a 5'-CTA PAM motif. Other examples of potential Cas12a PAM sequences include TTN, CTN, TCN, CCN, TTTN, TCTN, TTCN, CTTN, ATTN, TCCN, TTGN, GTTN, CCCN, CCTN, TTAN, TCGN, CTCN, ACTN, GCTN, TCAN, GCCN, and CCGN (wherein N is defined as any nucleotide). Cpf1 (i.e., Cas12a) endonuclease and corresponding guide RNAs and PAM sites are disclosed in US Patent Application Publication 2016/0208243 A1, which is incorporated herein by reference for its disclosure of DNA encoding Cpf1 endonucleases and guide RNAs and PAM sites. Introduction of one or more of a wide variety of CRISPR guide RNAs that interact with CRISPR endonucleases integrated into a plant genome or otherwise provided to a plant is useful for genetic editing for providing desired phenotypes or traits, for trait screening, or for gene editing mediated trait introgression (e.g., for introducing a trait into a new genotype without backcrossing to a recurrent parent or with limited backcrossing to a recurrent parent). Multiple endonucleases can be provided in expression cassettes with the appropriate promoters to allow multiple genome site editing.

CRISPR technology for editing the genes of eukaryotes is disclosed in US Patent Application Publications 2016/0138008A1 and US2015/0344912A1, and in U.S. Pat. Nos. 8,697,359, 8,771,945, 8,945,839, 8,999,641, 8,993,233, 8,895,308, 8,865,406, 8,889,418, 8,871,445, 8,889,356, 8,932,814, 8,795,965, and 8,906,616. Cpf1 endonuclease and corresponding guide RNAs and PAM sites are disclosed in US Patent Application Publication 2016/0208243 A1. Other CRISPR nucleases useful for editing genomes include Cas12b and Cas12c (see Shmakov et al. (2015) Mol. Cell, 60:385-397; Harrington et al. (2020) Molecular Cell doi: 10.1016/j.molcel.2020.06.022) and CasX and CasY (see Burstein et al. (2016) Nature, doi:10.1038/nature21059; Harrington et al. (2020) Molecular Cell doi:10.1016/j.molcel.2020.06.022), or Cas12j (Pausch et al, (2020) Science 10.1126/science.abb1400). Plant RNA promoters for expressing CRISPR guide RNA and plant codon-optimized CRISPR Cas9 endonuclease are disclosed in International Patent Application PCT/US2015/018104 (published as WO 2015/131101 and claiming priority to U.S. Provisional Patent Application 61/945,700). Methods of using CRISPR technology for genome editing in plants are disclosed in US Patent Application Publications US 2015/0082478A1 and US 2015/0059010A1 and in International Patent Application PCT/US2015/038767 A1 (published as WO 2016/007347 and claiming priority to U.S. Provisional Patent Application 62/023,246). All of the patent publications referenced in this paragraph are incorporated herein by reference in their entirety. In certain embodiments, an RNA-guided endonuclease that leaves a blunt end following cleavage of the target site is used. Blunt-end cutting RNA-guided endonucleases include Cas9, Cas12c, and Cas 12h (Yan et al., 2019). In certain embodiments, an RNA-guided endonuclease that leaves a staggered single stranded DNA overhanging end following cleavage of the target site following cleavage of the target site is used. Staggered-end cutting RNA-guided endonucleases include Cas12a, Cas12b, and Cas12e.

The methods can also use sequence-specific endonucleases or sequence-specific endonucleases and guide RNAs that cleave a single DNA strand in a dsDNA target site. Such cleavage of a single DNA strand in a dsDNA target site is also referred to herein and elsewhere as "nicking" and can be effected by various "nickases" or systems that provide for nicking. Nickases that can be used include nCas9 (Cas9 comprising a D10A amino acid substitution), nCas12a (e.g., Cas12a comprising an R1226A amino acid substitution; Yamano et al., 2016), Cas12i (Yan et al. 2019), a zinc finger nickase e.g., as disclosed in Kim et al., 2012), a TALE nickase (e.g., as disclosed in Wu et al., 2014), or a combination thereof. In certain embodiments, systems that provide for nicking can comprise a Cas nuclease (e.g., Cas9 and/or Cas12a) and guide RNA molecules that have at least one base mismatch to DNA sequences in the target editing site (Fu et al., 2019). In certain embodiments, genome modifications can be introduced into the target editing site by creating single stranded breaks (i.e., "nicks") in genomic locations separated by no more than about 10, 20, 30, 40, 50, 60, 80, 100, 150, or 200 base pairs of DNA. In certain illustrative and non-limiting embodiments, two nickases (i.e., a CAS nuclease which introduces a single stranded DNA break including nCas9, nCas12a, Cas12i, zinc finger nickases, TALE nickases, combinations thereof, and the like) or nickase systems can directed to make cuts to nearby sites separated by no more than about 10, 20, 30, 40, 50, 60, 80 or 100 base pairs of DNA. In instances where an RNA guided nickase and an RNA guide are used, the RNA guides are adjacent to PAM sequences that are sufficiently close (i.e., separated by no more than about 10, 20, 30, 40, 50, 60, 80, 100, 150, or 200 base pairs of DNA). For the purposes of gene editing, CRISPR arrays can be designed to contain one or multiple guide RNA sequences corresponding to a desired target DNA sequence; see, for example, Cong et al. (2013) *Science,* 339:819-823; Ran et al. (2013) *Nature Protocols,* 8:2281-2308. At least 16 or 17 nucleotides of gRNA sequence are required by Cas9 for DNA cleavage to occur; for Cpf1 at least 16 nucleotides of gRNA sequence are needed to achieve detectable DNA cleavage and at least 18 nucleotides of gRNA sequence were reported necessary for efficient DNA cleavage in vitro; see Zetsche et al. (2015) Cell, 163:759-771. In practice, guide RNA sequences are generally designed to have a length of 17-24 nucleotides (frequently 19, 20, or 21 nucleotides) and exact complementarity (i.e., perfect base-pairing) to the targeted gene or nucleic acid sequence; guide RNAs having less than 100% complementarity to the target sequence can be used (e.g., a gRNA with a length of 20 nucleotides and 1-4 mismatches to the target sequence) but can increase the potential for off-target effects. The design of effective guide RNAs for use in plant genome editing is disclosed in US Patent Application Publication 2015/0082478 A1, the entire specification of which is incorporated herein by reference. More recently, efficient gene editing has been achieved using a chimeric "single guide RNA" ("sgRNA"), an engineered (synthetic) single RNA molecule that mimics a naturally occurring crRNA-tracrRNA complex and contains both a tracrRNA (for binding the nuclease) and at least one crRNA (to guide the nuclease to the sequence targeted for editing); see, for example, Cong et al. (2013) *Science,* 339:819-823; Xing et al. (2014) *BMC Plant Biol.,* 14:327-340. Chemically modified sgRNAs have been demonstrated to be effective in genome editing; see, for example, Hendel et al. (2015) *Nature Biotechnol.,* 985-991. The design of effective gRNAs for use in plant genome editing is disclosed in US Patent Application Publication 2015/0082478 A1, the entire specification of which is incorporated herein by reference.

Genomic DNA may also be modified via base editing. Both adenine base editors (ABE) which convert A/T base pairs to G/C base pairs in genomic DNA as well as cytosine base pair editors (CBE) which effect C to T substitutions can be used in certain embodiments of the methods provided herein. In certain embodiments, useful ABE and CBE can comprise genome site specific DNA binding elements (e.g., RNA-dependent DNA binding proteins including catalytically inactive Cas9 and Cas12 proteins or Cas9 and Cas12 nickases) operably linked to adenine or cytidine deaminases and used with guide RNAs which position the protein near the nucleotide targeted for substitution. Suitable ABE and CBE disclosed in the literature (Kim, Nat Plants, 2018 March; 4(3):148-151) can be adapted for use in the methods set forth herein. In certain embodiments, a CBE can comprise a fusion between a catalytically inactive Cas9 (dCas9)

RNA dependent DNA binding protein fused to a cytidine deaminase which converts cytosine (C) to uridine (U) and selected guide RNAs, thereby effecting a C to T substitution; see Komor et al. (2016) Nature, 533:420-424. In other embodiments, C to T substitutions are effected with Cas9 nickase [Cas9n(D10A)] fused to an improved cytidine deaminase and optionally a bacteriophage Mu dsDNA (double-stranded DNA) end-binding protein Gam; see Komor et al., Sci Adv. 2017 August; 3(8):eaao4774. In other embodiments, adenine base editors (ABEs) comprising an adenine deaminase fused to catalytically inactive Cas9 (dCas9) or a Cas9 D10A nickase can be used to convert A/T base pairs to G/C base pairs in genomic DNA (Gaudelli et al., (2017) Nature 551(7681):464-471.

In certain embodiments, zinc finger nucleases or zinc finger nickases can also be used in the methods provided herein. Zinc-finger nucleases are site-specific endonucleases comprising two protein domains: a DNA-binding domain, comprising a plurality of individual zinc finger repeats that each recognize between 9 and 18 base pairs, and a DNA-cleavage domain that comprises a nuclease domain (typically FokI). The cleavage domain dimerizes in order to cleave DNA; therefore, a pair of ZFNs are required to target non-palindromic target polynucleotides. In certain embodiments, zinc finger nuclease and zinc finger nickase design methods which have been described (Urnov et al. (2010) Nature Rev. Genet., 11:636-646; Mohanta et al. (2017) Genes vol. 8,12: 399; Ramirez et al. Nucleic Acids Res. (2012); 40(12): 5560-5568; Liu et al. (2013) Nature Communications, 4: 2565) can be adapted for use in the methods set forth herein. The zinc finger binding domains of the zinc finger nuclease or nickase provide specificity and can be engineered to specifically recognize any desired target DNA sequence. The zinc finger DNA binding domains are derived from the DNA-binding domain of a large class of eukaryotic transcription factors called zinc finger proteins (ZFPs). The DNA-binding domain of ZFPs typically contains a tandem array of at least three zinc "fingers" each recognizing a specific triplet of DNA. A number of strategies can be used to design the binding specificity of the zinc finger binding domain. One approach, termed "modular assembly", relies on the functional autonomy of individual zinc fingers with DNA. In this approach, a given sequence is targeted by identifying zinc fingers for each component triplet in the sequence and linking them into a multifinger peptide. Several alternative strategies for designing zinc finger DNA binding domains have also been developed. These methods are designed to accommodate the ability of zinc fingers to contact neighboring fingers as well as nucleotide bases outside their target triplet. Typically, the engineered zinc finger DNA binding domain has a novel binding specificity, compared to a naturally-occurring zinc finger protein. Engineering methods include, for example, rational design and various types of selection. Rational design includes, for example, the use of databases of triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, e.g., U.S. Pat. Nos. 6,453,242 and 6,534,261, both incorporated herein by reference in their entirety. Exemplary selection methods (e.g., phage display and yeast two-hybrid systems) can be adapted for use in the methods described herein. In addition, enhancement of binding specificity for zinc finger binding domains has been described in U.S. Pat. No. 6,794,136, incorporated herein by reference in its entirety. In addition, individual zinc finger domains may be linked together using any suitable linker sequences. Examples of linker sequences are publicly known, e.g., see U.S. Pat. Nos. 6,479,626; 6,903,185; and 7,153,949, incorporated herein by reference in their entirety. The nucleic acid cleavage domain is non-specific and is typically a restriction endonuclease, such as FokI. This endonuclease must dimerize to cleave DNA. Thus, cleavage by FokI as part of a ZFN requires two adjacent and independent binding events, which must occur in both the correct orientation and with appropriate spacing to permit dimer formation. The requirement for two DNA binding events enables more specific targeting of long and potentially unique recognition sites. FokI variants with enhanced activities have been described and can be adapted for use in the methods described herein; see, e.g., Guo et al. (2010)J. Mol. Biol., 400:96-107.

Transcription activator like effectors (TALEs) are proteins secreted by certain Xanthomonas species to modulate gene expression in host plants and to facilitate the colonization by and survival of the bacterium. TALEs act as transcription factors and modulate expression of resistance genes in the plants. Recent studies of TALEs have revealed the code linking the repetitive region of TALEs with their target DNA-binding sites. TALEs comprise a highly conserved and repetitive region consisting of tandem repeats of mostly 33 or 34 amino acid segments. The repeat monomers differ from each other mainly at amino acid positions 12 and 13. A strong correlation between unique pairs of amino acids at positions 12 and 13 and the corresponding nucleotide in the TALE-binding site has been found. The simple relationship between amino acid sequence and DNA recognition of the TALE binding domain allows for the design of DNA binding domains of any desired specificity. TALEs can be linked to a non-specific DNA cleavage domain to prepare genome editing proteins, referred to as TAL-effector nucleases or TALENs. As in the case of ZFNs, a restriction endonuclease, such as FokI, can be conveniently used. Methods for use of TALENs in plants have been described and can be adapted for use in the methods described herein, see Mahfouz et al. (2011) Proc. Natl. Acad. Sci. USA, 108:2623-2628; Mahfouz (2011) GM Crops, 2:99-103; and Mohanta et al. (2017) Genes vol. 8,12: 399). TALE nickases have also been described and can be adapted for use in methods described herein (Wu et al.; Biochem Biophys Res Commun. (2014); 446(1):261-6; Luo et al; Scientific Reports 6, Article number: 20657 (2016)).

Embodiments of the donor DNA template molecule having a sequence that is integrated at the site of at least one double-strand break (DSB) in a genome include double-stranded DNA, a single-stranded DNA, a single-stranded DNA/RNA hybrid, and a double-stranded DNA/RNA hybrid. In embodiments, a donor DNA template molecule that is a double-stranded (e.g., a dsDNA or dsDNA/RNA hybrid) molecule is provided directly to the plant protoplast or plant cell in the form of a double-stranded DNA or a double-stranded DNA/RNA hybrid, or as two single-stranded DNA (ssDNA) molecules that are capable of hybridizing to form dsDNA, or as a single-stranded DNA molecule and a single-stranded RNA (ssRNA) molecule that are capable of hybridizing to form a double-stranded DNA/RNA hybrid; that is to say, the double-stranded polynucleotide molecule is not provided indirectly, for example, by expression in the cell of a dsDNA encoded by a plasmid or other vector. In various non-limiting embodiments of the method, the donor DNA template molecule that is integrated (or that has a sequence that is integrated) at the site of at least one double-strand break (DSB) in a genome is double-stranded and blunt-ended; in other embodiments the donor DNA template molecule is double-stranded and has an overhang or "sticky end" consisting of unpaired nucleotides (e.g., 1, 2, 3, 4, 5, or 6 unpaired nucleotides) at one terminus or both termini. In an embodiment, the DSB in the genome has no unpaired nucleotides at the cleavage site, and the donor DNA template molecule that is integrated (or that has a sequence that is integrated) at the site of the DSB is a blunt-ended double-stranded DNA or blunt-ended double-stranded DNA/RNA hybrid molecule, or alternatively is a single-stranded DNA or a single-stranded DNA/RNA hybrid molecule. In another embodiment, the DSB in the genome has one or more unpaired nucleotides at one or both sides of the cleavage site, and the donor DNA template molecule that is integrated (or that has a sequence that is integrated) at the site of the DSB is a double-stranded DNA or double-stranded DNA/RNA hybrid molecule with an overhang or "sticky end" consisting of unpaired nucleotides at one or both termini, or alternatively is a single-stranded DNA or a single-stranded DNA/RNA hybrid molecule; in embodiments, the donor DNA template molecule DSB is a double-stranded DNA or double-stranded DNA/RNA hybrid molecule that includes an overhang at one or at both termini, wherein the overhang consists of the same number of unpaired nucleotides as the number of unpaired nucleotides created at the site of a DSB by a nuclease that cuts in an off-set fashion (e.g., where a Cas12 nuclease effects an off-set DSB with 5-nucleotide overhangs in the genomic sequence, the donor DNA template molecule that is to be integrated (or that has a sequence that is to be integrated) at the site of the DSB is double-stranded and has 5 unpaired nucleotides at one or both termini). In certain embodiments, one or both termini of the donor DNA template molecule contain no regions of sequence homology (identity or complementarity) to genomic regions flanking the DSB; that is to say, one or both termini of the donor DNA template molecule contain no regions of sequence that is sufficiently complementary to permit hybridization to genomic regions immediately adjacent to the location of the DSB. In embodiments, the donor DNA template molecule contains no homology to the locus of the DSB, that is to say, the donor DNA template molecule contains no nucleotide sequence that is sufficiently complementary to permit hybridization to genomic regions immediately adjacent to the location of the DSB. In embodiments, the donor DNA template molecule is at least partially double-stranded and includes 2-20 base-pairs, e.g., 2, 3, 4, 5, 6, 7, 8, 9, 10, 11, 12, 13, 14, 15, 16, 17, 18, 19, or 20 base-pairs; in embodiments, the donor DNA template molecule is double-stranded and blunt-ended and consists of 2-20 base-pairs, e.g., 2, 3, 4, 5, 6, 7, 8, 9, 10, 11, 12, 13, 14, 15, 16, 17, 18, 19, or 20 base-pairs; in other embodiments, the donor DNA template molecule is double-stranded and includes 2-20 base-pairs, e.g., 2, 3, 4, 5, 6, 7, 8, 9, 10, 11, 12, 13, 14, 15, 16, 17, 18, 19, or 20 base-pairs and in addition has at least one overhang or "sticky end" consisting of at least one additional, unpaired nucleotide at one or at both termini. In an embodiment, the donor DNA template molecule that is integrated (or that has a sequence that is integrated) at the site of at least one double-strand break (DSB) in a genome is a blunt-ended double-stranded DNA or a blunt-ended double-stranded DNA/RNA hybrid molecule of about 18 to about 300 base-pairs, or about 20 to about 200 base-pairs, or about 30 to about 100 base-pairs, and having at least one phosphorothioate bond between adjacent nucleotides at a 5' end, 3' end, or both 5' and 3' ends. In embodiments, the donor DNA template molecule includes single strands of at least 11, at least 18, at least 20, at least 30, at least 40, at least 60, at least 80, at least 100, at least 120, at least 140, at least 160, at least 180, at least 200, at least 240, at about 280, or at least 320 nucleotides. In embodiments, the donor DNA template molecule has a length of at least 2, at least 3, at least 4, at least 5, at least 6, at least 7, at least 8, at least 9, at least 10, or at least 11 base-pairs if double-stranded (or nucleotides if single-stranded), or between about 2 to about 320 base-pairs if double-stranded (or nucleotides if single-stranded), or between about 2 to about 500 base-pairs if double-stranded (or nucleotides if single-stranded), or between about 5 to about 500 base-pairs if double-stranded (or nucleotides if single-stranded), or between about 5 to about 300 base-pairs if double-stranded (or nucleotides if single-stranded), or between about 11 to about 300 base-pairs if double-stranded (or nucleotides if single-stranded), or about 18 to about 300 base-pairs if double-stranded (or nucleotides if single-stranded), or between about 30 to about 100 base-pairs if double-stranded (or nucleotides if single-stranded). In embodiments, the donor DNA template molecule includes chemically modified nucleotides (see, e.g., the various modifications of internucleotide linkages, bases, and sugars described in Verma and Eckstein (1998) Annu. Rev. Biochem., 67:99-134); in embodiments, the naturally occurring phosphodiester backbone of the donor DNA template molecule is partially or completely modified with phosphorothioate, phosphorodithioate, or methylphosphonate internucleotide linkage modifications, or the donor DNA template molecule includes modified nucleoside bases or modified sugars, or the donor DNA template molecule is labelled with a fluorescent moiety (e.g., fluorescein or rhodamine or a fluorescent nucleoside analogue) or other detectable label (e.g., biotin or an isotope). In another embodiment, the donor DNA template molecule contains secondary structure that provides stability or acts as an aptamer. Other related embodiments include double-stranded DNA/RNA hybrid molecules, single-stranded DNA/RNA hybrid donor molecules, and single-stranded donor DNA template molecules (including single-stranded, chemically modified donor DNA template molecules), which in analogous procedures are integrated (or have a sequence that is integrated) at the site of a double-strand break. Donor DNA templates provided herein include those comprising CgRRS sequences flanked by DNA with homology to a donor polynucleotide and include the donor DNA template set forth in SEQ ID NO: 11, 24, 28, and equivalents thereof with longer or shorter homology arms. In certain embodiments, a donor DNA template can comprise an adapter molecule with cohesive ends which can anneal to an overhanging cleavage site (e.g., introduced by a Cas12a nuclease and suitable gRNAs). In certain embodiments, integration of the donor DNA templates can be facilitated by use of a bacteriophage lambda exonuclease, a bacteriophage lambda beta SSAP protein, and an E. coli SSB essentially as set forth in US Patent Application Publication 20200407754, which is incorporated herein by reference in its entirety.

Donor DNA template molecules used in the methods provided herein include DNA molecules comprising, from 5' to 3', a first homology arm, a replacement DNA, and a second homology arm, wherein the homology arms containing sequences that are partially or completely homologous to genomic DNA (gDNA) sequences flanking a target site-specific endonuclease cleavage site in the gDNA. In certain embodiments, the replacement DNA can comprise an insertion, deletion, or substitution of 1 or more DNA base pairs relative to the target gDNA. In an embodiment, the donor DNA template molecule is double-stranded and perfectly base-paired through all or most of its length, with the possible exception of any unpaired nucleotides at either terminus or both termini. In another embodiment, the donor DNA template molecule is double-stranded and includes one or more non-terminal mismatches or non-terminal unpaired nucleotides within the otherwise double-stranded duplex. In an embodiment, the donor DNA template molecule that is integrated at the site of at least one double-strand break (DSB) includes between 2-20 nucleotides in one (if single-stranded) or in both strands (if double-stranded), e.g., 2, 3, 4, 5, 6, 7, 8, 9, 10, 11, 12, 13, 14, 15, 16, 17, 18, 19, or 20 nucleotides on one or on both strands, each of which can be base-paired to a nucleotide on the opposite strand (in the case of a perfectly base-paired double-stranded polynucleotide molecule). Such donor DNA templates can be integrated in genomic DNA containing blunt and/or staggered double stranded DNA breaks by homology-directed repair (HDR). In certain embodiments, a donor DNA template homology arm can be about 20, 50, 100, 200, 400, or 600 to about 800, or 1000 base pairs in length. In certain embodiments, a donor DNA template molecule can be delivered to a plant cell) in a circular (e.g., a plasmid or a viral vector including a geminivirus vector) or a linear DNA molecule. In certain embodiments, a circular or linear DNA molecule that is used can comprise a modified donor DNA template molecule comprising, from 5' to 3', a first copy of the target sequence-specific endonuclease cleavage site sequence, the first homology arm, the replacement DNA, the second homology arm, and a second copy of the target sequence-specific endonuclease cleavage site sequence. Without seeking to be limited by theory, such modified donor DNA template molecules can be cleaved by the same sequence-specific endonuclease that is used to cleave the target site gDNA of the eukaryotic cell to release a donor DNA template molecule that can participate in HDR-mediated genome modification of the target editing site in the plant cell genome. In certain embodiments, the donor DNA template can comprise a linear DNA molecule comprising, from 5' to 3', a cleaved target sequence-specific endonuclease cleavage site sequence, the first homology arm, the replacement DNA, the second homology arm, and a cleaved target sequence-specific endonuclease cleavage site sequence. In certain embodiments, the cleaved target sequence-specific endonuclease sequence can comprise a blunt DNA end or a blunt DNA end that can optionally comprise a 5' phosphate group. In certain embodiments, the cleaved target sequence-specific endonuclease sequence comprises a DNA end having a single-stranded 5' or 3' DNA overhang. Such cleaved target sequence-specific endonuclease cleavage site sequences can be produced by either cleaving an intact target sequence-specific endonuclease cleavage site sequence or by synthesizing a copy of the cleaved target sequence-specific endonuclease cleavage site sequence. Donor DNA templates can be synthesized either chemically or enzymatically (e.g., in a polymerase chain reaction (PCR)). Donor DNA templates provided herein include those comprising CgRRS sequences flanked by DNA with homology to a donor polynucleotide.

Various treatments are useful in delivery of gene editing molecules and/or other molecules to a DAS59122-7 or INIR4 plant cell. In certain embodiments, one or more treatments is employed to deliver the gene editing or other molecules (e.g., comprising a polynucleotide, polypeptide or combination thereof) into a eukaryotic or plant cell, e.g., through barriers such as a cell wall, a plasma membrane, a nuclear envelope, and/or other lipid bilayer. In certain embodiments, a polynucleotide-, polypeptide-, or RNP-containing composition comprising the molecules are delivered directly, for example by direct contact of the composition with a plant cell. Aforementioned compositions can be provided in the form of a liquid, a solution, a suspension, an emulsion, a reverse emulsion, a colloid, a dispersion, a gel, liposomes, micelles, an injectable material, an aerosol, a solid, a powder, a particulate, a nanoparticle, or a combination thereof can be applied directly to a plant, plant part, plant cell, or plant explant (e.g., through abrasion or puncture or otherwise disruption of the cell wall or cell membrane, by spraying or dipping or soaking or otherwise directly contacting, by microinjection). For example, a plant cell or plant protoplast is soaked in a liquid genome editing molecule-containing composition, whereby the agent is delivered to the plant cell. In certain embodiments, the agent-containing composition is delivered using negative or positive pressure, for example, using vacuum infiltration or application of hydrodynamic or fluid pressure. In certain embodiments, the agent-containing composition is introduced into a plant cell or plant protoplast, e.g., by microinjection or by disruption or deformation of the cell wall or cell membrane, for example by physical treatments such as by application of negative or positive pressure, shear forces, or treatment with a chemical or physical delivery agent such as surfactants, liposomes, or nanoparticles; see, e.g., delivery of materials to cells employing microfluidic flow through a cell-deforming constriction as described in US Published Patent Application 2014/0287509, incorporated by reference in its entirety herein. Other techniques useful for delivering the agent-containing composition to a eukaryotic cell, plant cell or plant protoplast include: ultrasound or sonication; vibration, friction, shear stress, vortexing, cavitation; centrifugation or application of mechanical force; mechanical cell wall or cell membrane deformation or breakage; enzymatic cell wall or cell membrane breakage or permeabilization; abrasion or mechanical scarification (e.g., abrasion with carborundum or other particulate abrasive or scarification with a file or sandpaper) or chemical scarification (e.g., treatment with an acid or caustic agent); and electroporation. In certain embodiments, the agent-containing composition is provided by bacterially mediated (e.g., *Agrobacterium* sp., *Rhizobium* sp., *Sinorhizobium* sp., *Mesorhizobium* sp., *Bradyrhizobium* sp., *Azobacter* sp., *Phyllobacterium* sp.) transfection of the plant cell or plant protoplast with a polynucleotide encoding the genome editing molecules (e.g., RNA dependent DNA endonuclease, RNA dependent DNA binding protein, RNA dependent nickase, ABE, or CBE, and/or guide RNA); see, e.g., Broothaerts et al. (2005) *Nature*, 433:629-633). Any of these techniques or a combination thereof are alternatively employed on the plant explant, plant part or tissue or intact plant (or seed) from which a plant cell is optionally subsequently obtained or isolated; in certain embodiments, the agent-containing composition is delivered in a separate step after the plant cell has been isolated.

In some embodiments, one or more polynucleotides or vectors driving expression of one or more genome editing molecules or trait-conferring genes (e.g., herbicide tolerance, insect resistance, and/or male sterility) are introduced into a DAS59122-7 or INIR4 plant cell. In certain embodiments, a polynucleotide vector comprises a regulatory element such as a promoter operably linked to one or more polynucleotides encoding genome editing molecules and/or trait-conferring genes. In such embodiments, expression of these polynucleotides can be controlled by selection of the appropriate promoter, particularly promoters functional in a eukaryotic cell (e.g., plant cell); useful promoters include constitutive, conditional, inducible, and temporally or spatially specific promoters (e.g., a tissue specific promoter, a developmentally regulated promoter, or a cell cycle regulated promoter). Developmentally regulated promoters that can be used in plant cells include Phospholipid Transfer Protein (PLTP), fructose-1,6-bisphosphatase protein, NAD (P)-binding Rossmann-Fold protein, adipocyte plasma membrane-associated protein-like protein, Rieske [2Fe-2S] iron-sulfur domain protein, chlororespiratory reduction 6 protein, D-glycerate 3-kinase, chloroplastic-like protein, chlorophyll a-b binding protein 7, chloroplastic-like protein, ultraviolet-B-repressible protein, Soul heme-binding family protein, Photosystem I reaction center subunit psi-N protein, and short-chain dehydrogenase/reductase protein that are disclosed in US Patent Application Publication No. 20170121722, which is incorporated herein by reference in its entirety and specifically with respect to such disclosure. In certain embodiments, the promoter is operably linked to nucleotide sequences encoding multiple guide RNAs, wherein the sequences encoding guide RNAs are separated by a cleavage site such as a nucleotide sequence encoding a microRNA recognition/cleavage site or a self-cleaving ribozyme (see, e.g., Ferré-D'Amaré and Scott (2014) Cold Spring Harbor Perspectives Biol., 2:a003574). In certain embodiments, the promoter is an RNA polymerase III promoter operably linked to a nucleotide sequence encoding one or more guide RNAs. In certain embodiments, the RNA polymerase III promoter is a plant U6 spliceosomal RNA promoter, which can be native to the genome of the plant cell or from a different species, e.g., a U6 promoter from maize, tomato, or soybean such as those disclosed U.S. Patent Application Publication 2017/0166912, or a homologue thereof; in an example, such a promoter is operably linked to DNA sequence encoding a first RNA molecule including a Cas12a gRNA followed by an operably linked and suitable 3' element such as a U6 poly-T terminator. In another embodiment, the RNA polymerase III promoter is a plant U3, 7SL (signal recognition particle RNA), U2, or U5 promoter, or chimerics thereof, e.g., as described in U.S. Patent Application Publication 20170166912. In certain embodiments, the promoter operably linked to one or more polynucleotides is a constitutive promoter that drives gene expression in eukaryotic cells (e.g., plant cells). In certain embodiments, the promoter drives gene expression in the nucleus or in an organelle such as a chloroplast or mitochondrion. Examples of constitutive promoters for use in plants include a CaMV 35S promoter as disclosed in U.S. Pat. Nos. 5,858,742 and 5,322,938, a rice actin promoter as disclosed in U.S. Pat. No. 5,641,876, a maize chloroplast aldolase promoter as disclosed in U.S. Pat. No. 7,151,204, and the nopaline synthase (NOS) and octopine synthase (OCS) promoters from *Agrobacterium tumefaciens*. In certain embodiments, the promoter operably linked to one or more polynucleotides encoding elements of a genome-editing system is a promoter from figwort mosaic virus (FMV), a RUBISCO promoter, or a pyruvate phosphate dikinase (PPDK) promoter, which is active in photosynthetic tissues. Other contemplated promoters include cell-specific or tissue-specific or developmentally regulated promoters, for example, a promoter that limits the expression of the nucleic acid targeting system to germline or reproductive cells (e.g., promoters of genes encoding DNA ligases, recombinases, replicases, or other genes specifically expressed in germline or reproductive cells). In certain embodiments, the genome alteration is limited only to those cells from which DNA is inherited in subsequent generations, which is advantageous where it is desirable that expression of the genome-editing system be limited in order to avoid genotoxicity or other unwanted effects. All of the patent publications referenced in this paragraph are incorporated herein by reference in their entirety.

Expression vectors or polynucleotides provided herein may contain a DNA segment near the 3' end of an expression cassette that acts as a signal to terminate transcription and directs polyadenylation of the resultant mRNA, and may also support promoter activity. Such a 3' element is commonly referred to as a "3'-untranslated region" or "3'-UTR" or a "polyadenylation signal." In some cases, plant gene-based 3' elements (or terminators) consist of both the 3'-UTR and downstream non-transcribed sequence (Nuccio et al., 2015). Useful 3' elements include: *Agrobacterium tumefaciens* nos 3', tml 3', tmr 3', tms 3', ocs 3', and tr7 3' elements disclosed in U.S. Pat. No. 6,090,627, incorporated herein by reference, and 3' elements from plant genes such as the heat shock protein 17, ubiquitin, and fructose-1,6-biphosphatase genes from wheat (*Triticum aestivum*), and the glutelin, lactate dehydrogenase, and beta-tubulin genes from rice (*Oryza sativa*), disclosed in US Patent Application Publication 2002/0192813 A1. All of the patent publications referenced in this paragraph are incorporated herein by reference in their entireties.

In certain embodiments, the DAS59122-7 or INIR4 plant cells used herein can comprise haploid, diploid, or polyploid plant cells or plant protoplasts, for example, those obtained from a haploid, diploid, or polyploid plant, plant part or tissue, or callus. In certain embodiments, plant cells in culture (or the regenerated plant, progeny seed, and progeny plant) are haploid or can be induced to become haploid; techniques for making and using haploid plants and plant cells are known in the art, see, e.g., methods for generating haploids in *Arabidopsis thaliana* by crossing of a wild-type strain to a haploid-inducing strain that expresses altered forms of the centromere-specific histone CENH3, as described by Maruthachalam and Chan in "How to make haploid *Arabidopsis thaliana*", protocol available at www[dot]openwetware[dot]org/images/d/d3/Haploid_Arabidopsis_protocol[dot]pdf; (Ravi et al. (2014) *Nature Communications*, 5:5334, doi: 10.1038/ncomms6334). Haploids can also be obtained in a wide variety of monocot plants (e.g., maize, wheat, rice, sorghum, barley) by crossing a plant comprising a mutated CENH3 gene with a wildtype diploid plant to generate haploid progeny as disclosed in U.S. Pat. No. 9,215,849, which is incorporated herein by reference in its entirety. Haploid-inducing maize lines that can be used to obtain haploid maize plants and/or cells include Stock 6, MHI (Moldovian Haploid Inducer), indeterminate gametophyte (ig) mutation, KEMS, RWK, ZEM, ZMS, KMS, and well as transgenic haploid inducer lines disclosed in U.S. Pat. No. 9,677,082, which is incorporated herein by reference in its entirety. Examples of haploid cells include but are not limited to plant cells obtained from haploid plants and plant cells obtained from reproductive tissues, e.g., from flowers, developing flowers or flower buds, ovaries, ovules, megaspores, anthers, pollen, megagametophyte, and microspores. In certain embodiments where the plant cell or plant protoplast is haploid, the genetic complement can be doubled by chromosome doubling (e.g., by spontaneous chromosomal doubling by meiotic non-reduction, or by using a chromosome doubling agent such as colchicine, oryzalin, trifluralin, pronamide, nitrous oxide gas, anti-microtubule herbicides, anti-microtubule agents, and mitotic inhibitors) in the plant cell or plant protoplast to produce a doubled haploid plant cell or plant protoplast wherein the complement of genes or alleles is homozygous; yet other embodiments include regeneration of a doubled haploid plant from the doubled haploid plant cell or plant protoplast. Another embodiment is related to a hybrid plant having at least one parent plant that is a doubled haploid plant provided by this approach. Production of doubled haploid plants provides homozygosity in one generation, instead of requiring several generations of self-crossing to obtain homozygous plants. The use of doubled haploids is advantageous in any situation where there is a desire to establish genetic purity (i.e., homozygosity) in the least possible time. Doubled haploid production can be particularly advantageous in slow-growing plants or for producing hybrid plants that are offspring of at least one doubled-haploid plant.

In certain embodiments, the DAS59122-7 or INIR4 plant cells used in the methods provided herein can include non-dividing cells. Such non-dividing cells can include plant cell protoplasts, plant cells subjected to one or more of a genetic and/or pharmaceutically-induced cell-cycle blockage, and the like.

In certain embodiments, the DAS59122-7 or INIR4 plant cells in used in the methods provided herein can include dividing cells. Dividing cells can include those cells found in various plant tissues including leaves, meristems, and embryos. These tissues include dividing cells from young maize leaf, meristems and scutellar tissue from about 8 or 10 to about 12 or 14 days after pollination (DAP) embryos. The isolation of maize embryos has been described in several publications (Brettschneider, Becker, and Lörz 1997; Leduc et al. 1996; Frame et al. 2011; K. Wang and Frame 2009). In certain embodiments, basal leaf tissues (e.g., leaf tissues located about 0 to 3 cm from the ligule of a maize plant; Kirienko, Luo, and Sylvester 2012) are targeted for HDR-mediated gene editing. Methods for obtaining regenerable plant structures and regenerating plants from the NHEJ-, MMEJ-, or HDR-mediated gene editing of plant cells provided herein can be adapted from methods disclosed in US Patent Application Publication No. 20170121722, which is incorporated herein by reference in its entirety and specifically with respect to such disclosure. In certain embodiments, single plant cells subjected to the HDR-mediated gene editing will give rise to single regenerable plant structures. In certain embodiments, the single regenerable plant cell structure can form from a single cell on, or within, an explant that has been subjected to the NHEJ-, MMEJ-, or HDR-mediated gene editing.

In some embodiments, methods provided herein can include the additional step of growing or regenerating an INIR4 plant from a INIR4 plant cell that had been subjected to the gene editing or from a regenerable plant structure obtained from that INIR4 plant cell. In certain embodiments, the plant can further comprise an inserted transgene, a target gene edit, or genome edit as provided by the methods and compositions disclosed herein. In certain embodiments, callus is produced from the plant cell, and plantlets and plants produced from such callus. In other embodiments, whole seedlings or plants are grown directly from the plant cell without a callus stage. Thus, additional related aspects are directed to whole seedlings and plants grown or regenerated from the plant cell or plant protoplast having a target gene edit or genome edit, as well as the seeds of such plants. In certain embodiments wherein the plant cell or plant protoplast is subjected to genetic modification (for example, genome editing by means of, e.g., an RdDe), the grown or regenerated plant exhibits a phenotype associated with the genetic modification. In certain embodiments, the grown or regenerated plant includes in its genome two or more genetic or epigenetic modifications that in combination provide at least one phenotype of interest. In certain embodiments, a heterogeneous population of plant cells having a target gene edit or genome edit, at least some of which include at least one genetic or epigenetic modification, is provided by the method; related aspects include a plant having a phenotype of interest associated with the genetic or epigenetic modification, provided by either regeneration of a plant having the phenotype of interest from a plant cell or plant protoplast selected from the heterogeneous population of plant cells having a target gene or genome edit, or by selection of a plant having the phenotype of interest from a heterogeneous population of plants grown or regenerated from the population of plant cells having a targeted genetic edit or genome edit. Examples of phenotypes of interest include herbicide resistance, improved tolerance of abiotic stress (e.g., tolerance of temperature extremes, drought, or salt) or biotic stress (e.g., resistance to nematode, bacterial, or fungal pathogens), improved utilization of nutrients or water, modified lipid, carbohydrate, or protein composition, improved flavor or appearance, improved storage characteristics (e.g., resistance to bruising, browning, or softening), increased yield, altered morphology (e.g., floral architecture or color, plant height, branching, root structure). In an embodiment, a heterogeneous population of plant cells having a target gene edit or genome edit (or seedlings or plants grown or regenerated therefrom) is exposed to conditions permitting expression of the phenotype of interest; e.g., selection for herbicide resistance can include exposing the population of plant cells having a target gene edit or genome edit (or seedlings or plants grown or regenerated therefrom) to an amount of herbicide or other substance that inhibits growth or is toxic, allowing identification and selection of those resistant plant cells (or seedlings or plants) that survive treatment. Methods for obtaining regenerable plant structures and regenerating plants from plant cells or regenerable plant structures can be adapted from published procedures (Roest and Gilissen, Acta Bot. Neerl., 1989, 38(1), 1-23; Bhaskaran and Smith, Crop Sci. 30(6):1328-1337; Ikeuchi et al., Development, 2016, 143: 1442-1451). Methods for obtaining regenerable plant structures and regenerating plants from plant cells or regenerable plant structures can also be adapted from US Patent Application Publication No. 20170121722, which is incorporated herein by reference in its entirety and specifically with respect to such disclosure. Also provided are heterogeneous or homogeneous populations of such plants or parts thereof (e.g., seeds), succeeding generations or seeds of such plants grown or regenerated from the plant cells or plant protoplasts, having a target gene edit or genome edit. Additional related aspects include a hybrid plant provided by crossing a first plant grown or regenerated from a plant cell or plant protoplast having a target gene edit or genome edit and having at least one genetic or epigenetic modification, with a second plant, wherein the hybrid plant contains the genetic or epigenetic modification; also contemplated is seed produced by the hybrid plant. Also envisioned as related aspects are progeny seed and progeny plants, including hybrid seed and hybrid plants, having the regenerated plant as a parent or ancestor. The plant cells and derivative plants and seeds disclosed herein can be used for various purposes useful to the consumer or grower. In other embodiments, processed products are made from the INIR4 plant or its seeds, including: (a) maize seed meal (defatted or non-defatted); (b) extracted proteins, oils, sugars, and starches; (c) fermentation products; (d) animal feed or human food products (e.g., feed and food comprising maize seed meal (defatted or non-defatted) and other ingredients (e.g., other cereal grains, other seed meal, other protein meal, other oil, other starch, other sugar, a binder, a preservative, a humectant, a vitamin, and/or mineral; (e) a pharmaceutical; (f) raw or processed biomass (e.g., cellulosic and/or lignocellulosic material); and (g) various industrial products.

Embodiments

Various embodiments of the plants, genomes, methods, biological samples, and other compositions described herein are set forth in the following sets of numbered embodiments.

1a. A transgenic maize plant cell comprising an INIR4 transgenic locus comprising an originator guide RNA recognition site (OgRRS) in a first DNA junction polynucleotide of a DAS59122-7 transgenic locus and a cognate guide RNA recognition site (CgRRS) in a second DNA junction polynucleotide of the DAS59122-7 transgenic locus.

1b. A transgenic maize plant cell comprising an INIR4 transgenic locus comprising an insertion and/or substitution of DNA in a DNA junction polynucleotide of a DAS59122-7 transgenic locus with DNA comprising a cognate guide RNA recognition site (CgRRS) or a deletion in a 5' or 3' junction polynucleotide of a DAS59122-7 transgenic locus.

2. The transgenic maize plant cell of embodiment 1a or 1b, wherein said CgRRS comprises the DNA molecule set forth in SEQ ID NO: 8, 9, or 10; and/or wherein said DAS59122-7 transgenic locus is set forth in SEQ ID NO:1, is present in seed deposited at the ATCC under accession No. PTA-11384 is present in progeny thereof, is present in allelic variants thereof, or is present in other variants thereof.

3. The transgenic maize plant cell of embodiments 1a, 1b, or 2, wherein said INIR4 transgenic locus comprises the DNA molecule set forth in SEQ ID NO: 2, 3, 17, 23, 26, 27, or an allelic variant thereof.

4. A transgenic maize plant part comprising the maize plant cell of any one of embodiments 1a, 1b, 2, or 3, wherein said maize plant part is optionally a seed.

5. A transgenic maize plant comprising the maize plant cell of any one of embodiments 1a, 1b, 2, or 3.

6. A method for obtaining a bulked population of inbred seed comprising selfing the transgenic maize plant of embodiment 5 and harvesting seed comprising the INIR4 transgenic locus from the selfed maize plant.

7. A method of obtaining hybrid maize seed comprising crossing the transgenic maize plant of embodiment 5 to a second maize plant which is genetically distinct from the first maize plant and harvesting seed comprising the INIR4 transgenic locus from the cross.

8. A DNA molecule comprising SEQ ID NO: 2, 3, 8, 9, 10, 11, 16, 17, 23, 24, 26, 27, 28, or an allelic variant thereof.

9. A processed transgenic maize plant product comprising the DNA molecule of embodiment 8.

10. A biological sample containing the DNA molecule of embodiment 8.

11. A nucleic acid molecule adapted for detection of genomic DNA comprising the DNA molecule of embodiment 8, wherein said nucleic acid molecule optionally comprises a detectable label.

12. A method of detecting a maize plant cell comprising the INIR4 transgenic locus of any one of embodiments 1a, 1b, 2, or 3, comprising the step of detecting DNA molecule comprising SEQ ID NO: 2, 3, 8, 9, 10, 11, 16, 17, 23, 24, 26, 27, 28, or an allelic variant thereof.

13. A method of excising the INIR4 transgenic locus from the genome of the maize plant cell of any one of embodiments 1a, 1b, 2, or 3, comprising the steps of:
(a) contacting the INIR4 transgenic locus of the maize plant cell with: (i) an RNA dependent DNA endonuclease (RdDe); and (ii) a guide RNA (gRNA) capable of hybridizing to the guide RNA hybridization site of the OgRRS and the CgRRS; wherein the RdDe recognizes a OgRRS/gRNA and a CgRRS/gRNA hybridization complex; and,
(b) selecting a transgenic plant cell, transgenic plant part, or transgenic plant wherein the INIR4 transgenic locus flanked by the OgRRS and the CgRRS has been excised.

14. The method of embodiment 13, wherein the INIR4 transgenic locus of the maize plant cell comprises the CgRRS of SEQ ID NO: 8, 9, or 10 and the guide RNA comprises an RNA sequence encoded by SEQ ID NO: 13.

15. The method of embodiment 14, wherein the maize plant cell comprises the INIR4 transgenic locus of SEQ ID NO: 3, 17, 23, or an allelic variant thereof.

EXAMPLES

Example 1. Introduction of a CgRRS in a 5' Junction Polynucleotides of a DAS59122-7 Transgenic Locus Transgenic plant genomes containing one or more of the following transgenic loci (events) are contacted with:
(i) an ABE or CBE and guide RNAs which recognize the indicated target DNA sites (protospacer (guide RNA coding) plus PAM site) in the 5' or 3' junction polynucleotides of the event to introduce a CgRRS in the junction polynucleotide;
(ii) an RdDe and guide RNAs which recognize the indicated target DNA site (guide RNA coding plus PAM site) in the 5' or 3' junction polynucleotides of the event as well as a donor DNA template spanning the double stranded DNA break site in the junction polynucleotide to introduce a CgRRS in a junction polynucleotide.

Plant cells, callus, parts, or whole plants comprising the introduced CgRRS in the transgenic plant genome are selected.

TABLE 2

Examples of OgRRS and CgRRS in DAS59122-7

| CORN EVENT NAME | OgRRS | CgRRS |
|---|---|---|
| DAS59122-7 | (SEQ ID NO: 7; located in 3' junction polynucleotide of SEQ ID NO: 1) | (SEQ ID NO: 8; inserted into 5' junction polynucleotide) (SEQ ID NO: 9; inserted into 5' junction polynucleotide) (SEQ ID NO: 10; inserted into 5' junction polynucleotide) |

Example 2. Insertion of a CgRRS Element in the 5'-Junction of the DAS59122-7 Event Two plant gene expression vectors are prepared. Plant expression cassettes for expressing a bacteriophage lambda exonuclease, a bacteriophage lambda beta SSAP protein, and an E. coli SSB are constructed essentially as set forth in US Patent Application Publication 20200407754, which is incorporated herein by reference in its entirety. A DNA sequence encoding a tobacco c2 nuclear localization signal (NLS) is fused in-frame to the DNA sequences encoding the exonuclease, the bacteriophage lambda beta SSAP protein, and the E. coli SSB to provide a DNA sequence encoding the c2 NLS-Exo, c2 NLS lambda beta SSAP, and c2 NLS-SSB fusion proteins that are set forth in SEQ ID NO: 135, SEQ ID NO: 134, and SEQ ID NO: 133 of US Patent Application Publication 20200407754, respectively, and incorporated herein by example. DNA sequences encoding the c2 NLS-Exo, c2 NLS lambda beta SSAP, and c2NLS-SSB fusion proteins are operably linked to a OsUBI1, ZmUBI1, OsACT promoter and a OsUbi1, ZmUBI1, OsACT polyadenylation site respectively, to provide the exonuclease, SSAP, and SSB plant expression cassettes.

A DNA donor template sequence (SEQ ID NO: 11) that targets the 5'-T-DNA junction polynucleotide of the DAS59122-7 event (SEQ ID NO:1; FIG. 1) for HDR-mediated insertion of a base pair OgRRS sequence (SEQ ID NO: 7) that is identical to a Cas12a recognition site at the 3'-junction polynucleotide of the DAS59122-7 T-DNA insert is constructed. The DNA donor sequence includes a replacement template with desired insertion region (27 base pairs long) flanked on both sides by homology arms about 500 to about 600 bp in length. The homology arms match (i.e., are homologous to) gDNA (genomic DNA) regions flanking the target gDNA insertion site (SEQ ID NO: 12). The replacement template region comprising the donor DNA is flanked at each end by DNA sequences identical to the DAS59122-7 5'-T-DNA junction polynucleotide sequence recognized by a Cas12a RNA-guided nuclease and a gRNA (e.g., encoded by SEQ ID NO: 4).

A plant expression cassette that provides for expression of the RNA-guided sequence-specific Cas12a endonuclease is constructed. A plant expression cassette that provides for expression of a guide RNA (e.g., encoded by SEQ ID NO: 4) complementary to sequences adjacent to the insertion site is constructed. An *Agrobacterium* superbinary plasmid transformation vector containing a cassette that provides for the expression of a suitable plant selectable marker (e.g., a glyphosate tolerant EPSPS, a neomycin phosphotransferase (nptII), a hygromycin phosphotransferase (hptII), or a phosphomannose isomerase (pmi)) is constructed. Once the cassettes, donor sequence and *Agrobacterium* superbinary plasmid transformation vector are constructed, they are combined to generate two maize transformation plasmids.

A maize transformation plasmid is constructed with the selectable marker cassette, the RNA-guided sequence-specific endonuclease cassette, the guide RNA cassette, and the DAS59122-7 5'-T_DNA junction sequence DNA donor sequence into the *Agrobacterium* superbinary plasmid transformation vector (the control vector).

A maize transformation plasmid is constructed with the selectable marker cassette, the RNA-guided sequence-specific endonuclease cassette, the guide RNA cassette, the SSB cassette, the lambda beta SSAP cassette, the Exo cassette, and the DAS59122-7 5'-T_DNA junction sequence donor DNA template sequence (e.g., SEQ ID NO: 11) into the *Agrobacterium* superbinary plasmid transformation vector (the lambda red vector).

All constructs are transformed into *Agrobacterium* strain LBA4404.

Maize transformations are performed based on published methods (Ishida et. al, Nature Protocols 2007; 2, 1614-1621). Briefly, immature embryos from inbred line GIBE0104, approximately 1.8-2.2 mm in size, are isolated from surface sterilized ears 10-14 days after pollination. Embryos are placed in an *Agrobacterium* suspension made with infection medium at a concentration of OD 600=1.0. Acetosyringone (200 μM) is added to the infection medium at the time of use. Embryos and *Agrobacterium* are placed on a rocker shaker at slow speed for 15 minutes. Embryos are then poured onto the surface of a plate of co-culture medium. Excess liquid media is removed by tilting the plate and drawing off all liquid with a pipette. Embryos are flipped as necessary to maintain a scutelum up orientation. Co-culture plates are placed in a box with a lid and cultured in the dark at 22° C. for 3 days. Embryos are then transferred to resting medium, maintaining the scutellum up orientation. Embryos remain on resting medium for 7 days at 27-28° C. Embryos that produced callus are transferred to Selection 1 medium with a suitable concentration of the selection agent for the selectable marker gene selected and cultured for an additional, suitable time period (e.g. 7 days). In some instances, glyphosate is used as the selection agent for a glyphosate tolerant EPSPS selectable marker (e.g., as in U.S. Pat. No. 8,212,113, incorporated herein by reference in its entirety). In some instances, kanamycin, paromomycin, or G418 is used as the selection agent for a nptII selectable marker (e.g., as in U.S. Pat. No. 8,450,561, incorporated herein by reference in its entirety). In some instances, hygromycin is used as the selection agent for an hptII selectable marker (e.g., as in U.S. Pat. No. 7,064,248, incorporated herein by reference in its entirety). In some instances, media comprising mannose as a sole carbon source is used as the selection agent for a pmi selectable marker (as in U.S. Pat. No. 8,455,720, incorporated herein by reference in its entirety). Callused embryos are placed on Selection 2 medium with a suitable concentration of the selection agent and cultured for 14 days at 27-28° C. Growing calli resistant to the selection agent are transferred to Pre-Regeneration media with a suitable concentration of the selection agent to initiate shoot development. Calli remained on Pre-Regeneration media for a suitable time period (e.g., 7 days). Calli beginning to initiate shoots are transferred to Regeneration medium with a suitable concentration of the selection agent in Phytatrays and cultured in light at 27-28° C. Shoots that reached the top of the Phytatray with intact roots are isolated into Shoot Elongation medium prior to transplant into soil and gradual acclimatization to greenhouse conditions.

When a sufficient amount of viable tissue is obtained, it can be screened for insertion at the DAS59122-7 junction sequence, using a PCR-based approach. The PCR primer on the 5'-end is set forth in SEQ ID NO: 14). The PCR primer on the 3'-end is set forth in SEQ ID NO: 15). The above primers that flank donor DNA homology arms are used to amplify the DAS59122-7 5'-junction polynucleotide sequence. The correct donor sequence insertion will produce a bp product. A unique DNA fragment comprising the CgRRS in the DAS59122-7 5' junction polynucleotide is set forth in SEQ ID NO: 16. Amplicons can be sequenced directly using an amplicon sequencing approach or ligated to a convenient plasmid vector for Sanger sequencing. Those plants in which the DAS59122-7 junction sequence now contains the intended Cas12a recognition sequence are selected and grown to maturity. The T-DNA encoding the Cas12a reagents can be segregated away from the modified junction sequence in a subsequent generation. The resultant INIR4-3 transgenic locus (SEQ ID NO: 17) comprising the CgRRS and OgRRS (e.g., which each comprise SEQ ID NO: 7) can be excised using Cas12a and a suitable gRNA (e.g., a gRNA comprising RNA encoded by SEQ ID NO: 13) which hybridizes to DNA comprising SEQ ID NO: 7 at both the OgRRS and the CgRRS.

The breadth and scope of the present disclosure should not be limited by any of the above-described embodiments.

What is claimed is:

1. A transgenic maize plant cell comprising an INIR4 transgenic locus comprising an originator guide RNA recognition site (OgRRS) in a first DNA junction polynucleotide of a DAS59122-7 transgenic locus and a cognate guide RNA recognition site (CgRRS) in a second DNA junction polynucleotide of the DAS59122-7 transgenic locus, wherein said INIR4 transgenic locus comprises the DNA molecule set forth in SEQ ID NO: 27 or an allelic variant thereof.

2. The transgenic maize plant cell of claim 1, wherein said INIR4 transgenic locus comprises the DNA molecule set forth in SEQ ID NO: 27.

3. A transgenic maize plant part comprising the maize plant cell of claim 1.

4. The transgenic maize plant part of claim 3, wherein said maize plant part is a seed.

5. A transgenic maize plant comprising the maize plant cell of claim 1.

6. A method for obtaining a bulked population of inbred seed comprising selfing the transgenic maize plant of claim 5 and harvesting seed comprising the INIR4 transgenic locus from the selfed maize plant.

7. A method of obtaining hybrid maize seed comprising crossing the transgenic maize plant of claim 5 to a second maize plant which is genetically distinct from the first maize plant and harvesting seed comprising the INIR4 transgenic locus from the cross.

8. A DNA molecule comprising SEQ ID NO: 27.

9. A processed transgenic maize plant product comprising the DNA molecule of claim 8.

10. A biological sample containing the DNA molecule of claim 8.

11. A method of detecting a maize plant cell comprising the INIR4 transgenic locus of claim 1, comprising the step of detecting a DNA molecule comprising SEQ ID NO: 10.

12. A method of excising the INIR4 transgenic locus from the genome of the maize plant cell of claim 1, comprising the steps of:

(a) contacting the INIR4 transgenic locus of the plant cell with: (i) a Cas12 RNA dependent DNA endonuclease (RdDe); and (ii) a guide RNA (gRNA) capable of hybridizing to the guide RNA hybridization site of the OgRRS and the CgRRS of SEQ ID NO: 27; wherein the Cas12 RdDe recognizes a OgRRS/gRNA and a CgRRS/gRNA hybridization complex; and, (b) selecting a transgenic plant cell, transgenic plant part, or transgenic plant wherein the INIR4 transgenic locus flanked by the OgRRS and the CgRRS has been excised.

13. The method of claim 12, wherein the guide RNA comprises an RNA sequence encoded by SEQ ID NO: 13.

* * * * *

SEQUENCE LISTING

```
Sequence total quantity: 28
SEQ ID NO: 1              moltype = DNA   length = 11922
FEATURE                   Location/Qualifiers
source                    1..11922
                          mol_type = other DNA
                          organism = synthetic construct
SEQUENCE: 1
ctgagcgcac aacagcgagt cgcatggcac cggacgacat gagcgagatt tagatcggag    60
ggtgcggaca tggggcaacc tgcgcagcta acgcagggat ccacacgacc accaacgaag   120
ccaagcccgg gcacgtcccc aggcaggttg ggccctggtt ccaccagcgg atgcatgcag   180
tgaagcgggg acggagagac aagccgaggg cgcgggtggg aatggcgtcc gggaggacga   240
gtggaggaga agaatctaga ggcatcgaga ttcgagaagc cgacggagac aagattcgtg   300
tgggggggaga caaaccgcgg ggctgagcgc cgttgatatg ggatcagacg gtgtggataa   360
aaaaagtgac gttgatagaa cgtctggcca gtgaaaaaac aaaacaactc caacaaaata   420
cttttaaaagc tcttatacce taaatgtagg ggatcaaaca cgtctctaca ctatttagca   480
gcgtcctcta aatgatcctc taaatttaga gaacgctact agattctcta tatatagttt   540
ctctaaacga tcttttatcc atttaaatac tttaaataac cggtttaaca aaactaaaat   600
atatacaata catttgagag tatgacaaat acgtatgtat aaaaataaaa aataaaaataa   660
tgtattagtc tactttgaat cttcttttct tcataaataa atgatgtata gctctcatgt   720
gcgttgagaa aaaagttaga gctagacgtt taatgtgtag tgacagtctt cgacgaaatc   780
tccctaatga gatgaattac tggaggttcc atcagaaagt ccctgaaaa gaggcattta   840
tttagtttag tcagcaattt ctgggaacac aaatattctt ttgttatcac cactattaaa   900
aatctatggt tataacttat aataacatga aaaaataatt tagcatccca tatatataaa   960
aactgaagga agccatatat actaacataa gttaggagaa actaagaagg ttgtgcaaag  1020
cttgcactgc tccaaaatac tgcaaacaac cactctcctc taccaaccaa agaaactcat  1080
gtactccctc cgttcttttt tatttgtcgc attttagttt aaaaatgaac tagcagtcga  1140
caaatattcg agaacagata tagtatatac taacataact taggagatac taagaaagtt  1200
gcgcagagct ttcactgttc caaattactg caaagcctct ccctctgcc agtacatcta  1260
cgagatgttt cagttaaaca aagattcaga caagtgatga gccacttctt gtcatagatt  1320
gtgtggtcaa ccaacccatt gatgccacgg ttttgtgca tccatgcttt tgtattaaaa  1380
catcagttat gtttaccatg tccgatatgc tctacataat gacaatcaac ttggtgttca  1440
ttatatttac aatgttagga atttcaatag ctacgaacac tcaatagaa gtgccttgt  1500
gggatcacct taatgtgttg ttgatgtaag gagaagaatc ttaatttact cttgctaaat  1560
ttgaactaca caaaccact gcactgagga ttgtcctaat aaaattactgc tcatacacgt  1620
tagcatctgt tcagatactg agctaatccc taggattaaa ggatttgtaa aagatatgcc  1680
caatcattca ttttagttat ttatttctta gttatccact tgaagattta catacatttg  1740
aaataaattt cttagaggta aagtgaaaat cagttatta aatacatttt agttatttat  1800
tttcttcttt ttcctaattt ttccttgtat ttgaagtctg aaaagataac tttgcccta  1860
tacatatttt atcttctacg tacgcatctg aacaacgtct ctttgtccc tgatcgtgca  1920
gcaattagtg ctatgaatcg cgtttaagcg ctgcaaaatc atggctgggg cttcgtcctc  1980
gagtcgtcct gctgctcgat gtcacctcga gtcccgcacc gacctcagtg cttgttcttg  2040
ttggagccac ctctctcgga cgatcgccaa agacggataa ggccgaagcc gtcacttcag  2100
accgcgctca tgcgccgtag cagactccta catagcaggg ccaggtgatg tggaccttg  2160
caagtttagg attggaacca gcgaccagaa tccacaagt tggagcaaac gaccaaaat  2220
tcacaaggat tggcggctga cattgccagc gcgggatcgc atgcggcggc ggcggccggg  2280
gcgagcacgg gagcaggcga cagtcgagct ccattggaac gtagaaatac ttaagggcaa  2340
ggtctccaaa tacttgaaaa aataggaaaa agaagaaaat acatgaaatg atattgaaat  2400
caattggaag atgttatgaa tcttgtttt gcaaagcgaa cgattcagat ggcaaaacta  2460
tgaatctttt tgtttgaagt cccaaatata aaatttctc gtactcacca acattggtgc  2520
gcacctgtga ttggctcata aaaattcttg gagggacgga agaaagagtg aagggataag  2580
caagtaaaag cgctcaaaca ctgatagttt aaactgaagg cgggaaacga caatctgatc  2640
atgagcggag aattaaggga gtcacgttat gaccccccgc gatgacgcgg gacaagccgt  2700
tttacgtttg gaactgacag aaccgcaacg ttgaaggagc cactcagcaa gcttactagt  2760
agcgctgttt aaacgctctt caactggaag agcggttacc cggaccgaag cttgcatgcc  2820
tgcagtgcag cgtgacccgg tcgtgcccct ctctagagat aatgagcatt gcatgtctaa  2880
gttataaaaa attaccacat attttttttg tcacacttgt ttgaagtgca gtttatctat  2940
ctttatacat atatttaaac tttactctac gaataataat atctatagta ctacaataat  3000
atcagtgttt tagagaatca tataaatgaa cagttagaca tggtctaaag gacaattgag  3060
tattttgaca acaggactct acagttttat ctttttagtg tgcatgtgtt ctcctttttt  3120
tttgcaaata gcttcaccta tataatactt catccatttt attagtacat ccatttaggg  3180
tttagggtta atggttttta tagactaatt ttttagtac atctattta ttctatttta  3240
gcctctaaat taagaaaact aaaactctat tttagtttt ttatttaata atttagatat  3300
aaaatgaat aaaataaagt gactaaaaat taaacaaata ccctttaaga aattaaaaa  3360
actaaggaaa catttttctt gtttcgagta gataatgcca gcctgttaaa cgccgtcgac  3420
gagtctaacg gacaccaacc agcgaaccag tcgtcgtca tcggccaag cgaaggcagac  3480
ggcacggcat ctctgtcgct gcctctggac ccctctcgag agttccgctc caccgttgga  3540
cttgctccgc tgtcggcatc cagaaattgc gtggcggagc ggcagacgtg agccggcacg  3600
gcaggcggcc tcctcctcct ctcacggcac cggcagctac gggggattcc tttcccaccg  3660
ctccttcgct ttccttcct cgcccgccgt aataaataga cacccccctcc acaccctctt  3720
tccccaacct cgtgttgtc ggagcgcaca cacacacaac cagatctccc ccaaatccac  3780
ccgtcggcac ctccgcttca aggtacgcg ctcgtcctcc ccccccccc ctctctacct  3840
tctctagatc ggcgttccgg tccatggtta gggcccggta gttctacttc tgttcatgtt  3900
tgtgttagat ccgtgtttgt gttagatccg tgctgctagc gtcgtacac ggatcgacc  3960
tgtacgtcag acacgttctg attgctaact tgccagtgtt tctctttggg gaatcctagt  4020
atggctctag ccgttccgca gacgggatcg atttcatgat ttttttttgtt tcgttgcata  4080
gggtttggtt tgcctttc ctttatttca atatatgccg tgcacttgtt tgtcgggtca  4140
tctttttcatg ctttttttg tcttggttgt gatgatgtgg tctggttggg cggtcgttct  4200
agatcggagt agaattctgt tcaaaactac ctggtggatt tattaatttt ggatctgtat  4260
```

```
gtgtgtgcca tacatattca tagttacgaa ttgaagatga tggatggaaa tatcgatcta   4320
ggataggtat acatgttgat gcgggtttta ctgatgcata tacagagatg cttttttgttc  4380
gcttggttgt gatgatgtgg tgtggttggg cggtcgttca ttcgttctag atcggagtag   4440
aatactgttt caaactacct ggtgtattta ttaattttgg aactgtatgt gtgtgtcata   4500
catcttcata gttacgagtt taagatggat ggaaatatcg atgtaggata ggtatacatg   4560
ttgatgtggg ttttactgat gcatatacat gatggcatat gcagcatcta ttcatatgct   4620
ctaaccttga gtacctatct attataataa acaagtatgt tttataatta ttttgatctt   4680
gatatacttg gatgatggca tatgcagcag ctatatgtgg atttttttag ccctgccttc   4740
atacgctatt tatttgcttg gtactgtttc ttttgtcgat gctcaccctg ttgtttggtg   4800
ttacttctgc aggtcgactc tagaggatcc acacgacacc atgtccgccc gcgaggtcga   4860
catcgacgtg aacaacaaga ccggccacac cctccagctg gaggacaaga ccaagctcga   4920
cggcggcagg tggcgcacct ccccgaccaa cgtggccaac gaccagatca agaccttcgt   4980
ggccgaatcc aacggcttca tgaccggcac cgagggcacc atctactact caattaatgg   5040
cgaggccgag atcagcctct acttcgacaa cccgttcgcc ggctccaaca aatacgacgg   5100
ccactccaac aagtcccagt acgagatcat caccagggc ggctccggca accagtccca   5160
cgtgacctac accatccaga ccacctcctc ccgctacggc cacaagtcct gagtcatgag   5220
tcatgagtca gttaacctag acttgtccat cttctggatt ggccaactta ttaatgtat    5280
gaaataaaag gatgcacaca tagtgacatg ctaatcacta taatgtgggc atcaaagttg   5340
tgtgttatgt gtaattacta gttatctgaa taaaagagaa agagatcatc catatttctt   5400
atcctaaatg aatgtcacgt gtctttataa ttctttgatg aaccagatgc atttcattaa   5460
ccaaatccat atacatataa atattaatca tatataatta atatcaattg ggttagcaaa   5520
acaaatctag tctaggtgtg ttttgcgaat gcggccgagg accgaattgg ggatctgcat   5580
gaaagaaact gtcgcactgc tgaaccgcac cttgtcactt tcatcgaaca cgacctgtgc   5640
ccaagatgac ggtgctgcgg tctaagtgag gctgaattgc cttggacaga agcggactcc   5700
ctacaattag ttaggccaaa cggtgcatcc atgtgtagct ccgggctcgg gctgtatcgc   5760
catctgcaat agcatccatg gagctcgttc catgtagttg gagatgaacc aatgatcggc   5820
cgtgtggacg tatgttcctg tgtactccga tagtagagta cgtgttagct ctttcatggt   5880
gcaagtgaaa tttgtgttgg tttaattacc cctacgttag ttgcgggaca ggagacacat   5940
catgaattta aaggcgatga tgtcctctcc tgtaatgtta ttcttttgat gtgatgaatc   6000
aaaatgtcat ataaaacatt tgttgctctt tagttaggcc tgatcgtaga acgaaatgct   6060
cgtgtagcgg ggctacgagc ctatgacgca ataacactgg tttgccggcc cggagtcgct   6120
tgacaaaaaa aagcatgtta agtttattta caattcaaaa cctaacatat tatattccct   6180
caaagcaggt tcacgatcac acctgtacct aaaaaaaaca tgaagaatat attactccat   6240
tattatgaga tgaaccactt ggcaagagtg gtaagctata taaaaaaatg aacattatta   6300
cgagatgtta tatgccatta tattgattcg aagatatatg tttctttctc ccacgggcac   6360
ctaacggata catgataagg ccaaggcaga tcacgggaaa ttattcgaat acatgttacg   6420
ccctattgcc ggaaaaaaaa tgcagggcag gtgttggccg tagcgattta agcacttaag   6480
ctggaggttg ccacacttgg atgcaagcgt ctgacccttc taaaacatcg gcggctttgt   6540
ccgtatccgt atcccctatc cgacatctag ctggccacac gacggggctg ggcagatcgt   6600
ggatgccggg tcgacgtcga tcgtcagcca tcatagacca atcgaccatc tgttatggat   6660
gcttgctagc tagactagtc agacataaaa ttttggatact ttctcccaac tgggagacgg   6720
ggactgatgt gcagctgcac gtgagctaaa ttttttccta taaatatgca tgaaatactg   6780
cattatcttg ccacagccac tgccacagcc agataacaag tgcagctggt agcacgcaac   6840
gcatagctct ggacttgtag ctaggtagcc aaccggatcc acacgacacc atgtctgaca   6900
ccaacaaggt gtacgagatc agcaaccacg ccaacggcct ctacgccgcc acctacctct   6960
ccctcgacga ctccggcgtg tccctcatga acaagaacga cgacgacatc gacgactaca   7020
acctcaagtg gttcctcttc ccgatcgacg acgaccagta catcatcacc tcctacgccg   7080
ccaacaactg caaggtgtgg aacgtgaaca acgacaagat taatgtgtca acctactcct   7140
ccaccaactc catccagaag tggcagatca aggccaacgg ctcctcctac gtgatccagt   7200
ccgacaacgg caaggtgctc accgccggca ccggccaggc cctcggcctc atccgcctca   7260
ccgacggtc ctccaacaac ccgaaccagc aatggaacct gacgtccgtg cagaccatcc   7320
agctcccgca gaagccgatc atcgacacca agctcaagga ctacccgaag tactcccga   7380
ccggcaacat cgacaacggc acctccccgc agctcatggg ctggaccctc gtgccgtgca   7440
tcatggtgaa cgaccgaac atcgacaaga cacccagat caagaccacc ccgtactaca   7500
tcctcaagaa gtaccagtac tggcagaggg ccgtggcgtc ccgtggggtc ctccgcccgc   7560
acgagaagaa gtcctacacc tacgagtggg gcaccgagat cgaccagacg accaccatca   7620
tcaacaccct cggcttccag atcaacatcg acagcggcat gaagttcgac atcccggagg   7680
tgggcggcgg taccgacgag atcaagaccc agctcaacga ggagctcaag atcgagtatt   7740
cacatcgagac gaagatcatg gagaagtacc aggagcagtc cgagatcgac aacccgaccg   7800
accagtccat gaactccatc ggcttcctca ccatccacctc cctgagctc taccgctaca   7860
acggctccga gatccgcatc atgcagatcc agacctccga caacgacacc tacaacgtga   7920
cctcctaccc gaaccaccag caggccctgc tgctgctgac caaccactcc tacgaggagg   7980
tggaggagat caccaacatc ccgaagtcca ccctcaagaa gctcaagaag tactacttct   8040
gagtcatgag tcatgagtca gttaacctag acttgtccat cttctggatt ggccaactta   8100
attaatgtat gaaataaaag gatgcacaca tagtgacatg ctaatcacta taatgtgggc   8160
atcaaagttg tgtgttatgt gtaattacta gttatctgaa taaaagagaa agagatcatc   8220
catatttctt atcctaaatg aatgtcacgt gtctttataa ttctttgatg aaccagatgc   8280
atttcattaa ccaaatccat atacatataa atattaatca tatataatta atatcaattg   8340
ggttagcaaa acaaatctag tctaggtgtg ttttgcgaat tcccatggag tcaaagattc   8400
aaatagagga cctaacagaa ctcgccgtaa agactggcga acagttcata cagagtctct   8460
tacgactcaa tgcaagaag aaaatcttcg tcaacatggt ggagcacgac acgcttgtct   8520
actccaaaaa tatcaaagat acagtctcag aagaccaaag gcaattgag acttttcaac   8580
aaagggtaat atccggaaac ctcctcggat tccattgccc agctatctgt cactttattg   8640
tgaagatagt ggaaaaggaa ggtggctcct acaaatgcca tcattgcgat aaaggaaagg   8700
ccatcgttga agatgcctct gccgacagtg gtcccaaaga tggacccca cccacgagga   8760
gcatcgtgga aaaagaagac gttccaacca cgtcttcaaa gcaagtggat tgatgtgata   8820
tctccactga cgtaagggat gacgcacaat cccactatcc ttcgcaagac ccttcctcta   8880
tataaggaag ttcatttcat ttggagagga cagggtaccc ggggatccac catgtctccg   8940
gagaggagac cagttgagat taggccagct acagcagctg atatggccgc ggtttgtgat   9000
```

```
atcgttaacc attacattga gacgtctaca gtgaacttta ggacagagcc acaaacacca      9060
caagagtgga ttgatgatct agagaggttg caagatagat acccttggtt ggttgctgag      9120
gttgagggtg ttgtggctgg tattgcttac gctgggccct ggaaggctag gaacgcttac      9180
gattggacag ttgagagtac tgtttacgtg tcacataggc atcaaaggtt gggcctagga      9240
tccacattgt acacacattt gcttaagtct atggaggcgc aaggttttaa gtctgtggtt      9300
gctgttatag gccttccaaa cgatccatct gttaggttgc atgaggcttt gggatacaca      9360
gcccgggta cattgcgcgc agctggatac aagcatggtg gatggcatga tgttggtttt      9420
tggcaaaggg attttgagtt gccagctcct ccaaggccag ttaggccagt tacccagatc      9480
tgagtcgacc tgcaggcatg cccgctgaaa tcaccagtct ctctctacaa atctatctct      9540
ctctataata atgtgtgagt agttcccaga taagggaatt aggggttctta taggggtttcg      9600
ctcatgtgtt gagcatataa gaaacccttta gtatgtattt gtatttgtaa aatacttcta      9660
tcaataaaat ttctaattcc taaaaccaaa atccagggcg agctcggtac ccggggatcc      9720
tctagagtcg acctgcaggc atgcccgcgg atatcgatgg ccccggccg aagcttcggt      9780
ccggggccatc gtggcctctt gctcttcagg atgaagagct atgtttaaac gtgcaagcgc      9840
tcaattcgcc ctatagtgag tcgtattaca atcgtacgca attcagtaca ttaaaaacgt      9900
ccgcaatgtg ttattaagtt gtctaagcgt caattttttcc cttctatggt cccgtttgtt      9960
tatcctctaa attatataat ccagcttaaa taagttaaga gacaaacaaa caacacagat     10020
tattaaatag attatgtaat agattatgta atccataagt agaatatcag agaatatcag     10080
gtgcttatat aatctatgag ctcgattata taatcttaaa agaaaacaaa cagagccct     10140
ataaaagggg gtcaagtgga cacttggtca ctcatttaat ccctccctct cctcttttat     10200
ccctcttttt ggtgtattca ccaatagtgg tgtgcacctg tgattggctc gtaaaaattc     10260
ttggacggat ggaagagtga agagataagc aagtcaaaga aagtaacaa cgaagcttca     10320
tcagctacaa atttggccc aactggttgc accagcacca aacttacgta tacatgatta     10380
tctctgtttc cctcatttcg aagaaaaaaa cgggtttcaa aacccactgc tttcaggagt     10440
aaaaaaagat aataatctga aacattgctt ccaccttggc ccttatttgg ttacgttgca     10500
attcaccca atccacatgt ggattgagat ggattgcagt gtagctagac aaaccctag     10560
gccctgtttg cataggaata caccaggaat tattccagct aatcaaaatt tatataaaatg     10620
agagaaacaa ttcggatagg aattgttcca ggacttcatt ctgcagtaac cgaacggccc     10680
cttaatccac cccaatacac gtggattgga gtggattgag gtacagccaa acaaggccta     10740
agtgcagatc aaataaatca cccgtcatat tcttctacct acaaaaacag caataaacac     10800
ctgaatgaag ttctaatttg cacagtgtag gtaggatgaa aatagttacc tcctcatggt     10860
cagtaactct tggcacacaa cttcacatgt aatcgatgta ccactggct cttgcctgaa     10920
acccaataca tctttagcat aagaataata ttatgatggc aaggcatgat caccagcact     10980
cctttattgt ttagtaagtc tatcactccc caaaacaatt caaatgaaca gagatgcatt     11040
gccccccaatg aattctattt caattagccg gaaaattcta cttcatcaga agcatccaaa     11100
ttgccagcat ccctactaga ctgaccatga ccaggctgcc gcagatgcct ctttttctgt     11160
cctctcctct ttgccttgag tttctcttca agatccctca ccccacgtct cttatacatc     11220
ttaaagctaa catgtctctc ctccgccatc ttcctaacct tctcagtaat ctcagcagca     11280
atctgacggt tgtacaactt cttcagcccc ttcatcaact tgcaaatgt tcaggctgt     11340
ggcatcagtc ctgcctctag catgtctaag caatacaggc aggcctcctt gacatgttc     11400
ttcgcaaaca gtgcatgaat ccagatagtc catgcactca cattgagctc acagcctttg     11460
ctcacaatac atttccaaac atcctttgca agctcaagtt tctcatctct gaccaacgca     11520
ttgaggaggt ccttcagcac cccatattgc ggtaccacaa agagccccct ccaaccatg     11580
tcttaaaat aactacatgc ctcaatcagc aaacccctgcc caacaaggcc actcaccacg     11640
atagcaaatg tatcgaccac aggactgagc ccagcacttt ccatctcatt ccacaatgtc     11700
atggcttgct tggtctcccc aagcctgcag gccaaccgaa tcaccacatt gtatatcttg     11760
agatctggtg gacaccggca ctcccgccatc ctctccataa gctccaagca ctcctcaagc     11820
tgctccttct tctcgtgtgc tacaaagaaa ccatggtaca cggcagcgtc caccccgcagg     11880
ccatccctcg acatagcatc caagaactcg tacccctggg at                          11922

SEQ ID NO: 2         moltype = DNA   length = 11915
FEATURE              Location/Qualifiers
source               1..11915
                     mol_type = other DNA
                     organism = synthetic construct
SEQUENCE: 2
ctgagcgcac aacagcgagt cgcatggcac cggacgacat gagcgagatt tagatcggag      60
ggtgcggaca tggggcaacc tgcgcagcta acgcagggat ccacacgacc accaacgaag     120
ccaagcccgg gcacgtcccc aggcaggttg ggccctggtt ccaccagcgg atgcatgcag     180
tgaagcgaac acggagagac aagccgaggg cgcgggtggg aatggcgtcc gggaggacga     240
gtggaggaga agaatctaga ggcatcgaga ttcgagaagc cgacggagac aagattcgtg     300
tgggggggaga caaccgcgg ggctgagcgc cgttgatatg ggatcagacg tgtgtggaaa     360
aaaaagtgac gttgatagaa cgtctggcca gtgaaaaaac aaaacaactc caacaaaata     420
ctttaaaagc tcttataccc taaatgtagg ggatcaacaa cgtctctaca ctatttagca     480
gcgtcctcta aatgatcctc taaatttaga gaacgctact agattctcta tatatagttt     540
ctctaaacga tctttttatcc atttaaatac tttaaataac cggttaaca aaactaaaat     600
atatacaata catttgagag tatgacaaat acgtatgtat aaaaataaaa aataaataa     660
tgtattagtc tactttgaat cttctttttct tcataatata atgatgtata gctctcatgt     720
gcgttgagaa aaaagttaga gctagacgtt taatgtgtag tgacagtctt cgacgaaatc     780
tccctaatga gatgaattac tggaggttcc atcagaaagt cccctgaaaa gaggcattta     840
tttagtttag tcagcaattt ctgggaacac aaatattctt ttgttatcac cactattaaa     900
aatctatggt tataacttat aataacatga aaaataatt tagcatccca tatatataaa     960
aactgaagga agccatatat actaacataa gttaggagaa actaagaagg ttgtgcaaag    1020
cttgcactgc tccaaaatac tgcaaacaac cactctccta taccaaccaa agaaactcat    1080
gtactccctc cgttcttttt tatttgtcgc attttagttt aaaaatgaac tagcagtcga    1140
caaatattcg agaacagata tagtatatac taacataact taggagatac taagaaagtt    1200
gcgcagagct ttcactgttc caaattactg caaagcctct cccctctgcc agtacatcta    1260
cgagatgttt cagttaaaca aagattcaga caagtgatga gccactcttc gtcatagatt    1320
gtgtggtcaa ccaaccatt gatgccacgg ttttgtgca tccatgcttt tgtattaaaa    1380
```

```
catcagttat gtttaccatg tccgatatgc tctacataat gacaatcaac ttggtgttca    1440
ttatatttac aatgttagga atttcaatag ctacgaacac ttcaatagaa gtgcctttgt    1500
gggatcacct taatgtgttg ttgatgtaag gagaagaatc ttaatttact cttgctaaat    1560
ttgaactaca caaaaccact gcactgagga ttgtcctaat aaattactgc tcatacacgt    1620
tagcatctgt tcagatactg agctaatccc taggattaaa ggatttgtaa aagatatgcc    1680
caatcattca ttttagttat ttatttctta gttatccact tgaagattta catacatttg    1740
aaataaattt cttagaggta aagtgaaaat cagttattta aatacatttt agttatttat    1800
tttcttcttt ttcctaattt ttccttgtat ttgaagtctg aaaagataac tttgccctta    1860
tacatatttt atcttctacg tacgcatctg aacaacgtct ctttgtcccc tgatcgtgca    1920
gcaattagtg ctatgaatcg cgtttaagcg ctgcaaaatc atggctgggg cttcgtcctc    1980
gagtcgtcct gctgctcgat gtcacctcga gtcccgcacc gacctcagtg cttgttcttg    2040
ttggagccac ctctctcgga cgatcgccaa agacggataa ggccgaagcc gtcacttcag    2100
accgcgctca tgcgccgtag cagactccta catagcaggg ccagggtatg tggacctttg    2160
caagtttagg attggaacca gcgaccagaa tccacaagat tggagcaaac gaccaaaaat    2220
tcacaaggat tggcggctga cattgccagc gcgggatcgc atgcggcggc ggcggccggg    2280
gcgagcacgg gagcaggcga cagtcgagct ccattggaac gtagaaatac ttaagggcaa    2340
ggtctccaaa tacttgaaaa aataggaaaa agaagaaaat acatgaaatg atattgaaat    2400
caattggaag atgttatgaa tcttgttttt gcaaagcgaa cgattcagat ggcaaaacta    2460
tgaatctttt tgtttgaagt cccaaatata aaattttctc gtactcacca acattggtgc    2520
gcacctgtga ttggctcata aaaattcttg gagggacgga agaaagagtg aagggataag    2580
caagtctcaa acactgatag tttaaactga aggcgggaaa cgacaatctg atcatgagcg    2640
gagaattaag ggagtcacgt tatgacccc gccgatgacg ggacaacgc cgtttttacgt    2700
ttggaactga cagaaccgca acgttgaagg agccactcag caagcttact agtagcgctg    2760
tttaaacgct cttcaactgg aagagcggtt acccggaccg aagcttgcat gcctgcagtg    2820
cagcgtgacc cggtcgtgcc cctctctaga gataatgagc attgcatgtc taagttataa    2880
aaaattacca catattttt ttgtcacact tgtttgaatg gcagtttatc tatctttata    2940
catatattta aactttactc tacgaataat ataatctata gtactacaat aatatcagtg    3000
ttttagagaa tcatataaat gaacagttag acatggtcta aaggacaatt gagtattttg    3060
acaacggac tctacagttt tatcttttta gtgtgcatgt gttctccttt ttttttgcaa    3120
atagctccac ctatataata cttcatccat tttattagta catccattta gggttttaggg    3180
ttaatggttt ttatagacta attttttag tacatctatt ttattctatt ttagcctcta    3240
aattaagaaa actaaaactc tattttagtt tttttattta ataatttaga tataaaatag    3300
aataaaataa agtgactaaa aattaaacaa atacccttta agaaattaaa aaaactaagg    3360
aaacattttt cttgtttcga gtagataatg ccagcctgtt aaacgccgtc gacgagtcta    3420
acggacacca accagcgaac cagcagcgtc gcgtcgggcc aagcagacga gacggcacgg    3480
catctctgtc gctgcctctg gaccctctc gagagttccg ctccaccgtt ggacttgctc    3540
cgctgtcggc atccagaaat tgcgtggcgg agcggcagac gtgagccggc acggcaggcg    3600
gcctcctcct cctctcacgg caccggcagc tacggggat tcctttccca ccgctccttc    3660
gctttccctt cctcgcccgc cgtaataaat agacacccc tccacaccct ctttccccaa    3720
cctcgtgttg ttcggagcgc acacacacac aaccagatct cccccaaatc cacccgtcgg    3780
cacctccgct tcaaggtacg ccgctcgtcc tccccccccc cccctctcta ccttctctag    3840
atcggcgttc cggtccatgg ttagggcccg gtagttctac ttctgttcat gtttgtgtta    3900
gatccgtgtt tgtgttagat ccgtgctgct agcgttcgta cacggatgcg acctgctagt    3960
cagacacgtt ctgattgcta acttgccagt gtttctcttt ggggaatcct gggatggctc    4020
tagccgttcc gcagacggga tcgatttcat gattttttt gttcgttgc ataggggtttg    4080
gtttgccctt ttcctttatt tcaatatatg ccgtgcactt gtttgtcggg tcatctttc    4140
atgcttttt ttgtcttggt tgtgatgatg tggtctggtt gggcggtcgt tctagatccgg    4200
agtagaattc tgtttcaaac tacctggtgg atttattaat tttggatctg tatgtgtgtg    4260
ccatacatat tcatagttac gaattggaaga tgatggatgg aaatatcgat ctaggatagg    4320
tatacatgtt gatgcgggtt ttactgatgc atatacagag atgcttttg ttcgcttggt    4380
tgtgatgatg tggtgtggtt gggcggtcgt tcattcgttc tagatcggag tagaatactg    4440
tttcaaacta cctggtgtat ttattaattt tggaactgta tgtgtgtgtc atacatcttc    4500
atagttacga gtttaagatg gatggaaata tcgatgtagg ataggtatac atgttgatgt    4560
gggttttact gatgcatata catgatggca tatgcagcat ctattcatat gctctaacct    4620
tgagtaccta tctattataa taaacaagta tgttttataa ttattttgat cttgatatac    4680
ttggatgatg gcatatgcag cagctatatg tggattttt tagccctgcc ttcatacgtt    4740
atttatttgc ttggtactgt ttcttttgtc gatgctcacc ctgttgtttg gtgttacttc    4800
tgcaggtcga ctctagagga tccacacgac accatgtccg cccgcgaggt gcacatcgac    4860
gtgaacaaca agaccggcca caccctccag ctggaggaca agaccaaggct cgacggcggc    4920
aggtggcgca ccctcccgac caacgtggcc aacgaccaga tcaagacctt cgtcgccgaa    4980
tccaacggct tcatgaccgg caccgagggc gccatctact actcaattaa tggcgaggcc    5040
gagatcagcc tctacttcga caacccgttc gccggctcca caaatacga cggccactcc    5100
aacaagtccc agtacgagat catcacccag ggcggctccg caaccagtc ccacgtgacc    5160
tacaccatcc agaccaccctc ctcccgctac ggccacaagt cctgagtcat gagtcatgag    5220
tcagttaacc tagacttgtc catcttctgg attggccaac ttaattaatg tatgaaataa    5280
aaggatgcac acatagtgac atgctaatca ctataatgtg gcatcaaag ttgtgtgtta    5340
tgtgtaatta ctagttatct gaataaaaga gaaagagatc atccatattt cttatcctaa    5400
atgaatgtca cgtgtcttta taattctttg atgaaccaga tgcatttcat taaccaaatc    5460
catatacata taaatattaa tcatatatta ttaatataac ttgggttagc aaaacaaatc    5520
tagtctaggt gtgttttgcg aatgcggccg cggaccgaat tgggatctg catgaaagaa    5580
actgtcgcac tgctgaaccg caccttgtca ctttcatcga acacgacctg tgcccaagat    5640
gacggtgctg cggtctaagt gaggctgaat tgccttggac agaagcggac tcctacaat    5700
tagttaggcc aaacggtgca tccatgtgta gctccgggct cggctgtat cgccatctgc    5760
aatagcctcc atggagctcg ttccatgtag ttggagatga accaatgatc gggcggttgg    5820
acgtatgttc ctgtgtactc cgatagtaga gtacgtgtta gctctttcat ggtgcaagtg    5880
aaatttgtgt tggtttaatt acccctacgt tagttgcggg acaggagaca catcatgaat    5940
ttaaaggcga tgatgtcctc tcctgtaatg ttattctttt gatgtgatga atcaaaatgt    6000
catatataaac atttgttgct ctttagttag gcctgatcgt agaacgaaat gctcgtgtag    6060
cggggctacg agcctatgac gcaataacac tggtttgccg gcccggagtc gcttgacaaa    6120
```

```
aaaaagcatg ttaagtttat ttacaattca aaacctaaca tattatattc cctcaaagca   6180
ggttcacgat cacacctgta cctaaaaaaa acatgaagaa tatattactc cattattatg   6240
agatgaacca cttggcaaga gtggtaagct atataaaaaa atgaacatta ttacgagatg   6300
ttatatgcca ttatattgat tcgaagatat atgtttcttt ctcccacggg cacctaacgg   6360
atacatgata aggccaaggc agatcacggg aaattattcg aatacatgtt acgccctatt   6420
gccggaaaaa aaatgcaggg caggtgttgg ccgtagcgat ttaagcactt aagctggagg   6480
ttgccacact tggatgcaag cgtctgaccc ttctaaaaca tcggcggctt tgtccgtatc   6540
cgtatcccct atccgacatc tagctggcca cacgacgggg ctgggcagat cgtggatgcc   6600
gggtcgacgt cgatcgtcag ccatcataga ccaatcgacc atctgttatg gatgcttgct   6660
agctagacta gtcagacata aaatttggat actttctccc aactgggaga cggggactga   6720
tgtgcagctg cacgtgagct aaattttttcc ctataaatat gcatgaaata ctgcattatc   6780
ttgccacagc cactgccaca gccagataac aagtgcagct ggtagcacgc aacgcatagc   6840
tctggacttg tagctaggta gccaaccgga tccacacgac accatgctcg acaccaacaa   6900
ggtgtacgag atcagcaacc acgccaacgg cctctacgtc gccacctacc tctccctcga   6960
cgactccggc gtgtccctca tgaacaagaa cgacgacgac atcgacgact acaacctcaa   7020
gtggttcctc ttcccgatcg acgacgacca gtacatcatc acctcctacg ccgccaacaa   7080
ctgcaaggtg tggaacgtga acaacgacaa gattaatgtg tcaacctact cctccaccaa   7140
ctccatccag aagtggcaga tcaaggccaa cggctcctcc tacgtgatcc agtccgacaa   7200
cggcaaggtg ctcaccgccg caccggcca ggcctcggc ctcatccgcc tcaccgacga   7260
gtcctccaac aacccgaacc agcaatggaa cctgacgtcc gtgcagacca tccagctccc   7320
gcagaagccg atcatcgaca ccaagctcaa ggactacccg aagtactccc cgaccggcaa   7380
catcgacaac ggcacctccc cgcagctcgat gggctggacc ctcgtgccgt gcatcatggt   7440
gaacgacccg aactacgaca agaacaccca gatcaagacc acccgtact acatcctcaa   7500
gaagtaccag tactggcaga gggccgtggg ctccaacgtc gcgctccgcc cgcacgagaa   7560
gaagtcctac acctacgagt ggggcaccga gatcgaccag aagaccacca tcatcaacac   7620
cctcggcttc cagatcaaca tcgacacgcg catgaagttc gacatcccgg aggtgggcgg   7680
cggtaccgac gagatcaaga cccagctcaa cgaggagctc aagatcgagt attcacatga   7740
gacgaagatc atggagaagt accaggagca gtccgagatc gacaacccga ccgaccagtc   7800
catgaactcc atcggcttcc tcaccatcac ctccctggag ctctaccgct acaacggctc   7860
cgagatccgc atcatgcaga tccagacctc cgacaacgac acctacaacg tgacctccta   7920
cccgaaccac cagcaggccc tgctgctgct gaccaaccac tcctacgagg aggtggagga   7980
gatcaccaac atcccgaagt ccaccctcaa gaagctcaag aagtactact ctgagtcat   8040
gagtcatgag tcagttaacc tagacttgtc catcttctgg attggccaac ttaattaatg   8100
tatgaaataa aaggatgcac acatagtgac atgctaatca ctataatgtg ggcatcaaag   8160
ttgtgtgtta tgtgtaatta ctagttatct gaataaaaga gaaagagatc atccatattt   8220
cttatcctaa atgaatgtca cgtgtcttta taattcttg atgaaccaga tgcatttcat   8280
taaccaaatc catatacata taaatattaa tcatatataa ttaatatcaa ttgggttagc   8340
aaaacaaatc tagtctaggt gtgttttgcg aattcccatg gagtcaaaga ttcaaatga   8400
ggacctaaca gaactcgccg taaagactgg cgaacagttc atacagagtc tcttacgact   8460
caatgacaag aagaaaatct tcgtcaacat ggtggagcac gacacgcttg tctactccaa   8520
aaatatcaaa gatacagtct cagaagacca aagggcaatt gagactttc aacaaagggt   8580
aatatccgga aacctcctcg gattccattg cccagctatc tgtcacttta ttgtgaagat   8640
agtggaaaag gaaggtggct cctacaaatg ccatcattgc gataaaggaa aggccatcgt   8700
tgaagatgcc tctgccgaca gtggtcccaa agatggaccc ccaccacga ggagcatcgt   8760
ggaaaagaa gacgttccaa ccacgtcttc aaagcaagtg gattgatgtg atatctccac   8820
tgacgtaagg gatgacgcac aatcccacta tccttcgcaa gacccttcct ctatataagg   8880
aagttcattt catttggaga ggacagggta cccggggta caccatgtct ccggagagga   8940
gaccagttga gattaggcca gctacagcag ctgatatgcc gcgtttgt gatatcgtta   9000
accattacat tgagacgtct acagtgaact ttaggacaga gccacaaaca ccacaagagt   9060
ggattgatga tctagagagg ttgcaagata gatacccttg gttggttgct gaggttgagg   9120
tgtgttggc tggtattgct tacgctgggc cctggaaggc taggaacgct tacgattgga   9180
cagttgagag tactgtttac gtgtcacata ggcatcaaag gttgggccta ggatccacat   9240
tgtacacaca tttgcttaag tctatggagg cgcaaggttt taagtctgtg gttgctgtta   9300
taggccttcc aaacgatcca tctgttaggt tgcatgagc tttgggatac acagcccggg   9360
gtacattgcg cgcagctgga tacaagcagt gtggatgcca tgatgttggt ttttggcaaa   9420
gggattttga gttgccagct cctccaaggc cagttaggcc agttaccag atctgagtcg   9480
acctgcaggc atgcccgctg aaataccag tctctctcta caaatctatc tctctctata   9540
ataatgtgtg agtagttccc agataaggga attagggttc ttatagggtt tcgctcatgt   9600
gttgagcata taagaaaccc ttagtatgta tttgtatttg taaaatactt ctatcaataa   9660
aatttctaat tcctaaaacc aaaatccagg gcgagctcgg tacccgggga tcctctagag   9720
tcgacctgca ggcatgcccg cggatatcga tgggccccgg ccgaagcttc ggtccgggcc   9780
atcgtggcct cttgctcttc aggatgaaga gctatgttta aacgtgcaag cgctcaattc   9840
gccctatagt gagtcgtatt acaatcgtac gcaattcagt acattaaaaa cgtccgcaat   9900
gtgttattaa gttgtctaag cgtcaatttt tcccttctat ggtcccgttt gtttatcctc   9960
taaattatat aatccagctt aaataagtta agagacaaac aaacaacaca gattattaaa  10020
tagattatgt aatctagata cctagattat gtaatccata agtagaatat caggtgctta  10080
tataatctat gagctcgatt atataatctt aaaagaaaac aaacagagcc cctataaaaa  10140
ggggtcaagt ggacacttgg tcactcattt aatccctccc tctcctcttt tatccctctt  10200
tttggtgtat tcaccaatag tggtgtgcac ctgtcgattgg ctcgtaaaaa ttcttggacg  10260
gatgaagag tgaagagata agcaagtcaa agaaaagtaa caacgaagct tcatcagcta  10320
caaatttttgg cccaactggt tgcaccagca ccaaacttac gtatacatga ttatctctgt  10380
ttccctcatt tcgaagaaaa aaacgggttt caaaaccac tgctttcagg agtaaaaaaa  10440
gataataatc tgaaacattg cttccacctt ggcccttatt tggttacgtt gcaattcacc  10500
ccaatcacca tgtggattga gatggattgc agtgtagcta agaaaccct taggccctgt  10560
ttgcatagga atacaccagg aattattcca gctaatcaaa atttatataa atgagagaaa  10620
caattcggat aggaattgtt ccaggacttc attctgcagt aaccgaacgg ccccttaatc  10680
cacccccaata cacgtggatt ggagtggatt gaggtacagc caaacaaggc ctaagtcag  10740
atcaaataaa tcacccgtca tattcttcta cctacaaaaa cagcaataaa cacctgaatg  10800
aagttctaat ttgcacagtg taggtaggat gaaaatagtt acctcctcat ggtcagtaac  10860
```

```
tcttggcaca caacttcaca tgtaatcgat gtaccacttg gctcttgcct gaaacccaat    10920
acatctttag cataagaata atattatgat ggcaaggcat gatcaccagc actcctttat    10980
tgtttagtaa gtctatcact ccccaaaaca attcaaatga acagagatgc attgccccca    11040
atgaattcta tttcaattag ccggaaaatt ctacttcatc agaagcatcc aaattgccag    11100
catccctact agactgacca tgaccaggct gccgcagatg cctcttttc tgtcctctcc     11160
tctttgcctt gagtttctct tcaagatccc tcaccccacg tctcttatac atcttaaagc    11220
taacatgtct ctcctccgcc atcttcctaa ccttctcagt aatctcagca gcaatctgac    11280
ggttgtacaa cttcttcagc cccttcatca actttgcaaa tgtgtcaggc tgtggcatca    11340
gtcctgcctc tagcatgtct aagcaataca ggcaggcctc cttgacatgt ttcttcgcaa    11400
acagtgcatg aatccagata gtccatgcac tcacattgag ctcacagcct ttgctcacaa    11460
tacatttcca aacatccttt gcaagctcaa gtttctcatc tctgaccaac gcattgagga    11520
ggtccttcag caccccatat tgcggtacca caaagagccc cctcccaacc atgtctttaa    11580
aataactaca tgcctcaatc agcaaaccct gcccaacaag gccactcacc acgatagcaa    11640
atgtatcgac cacaggactg agcccagcac tttccatctc attccacaat gtcatggctt    11700
gcttggtctc cccaagcctg caggccaacc gaatcaccac attgtatatc ttgagatctg    11760
gtggacaccg gcactcccgc atcctctcca tcagctccaa gcactcctca agctgctcct    11820
tcttctcgtg tgctacaaag aaaccatggt acacggcagc gtccacccgc aggccatccc    11880
tcgacatagc atccaagaac tcgtacccct gggat                               11915

SEQ ID NO: 3         moltype = DNA   length = 11942
FEATURE              Location/Qualifiers
source               1..11942
                     mol_type = other DNA
                     organism = synthetic construct
SEQUENCE: 3
ctgagcgcac aacagcgagt cgcatggcac cggacgacat gagcgagatt tagatcggag    60
ggtgcggaca tggggcaacc tgcgcagcta acgcagggat ccacgaccgc accaacgaag    120
ccaagcccgg gcacgtcccc aggcaggttg ggccctggtt ccaccagcgg atgcatgcag    180
tgaagcgggg acggagagac aagccgaggg cgcgggtggg aatggcgtcc gggaggacga    240
gtggaggaga agaatctaga ggcatcgaga ttcgagaagc cgacggagac aagattcgtg    300
tgggggagaa caaaccgcgg ggctgagcgc cgttgatatg ggatcagacg gtgtggaataa   360
aaaaagtgac gttgatagaa cgtctggcca gtgaaaaaac aaaacaactc caacaaaata    420
cttaaaaagc tcttataccc taaatgtagg ggatcaaaca cgtctctaca ctatttagca    480
gcgtcctcta aatgatcctc taaatttaga gaacgctact agattctcta tatatagttt    540
ctctaaacga tcttttatcc atttaaatac tttaaataac cggtttaaca aaactaaaat    600
atatacaata catttgagag tatgacaaat acgtatgtat aaaaataaaa aataaaataa    660
tgtattagtc tactttgaat cttcttttct tcataatata atgatgtata gctctcatgt    720
gcgttgagaa aaaagttaga gctagacgtt taatgtgtag tgacagtctt cgacgaaatc    780
tccctaatga gatgaattac tggaggttcc atcagaaagt cccctgaaaa gaggcattta    840
tttagtttag tcagcaattt ctgggaacac aaatattctt ttgttatcac cactattaaa    900
aatctatggt tataacttat aataacatga aaaataatt tagcatccca tatatataaa     960
aactgaagga agccatatat actaacataa gttaggagaa actaagaagg ttgtgcaaag    1020
cttgcactgc tccaaaatac tgcaaacaac cactctcctc taccaaccaa gaaaactcat    1080
gtactccctc cgttcttttt tatttgtcgc attttagttt aaaaatgaac tagcagtcga    1140
caaatattcg agaacagata tagtatatac taacataact taggagatac taagaaagtt    1200
gcgcagagct ttcactgttc caaattactg caaagcctct cccctctgcc agtacatcta    1260
cgagatgttt cagttaaaca aagattcaga caagtgatga gccacttcgt gtcatagatt    1320
gtgtggtcaa ccaacccatt gatgccacgg tttttgtgca tccatgcttt tgtattaaaa    1380
catcagttat gtttaccatg tccgatatgc tctacataat gacaatcaac ttggtgttca    1440
ttatatttac aatgttagga atttcaatag ctacgaacac ttcaatagaa gtgcctttgt    1500
gggatcacct taatgtgttg ttgatgtaag gagaagaatc ttaatttact cttgctaaat    1560
ttgaactaca caaaccact gcactgagga ttgtcctaat aaaattactg ctcatacacgt    1620
tagcatctgt tcagatactg agctaatccc taggattaaa ggatttgtaa aagatatgcc    1680
caatcattca ttttagttat ttatttctta gttatccact tgaagattta catacatttg    1740
aaataaattt cttagaggta aagtgaaaat cagttattta aatacatttt agttatttat    1800
tttcttcttt ttcctaattt ttccttgtat ttgaagtctg aaaagataac tttgcccta     1860
tacatatttt atcttctacg tacgcatctg aacaacgtct ctttgtcccc tgatcgtgca    1920
gcaattagtc ctatgaatcg cgtttaagcg ctgcaaaatc atggctgggg cttcgtcctc    1980
gagtcgtcct gctgctcgat gtcacctcga gtcccgcacc gacctcagtg cttgttcttg    2040
ttggagccac ctctctcgga cgatcgccaa agacggataa ggccgaagcc gtcacttcag    2100
accgcgctca tgcgccgtag cagactccta catagcaggg ccaggggtatg tggacctttg    2160
caagtttagg attggaacca gcgaccgaaa tccacaagat tggagcaaac gaccaaaaat    2220
tcacaaggat tggcggctga cattgccagc gcggatcgc atgcggcggc ggcggccggg     2280
gcgagcacgg gagcaggcga cagtcgagct ccattggaac gtagaaatac ttaagggcaa    2340
ggtctccaaa tacttgaaaa aataggaaaa agaagaaaat acatgaaatg atattgaaat    2400
caattggaag atgttatgaa tcttgttttt gcaaagcgaa cgattcagat ggcaaaacta    2460
tgaatctttt tgtttgaagt cccaaatata aaattttctc gtactcacca acattggtgc    2520
gcacctgtga ttggctcata aaaattcttg gagggacgga agaaagagtg aagggataag    2580
caagtaaaag cgctcaaact ttcccttcta tggtcccgtt tgtttagttt aaactgaagg    2640
cgggaaacga caatctgatc atgagcgag aattaaggga gtcacgttat gaccccgcc      2700
gatgacgcgg gacaagccgt tttacgtttg gaactgacag aaccgcaacg ttgaaggagc    2760
cactcagcaa gcttactagt agcgctgttt aaacgctctt caactggaag agcggttacc    2820
cggaccgaag cttgcatgcc tgcagtgcag cgtgacccgg tcgtgcccct ctctagagat    2880
aatgagcatt gcatgtctaa gttataaaaa attaccacat atttttttg tcacacttgt     2940
ttgaagtgca gttatctat ctttatacat atatttaaac tttactctac gaataatata     3000
atctatagta ctacaataat atcagtgttt tagagaatca tataaatgaa cagttagaca    3060
tggtctaaag gacaattgag tattttgaca acaggactct acagtttat cttttagtg      3120
tgcatgtgtt ctccttttt tttgcaaata gcttcaccta tataatactt catccatttt    3180
attagtacat ccatttaggg tttagggtta atggttttta tagactaatt ttttagtac     3240
```

```
atctatttta ttctatttta gcctctaaat taagaaaact aaaactctat tttagttttt   3300
ttatttaata atttagatat aaaatagaat aaaataaagt gactaaaaat taaacaaata   3360
cccttttaaga aattaaaaaa actaaggaaa cattttttctt gtttcgagta gataatgcca   3420
gcctgttaaa cgccgtcgac gagtctaacg gacaccaacc agcgaaccag cagcgtcgcg   3480
tcgggccaag cgaagcagac ggcacggcat tctgtcgct gcctctggac ccctctcgag   3540
agttccgctc caccgttgga cttgctccgc tgtcggcatc cagaaattgc gtggcggagc   3600
ggcagacgtg agccggcacg gcaggcggcc tcctcctcct ctcacggcac cggcagctac   3660
gggggattcc tttcccaccg ctccttcgct ttccttcct cgcccgccgt aataaataga   3720
caccccctcc acaccctctt tccccaacct cgtgttgttc ggagcgcaca cacacacaac   3780
cagatctccc ccaaatccac ccgtcggcac ctccgcttca aggtacgccg ctcgtcctcc   3840
cccccccccc ctctctacct tctctagatc ggcgttccgg tccatggtta gggcccggta   3900
gttctacttc tgttcatgtt tgtgttagat ccgtgtttgt gttagatccg tgctgctagc   3960
gttcgtacac ggatgcgacc tgtacgtcag acacgttctg attgctaact tgccagtgtt   4020
tctcttttggg gaatcctggg atggctctag ccgttccgca gacgggatcg atttcatgat   4080
ttttttttgtt tcgttgcata gggtttggtt tgcccttttc cttatttca atatatgccg   4140
tgcacttgtt tgtcgggtca tctttttcatg cttttttttg tcttggttgt gatgatgtgg   4200
tctggttggg cggtcgttct agatcggagt agaattctgt ttcaaactac ctggtggatt   4260
tattaattt ggatctgtat gtgtgtgcca tacatattca tagttacgaa ttgaagatga   4320
tggatggaaa tatcgatcta ggataggtat acatgttgat gcgggtttta ctgatgcata   4380
tacagagatg cttttgttc gcttggttgt gatgatgtgg tgtggttggg cggtcgttca   4440
ttcgttctag atcggagtag aatactgttt caaactacct ggtgtattta ttaattttgg   4500
aactgtatgt gtgtgtcata catcttcata gttacgagtt taagatggat ggaaatatcg   4560
atgtaggata ggtatacatg ttgatgtggg ttttactgat gcatatacat gatggcatat   4620
gcagcatcta ttcatatgct ctaaccttga gtacctatct attataataa acaagtatgt   4680
tttataatta ttttgatctt gatatacttg gatgatggca tatgcagcag ctatatgtgg   4740
attttttag ccctgccttc atacgctatt tatttgcttg gtactgtttc ttttgtcgat   4800
gctcaccctg ttgtttggtg ttacttctgc aggtcgactc tagaggatcc acacgacacc   4860
atgtccgccc gcgaggtgca catcgacgtg aacaacaaga ccggcacac cctccagctg   4920
gaggacaaga ccaagctcga cggcggcagg tggcgcacct ccccgaccaa cgtggccaac   4980
gaccagatca agaccttcgt ggccgaatcc aacggcttca tgaccggcac cgagggcacc   5040
atctactact caattaatgg cgaggccgag atcagcctct acttcgacaa cccgttcgcc   5100
ggctccaaca aatacgacgg ccactccaac aagtcccagt acgagatcat cacccagggc   5160
ggctccggca accagtccca cgtgacctac catccagaa ccacctcctc ccgctacggc   5220
cacaagtcct gagtcatgag tcatgagtca gttaacctag acttgtccat cttctggatt   5280
ggccaactta attaatgtat gaaataaaag gatgcacaca tagtgacatg ctaatcacta   5340
taatgtgggc atcaaagttg tgtgttatgt gtaattacta gttatctgaa taaaagagaa   5400
agagatcatc catatttctt atcctaaatg aatgtcacgt gtctttataa ttctttgatg   5460
aaccagatgc atttcattaa ccaaatccat atacatataa atattaatca tatataatta   5520
atatcaattg ggttagcaaa acaaatctag tctaggtgtg ttttgcgaat gcggccgcgg   5580
accgaattgg ggatctgcat gaaagaaact gtcgcactgc tgaaccgcac cttgtcactt   5640
tcatcgaaca cgacctgtgc ccaagatgac ggtgctgcgg tctaagtgag ctgaattgc   5700
cttgacagaa agcggactcc ctacaattag ttaggccaaa cggtgcatcc atgtgtagct   5760
ccggggctcgg gctgtatcgc catctgcaat agcatccatg gagctcgttc catgtagttg   5820
gagatgaacc aatgatcggg cgtgtggacg tatgttcctg tgtactccga tagtagagta   5880
cgtgttagct cttttcatggt gcaagtgaaa tttgtgttgg tttaattacc cctacgttag   5940
ttgcgggaca ggagacacat catgaattta aaggcgatga tgtcctctcc tgtaatgtta   6000
ttcttttgat gtgatgaatc aaaatgtcat ataaaacatt tgttgctctt tagttaggcc   6060
tgatcgtaga acgaaatgct cgtgtagcgg ggctacgagc ctatgacgca ataacactgg   6120
tttgccggcc cggagtcgct tgacaaaaaa aagcatgtta agtttatta caattcaaaa   6180
cctaacatat tatattccct caaagcaggt tcacgatcac acctgtacct aaaaaaaaca   6240
tgaagaatat attactccat tattatgaga tgaaccactt ggcaagagtg gtaagctaa   6300
taaaaaaatg aacattatta cgagatgtta tatgccatta tattgattcg aagtatatg   6360
tttcttttctc ccacgggcac ctaacggata catgataagg ccaaggcaga tcacgggaaa   6420
ttattcgaat acatgttacg ccctattgcc ggaaaaaaaa tgcagggcag gtgttggccg   6480
tagcgattta agcacttaag ctggaggttta ccacactttg atgcaagcgt ctgacccttc   6540
taaaacatcg gcggctttgt ccgtatccgt atccctatc cgacatctag ctggccacac   6600
gacggggctg ggcagatcgt ggatgccggg tcgacgtcga tcgtcagcca tcatagacca   6660
atcgaccatc tgttatggat gcttgctagc tagactagtc agacataaaa tttggatact   6720
ttctcccaac tgggagacgg ggactgatgt gcagctgcac gtgagctaaa tttttcccta   6780
taaatatgca tgaaatactg cattatcttg ccacagccac tgccacagcc agataacaag   6840
tgcagctggt agcacgcaac gcatagctct ggacttgtag ctaggtagcc aaccggatcc   6900
acacgacacc atgctcgaca ccaacaaggt gtacgagatc agcaaccacg ccaacggcct   6960
ctacgccgcc acctacctct ccctcgacga ctccggcgtg tccctcatga caagaacga   7020
cgacgacacc gacgactaca acctcaagtg gttcctcttc ccgatcgacg agaccagtta   7080
catcatcacc tcctacgccg ccaacaactg caaggtgtgg aacgtgaaca acgacaagat   7140
taatgtgtca acctactcct ccaccaactc catccagaag tggcagatca aggccaacgg   7200
ctcctcctac gtgatccagt ccgacaacgg caaggtgctc accgccggca ccggccaggc   7260
cctcggcctc atccgcctca ccgacgagtc ctccaacaac ccgaaccagc aatgaacct   7320
gacgtccgtg cagaccatcc agctcccgca gaagccgatc atcgacacca agctcaagga   7380
ctacccgaag tactcccgga ccggcaacat cgacacggc acctcccgc agctcatggg   7440
ctggaccctc gtgccgtgca tcatggtgaa cgacccgaac atcgacaaga caccccagat   7500
caagaccacc ccgtactaca tcctcaagaa gtaccagtac tggcagaggg ccgtgggctc   7560
caacgtcgcg ctccgcccgc acgagaagaa gtcctacacc tacgagtggg gcaccgagat   7620
cgaccagaag accaccatca tcaacaccct cggcttccag atcaacatcg acagcggcat   7680
gaagttcgac atcccggagg tgggcggcgg taccgacgag atcaagaccc agctcaacga   7740
ggagctcaag atcgagtatt cacatgagac gaagatcatg gagaagtacc aggagcagtc   7800
cgagatcgac aacccgaccg accagtccat gaactccatc ggcttcctca ccatcacctc   7860
cctgagctc taccgctaca cgggctccga gatccgcatc atgcagatcc agacctccga   7920
caacgacacc tacaacgtga cctcctaccc gaaccaccag caggccctgc tgctgctgac   7980
```

```
caaccactcc tacgaggagg tggaggagat caccaacatc ccgaagtcca ccctcaagaa   8040
gctcaagaag tactacttct gagtcatgag tcatgagtca gttaacctag acttgtccat   8100
cttctggatt ggccaactta attaatgtat gaaataaaag gatgcacaca tagtgacatg   8160
ctaatcacta taatgtgggc atcaaagttg tgtgttatgt gtaattacta gttatctgaa   8220
taaaagagaa agagatcatc catatttctt atcctaaatg aatgtcacgt gtctttataa   8280
ttctttgatg aaccagatgc atttcattaa ccaaatccat atacatataa atattaatca   8340
tatataatta atatcaattg ggttagcaaa acaaatctag tctaggtgtg ttttgcgaat   8400
tcccatggag tcaaagattc aaatagagga cctaacagaa ctcgccgtaa agactggcga   8460
acagttcata cagagtctct tacgactcaa tgacaagaaa aaaatcttcg tcaacatggt   8520
ggagcacgac acgcttgtct actccaaaaa tatcaaagat acagtctcag aagaccaaag   8580
ggcaattgag acttttcaac aaagggtaat atccggaaac ctcctcggat tccattgccc   8640
agctatctgt cactttattg tgaagatagt ggaaaaggaa ggtggctcct acaaatgcca   8700
tcattgcgat aaaggaaagg ccatcgttga agatgcctct gccgacagtg gtcccaaaga   8760
tggaccccca cccacgagga gcatcgtgga aaaagaagac gttccaacca cgtcttcaaa   8820
gcaagtggat tgatgtgata tctccactga cgtaagggat gacgcacaat cccactatcc   8880
ttcgcaagac ccttcctcta tataaggaag ttcatttcat ttggagagga cagggtaccc   8940
gggatccac catgtctccg gagaggagac cagttgagat taggccagct acagcagctg   9000
atatggccgc ggtttgtgat atcgttaacc attacattga gacgtctaca gtgaacttta   9060
ggacagagcc acaaacacca caagagtgga ttgatgatct agagaggttg caagatagat   9120
acccttggtt ggttgctgag gttgagggtg ttgtggctgg tattgcttac gctgggccct   9180
ggaaggctag gaacgcttac gattggacag ttgagatac tgtttacgtg tcacataggc   9240
atcaaaggtt gggcctagga tccacattgt acacacattt gcttaagtct atggaggcgc   9300
aaggttttaa gtctgtggtt gctgttatag gccttccaaa cgatccatct gttaggttgc   9360
atgaggcttt gggatacaca gcccgggta cattgcgcgc agctggatac aagcatggtg   9420
gatggcatga tgttggtttt tggcaaaggg attttgagtt gccagctcct ccaaggccag   9480
ttaggccagt tacccagatc tgagtcgacc tgcaggcatg cccgctgaaa tcaccagtct   9540
ctctctacaa atctatctct ctctataata atgtgtgagt agttcccaga taagggaatt   9600
agggttctta tagggtttcg ctcatgtgtt gagcatataa gaaaccctta gtatgtattt   9660
gtatttgtaa aatacttcta tcaataaaat ttctaattcc taaaaccaaa atccagggcg   9720
agctcggtac ccggggatcc tctagagtcg acctgcaggc atgcccgcgg atatcgatgg   9780
gccccggccg aagcttcggt ccgggccatc gtggcctctt gctcttcagg atgaagagct   9840
atgtttaaac gtgcaagcgc tcaattcgcc ctatatgag tcgtattaca atcgtacgca   9900
attcagtaca ttaaaaacgt ccgcaatgtg ttattaagtt gtctaagcgt caatttttcc   9960
cttctatggt cccgtttgtt tatcctctaa attatataat ccagcttaaa taagttaaga  10020
gacaaacaaa caacacagat tattaaatag attatgtaat ctagataccct agattatgta  10080
atccataagt agaatatcag gtgcttatat aatctatgag ctcgattata taatcttaaa  10140
agaaaacaaa cagagcccct ataaaagggg tcaagtggaa cacttggtca ctcatttaat  10200
ccctccctct cctcttttat ccctcttttt ggtgtattca ccaatagtgg tgtgcacctg  10260
tgattggctc gtaaaaattc ttggacggat ggaagagtga agagataagc aagtcaaaga  10320
aaagtaacaa cgaagcttca tcagctcaaa attttggccc aactggttgc accagcacca  10380
aacttacgta tacatgatta tctctgtttc cctcatttcg aagaaaaaaa cgggtttcaa  10440
aacccactgc tttcaggagt aaaaaaagat aataatctga acattgcttc ccaccttggc  10500
ccttatttgg ttacgttgca attcacccca atccacatgt ggattgagat ggattgcagt  10560
gtagctagac aaaacccttag gccctgtttg cataggaata caccaggaat tattccagct  10620
aatcaaaatt tatataaatg agagaaacaa ttcggatagg aattgttcca ggacttcatt  10680
ctgcagtaac cgaacggccc cttaatccac cccaatacac gtggattgga gtggattgag  10740
gtacagccaa acaaggccta agtgcagatc aaatataatca cccgtcatat tcttctacct  10800
acaaaaacag caataaacac ctgaatgaag ttctaatttg cacagtgtag gtaggatgaa  10860
aatagttacc tcctcatggt cagtaactct tggcacacaa cttcacatgt aatcgatgta  10920
ccacttggct cttgcctgaa acccaataca tctttagcat aagaataata ttatgatggc  10980
aaggcatgat caccagcact cctttattgt ttagtaagtc tatcactccc caaaacaatt  11040
caaatgaaca gagatgcatt gccccaatg aattctattt caattagccg gaaaattcta  11100
cttcatcaga agcatccaaa ttgccagcat ccctactaga ctgaccatga ccaggctgcc  11160
gcagatgcct cttttctgt cctctcctct ttgccttgag tttctcttca agatccctca  11220
ccccacgtct cttatacatc ttaaagctaa catgtctctc ctccgccatc ttcctaacct  11280
tctcagtaat ctcagcagca atctgacggt tgtacaactt cttcagcccc ttcatcaact  11340
ttgcaaatgt gtcaggctgt ggcatcagtc ctgcctctag catgtctaag caatacaggc  11400
aggcctcctt gacatgtttc ttcgcaaaca gtgcatgaat ccagatagtc catgcactca  11460
cattgagctc acagcctttg ctcacaatac atttccaaac atccttgtca agctcaagtt  11520
tctcatctct gaccaacgca ttgaggaggt ccttcagcac cccatattgc ggtaccacaa  11580
agagcccccct cccaaccatg tcttttaaaat aactacatgc ctcaatcagc aaaccctgcc  11640
caacaaggcc actcaccacg atagcaaatg tatcgaccac aggactgagc ccagcacttt  11700
ccatctcatt ccacaatgtc atggcttgct ggtctcccc aagcctgcag gccaaccgaa  11760
tcaccacatt gtatatcttg agatctggtg gacaccggca ctcccgcatc ctctccatca  11820
gctccaagca ctcctcaagc tgctccttct tctcgtgtgc tacaaagaaa ccatggtaca  11880
cggcagcgtc cacccgcagg ccatccctcg acatagcatc caagaactcg taccctgggg  11940
at                                                                 11942
```

SEQ ID NO: 4           moltype = DNA  length = 27
FEATURE                Location/Qualifiers
source                 1..27
                       mol_type = other DNA
                       organism = synthetic construct
SEQUENCE: 4
tttaaactat cagtgtttga gcgcttt                                        27

| SEQ ID NO: 5 | moltype = DNA length = 27 |
|---|---|
| FEATURE | Location/Qualifiers |
| source | 1..27 |
| | mol_type = other DNA |
| | organism = synthetic construct |

SEQUENCE: 5
tttcccgcct tcagtttaaa ctatcag                                27

| SEQ ID NO: 6 | moltype = DNA length = 27 |
|---|---|
| FEATURE | Location/Qualifiers |
| source | 1..27 |
| | mol_type = other DNA |
| | organism = synthetic construct |

SEQUENCE: 6
tttgagcgct tttacttgct tatccct                                27

| SEQ ID NO: 7 | moltype = DNA length = 27 |
|---|---|
| FEATURE | Location/Qualifiers |
| source | 1..27 |
| | mol_type = other DNA |
| | organism = synthetic construct |

SEQUENCE: 7
tttccctttct atggtcccgt ttgttta                                27

| SEQ ID NO: 8 | moltype = DNA length = 47 |
|---|---|
| FEATURE | Location/Qualifiers |
| source | 1..47 |
| | mol_type = other DNA |
| | organism = synthetic construct |

SEQUENCE: 8
ataagcaagt tttcccttct atggtcccgt tgtttactc aaacact            47

| SEQ ID NO: 9 | moltype = DNA length = 47 |
|---|---|
| FEATURE | Location/Qualifiers |
| source | 1..47 |
| | mol_type = other DNA |
| | organism = synthetic construct |

SEQUENCE: 9
gcgctcaaac tttcccttct atggtcccgt tgtttagtt taaactg            47

| SEQ ID NO: 10 | moltype = DNA length = 47 |
|---|---|
| FEATURE | Location/Qualifiers |
| source | 1..47 |
| | mol_type = other DNA |
| | organism = synthetic construct |

SEQUENCE: 10
agaaagagtg tttcccttct atggtcccgt tgtttagat catgagc            47

| SEQ ID NO: 11 | moltype = DNA length = 1127 |
|---|---|
| FEATURE | Location/Qualifiers |
| source | 1..1127 |
| | mol_type = other DNA |
| | organism = synthetic construct |

SEQUENCE: 11
```
tcttgttgga gccacctctc tcggacgatc gccaaagacg gataaggccg aagccgtcac   60
ttcagaccgc gctcatgcgc cgtagcagac tcctacatag cagggccagg gtatgtggac  120
ctttgcaagt ttaggattgg aaccagcgac cagaatccac aagattggag caaacgacca  180
aaaattcaca aggattggcg gctgacattg ccagcgcggt atcgcatgcg gcggcggcgg  240
ccgggcgag cacgggagca ggcgacagtc gagctccatt ggaacgtaga aatacttaag  300
ggcaaggtct ccaaatactt gaaaaaatag gaaaaagaag aaaatacatg aaatgatatt  360
gaaatcaatt ggaagatgtt atgaatcttg tttttgcaaa gcgaacgatt cagatggcaa  420
aactatgaat cttttgttt gaagtcccaa atataaaatt ttctcgtact caccaacatt  480
ggtgcgcacc tgtgattggc tcataaaaat tcttggaggg acggaagaaa gagtgaaggg  540
ataagcaagt tttcccttct atggtcccgt tgtttactc aaacactgat agtttaaact  600
gaaggcggga acgacaatc tgatcatgag cggagaatta agggagtcac gttatgaccc  660
ccgccgatga cgcgggacaa gccgttttac gtttggaact gacagaaccg caacgttgaa  720
ggagccactc agcaagctta ctagtagcgc tgtttaaacg ctcttcaact ggaagagcga  780
ttacccggac cgaagcttgc atgcctgcag tgcagcgtga cccggtcgtg cccctctcta  840
gagataatga gcattgcatg tctaagttat aaaaaaattac cacatatttt ttttgtcaca  900
cttgtttgaa gtgcagttta tctatctta tacatatatt taaactttac tctacgaata  960
atataatcta tagtactaca ataatatcag tgttttagag aatcatataa atgaacagtt  1020
agacatggtc taaggacaa ttgagtattt tgacaacagg actctacagt ttatctcttt  1080
tagtgtgcat gtgttctcct tttttttgc aaatagcttc acctata            1127
```

```
SEQ ID NO: 12            moltype = DNA  length = 1478
FEATURE                  Location/Qualifiers
source                   1..1478
                         mol_type = other DNA
                         organism = synthetic construct
SEQUENCE: 12
ctatgaatcg cgtttaagcg ctgcaaaatc atggctgggg cttcgtcctc gagtcgtcct    60
gctgctcgat gtcacctcga gtcccgcacc gacctcagtg cttgttcttg ttggagccac   120
ctctctcgga cgatcgccaa agacggataa ggccgaagcc gtcacttcag accgcgctca   180
tgcgccgtag cagactccta catagcaggg ccagggtatg tggacctttg caagtttagg   240
attggaacca gcgaccagaa tccacaagat tggagcaaac gaccaaaaat tcacaaggat   300
tggcggctga cattgccagc gcgggatcgc atgcggcggc ggcggccggg gcgagcacgg   360
gagcaggcga cagtcgagct ccattggaac gtagaaatac ttaagggcaa ggtctccaaa   420
tacttgaaaa aataggaaaa agaagaaaat acatgaaatg atattgaaat caattggaag   480
atgttatgaa tcttgttttt gcaaagcgaa cgattcagat ggcaaaacta tgaatctttt   540
tgtttgaagt cccaaatata aaattttctc gtactcacca acattggtgc gcacctgtga   600
ttggctcata aaaattcttg gagggacgga agaaagagtg aagggataag caagtaaaag   660
cgctcaaaca ctgatagttt aaactgaagg cgggaaacga caatctgatc atgagcggag   720
aattaaggga gtcacgttat gaccccgcc gatgacgcgg gacaagccgt tttacgtttg   780
gaactgacag aaccgcaacg ttgaaggagc cactcagcaa gcttactagt agcgctgttt   840
aaaacgctctt caactggaag agcggttacc cggaccgaag cttgcatgcc tgcagtgcag   900
cgtgacccgg tcgtgcccct ctctagagat aatgagcatt gcatgtctaa gttataaaaa   960
attaccacat attttttttg tcacacttgt ttgaagtgca gtttatctat ctttatacat  1020
atatttaaac tttactctac gaataatata atctatagta ctacaataat atcagtgttt  1080
tagagaatca tataaatgaa cagttagaca tggtctaaaa gacaattgaa tattttgaca  1140
acaggactct acagttttat cttttttagtg tgcatgtgtt ctccttttttt tttgcaaata  1200
gcttcaccta tataatactt catccatttt attagtacat ccatttaggg tttagggtta  1260
atggttttta tagactaatt tttttagtac atctattta ttctatttta gcctctaaat  1320
taagaaaact aaaactctat tttagttttt ttatttaata atttagatat aaaatagaat  1380
aaaataaagt gactaaaaat taaacaaata cccttttaaga aattaaaaaa actaaggaaa  1440
cattttttctt gtttcgagta gataatgcca gcctgtta                         1478

SEQ ID NO: 13            moltype = DNA  length = 23
FEATURE                  Location/Qualifiers
source                   1..23
                         mol_type = other DNA
                         organism = synthetic construct
SEQUENCE: 13
ccttctatgg tcccgtttgt tta                                            23

SEQ ID NO: 14            moltype = DNA  length = 25
FEATURE                  Location/Qualifiers
source                   1..25
                         mol_type = other DNA
                         organism = synthetic construct
SEQUENCE: 14
ctatgaatcg cgtttaagcg ctgca                                          25

SEQ ID NO: 15            moltype = DNA  length = 25
FEATURE                  Location/Qualifiers
source                   1..25
                         mol_type = other DNA
                         organism = synthetic construct
SEQUENCE: 15
taacaggctg gcattatcta ctcga                                          25

SEQ ID NO: 16            moltype = DNA  length = 1498
FEATURE                  Location/Qualifiers
source                   1..1498
                         mol_type = other DNA
                         organism = synthetic construct
SEQUENCE: 16
ctatgaatcg cgtttaagcg ctgcaaaatc atggctgggg cttcgtcctc gagtcgtcct    60
gctgctcgat gtcacctcga gtcccgcacc gacctcagtg cttgttcttg ttggagccac   120
ctctctcgga cgatcgccaa agacggataa ggccgaagcc gtcacttcag accgcgctca   180
tgcgccgtag cagactccta catagcaggg ccagggtatg tggacctttg caagtttagg   240
attggaacca gcgaccagaa tccacaagat tggagcaaac gaccaaaaat tcacaaggat   300
tggcggctga cattgccagc gcgggatcgc atgcggcggc ggcggccggg gcgagcacgg   360
gagcaggcga cagtcgagct ccattggaac gtagaaatac ttaagggcaa ggtctccaaa   420
tacttgaaaa aataggaaaa agaagaaaat acatgaaatg atattgaaat caattggaag   480
atgttatgaa tcttgttttt gcaaagcgaa cgattcagat ggcaaaacta tgaatctttt   540
tgtttgaagt cccaaatata aaattttctc gtactcacca acattggtgc gcacctgtga   600
ttggctcata aaaattcttg gagggacgga agaaagagtg aagggataag caagttttcc   660
cttctatggt cccgtttgtt tactcaaaca ctgatagttt aaactgaagg cgggaaacga   720
caatctgatc atgagcggag aattaaggga gtcacgttat gaccccgcc gatgacgcgg   780
gacaagccgt tttacgtttg gaactgacag aaccgcaacg ttgaaggagc cactcagcaa   840
gcttactagt agcgctgttt aaaacgctctt caactggaag agcggttacc cggaccgaag   900
cttgcatgcc tgcagtgcag cgtgacccgg tcgtgcccct ctctagagat aatgagcatt   960
```

```
gcatgtctaa gttataaaaa attaccacat atttttttg tcacacttgt ttgaagtgca   1020
gtttatctat ctttatacat atatttaaac tttactctac gaataatata atctatagta   1080
ctacaataat atcagtgttt tagagaatca tataaatgaa cagttagaca tggtctaaag   1140
gacaattgag tattttgaca acaggactct acagttttat cttttagtg tgcatgtgtt    1200
ctcctttttt tttgcaaata gcttcaccta tataatactt catccatttt attagtacat   1260
ccatttaggg tttagggtta atggttttta tagactaatt tttttagtac atctatttta   1320
ttctatttta gcctctaaat taagaaaact aaaactctat tttagttttt ttatttaata   1380
atttagatat aaaatagaat aaaataaagt gactaaaaat taaacaaata cccttttaaga  1440
aattaaaaaa actaaggaaa cattttttctt gtttcgagta gataatgcca gcctgtta    1498

SEQ ID NO: 17           moltype = DNA   length = 11942
FEATURE                 Location/Qualifiers
source                  1..11942
                        mol_type = other DNA
                        organism = synthetic construct
SEQUENCE: 17
ctgagcgcac aacagcgagt cgcatggcac cggacgacat gagcgagatt tagatcggag   60
ggtgcggaca tggggcaacc tgcgcagcta acgcagggat ccacacgacc accaacgaag   120
ccaagcccgg gcacgtcccc aggcaggttg ggccctggtt ccaccagcgg atgcatgcag   180
tgaagcgggg acggagagac aagccgaggg cgcgggtggg aatggcgtcc gggaggacga   240
gtggaggaga agaatctaga ggcatcgaga ttcgagaagc cgacggagac aagattcgtg   300
tgggggagaa caaccgcgg ggctgagcgc cgttgataig ggatcaacgc gtgtggataa   360
aaaaagtgac gttgatagaa cgtctggcca gtgaaaaaac aaaacaactc caacaaaata   420
cttaaaagc tcttataccc taaatgtagg ggatcaaaca cgtctctaca ctatttagca   480
gcgtcctcta aatgatcctc taaatttaga gaacgctact agattctcta tatatagttt   540
ctctaaacga tcttttatcc atttaaatac tttaaataac cggtttaaca aaactaaaat   600
atatacaata catttgagag tatgacaaat acgtatgtat aaaaataaaa aataaaataa   660
tgtattagtc tactttgaat cttctttct tcataatata atgatgtata gctctcatgt    720
gcgttgagaa aaaagttaga gctagacgtt taatgtgtag tgacagtctt cgacgaaatc   780
tccctaatga gatgaattac tggaggttcc atcagaaagt cccctgaaaa gaggcattta   840
tttagtttag tcagcaattt ctgggaacac aaatattctt ttgttatcac cactattaaa   900
aatctatggt tataacttat aataacatga aaaataatt tagcatccca tatatataaa   960
aactgaagga agccatatat actaacataa gttaggagaa actaagaagg ttgtgcaaag   1020
cttgcactgc tccaaaatac tgcaaacaac cactctcctc taccaaccaa agaaactcat   1080
gtactccctc cgttcttttt tatttgtcgc atttttagttt aaaaatgaac tagcagtcga   1140
caaatattcg agaacagata tagtatatac taacataact taggagatac taagaaagtt   1200
gcgcagagct ttcactgttc caaattactg caaagcctct cccctctgcc agtacatcta   1260
cgagatgttt cagttaaaca aagattcaga caagtgatga gccacttctt gtcatagatt   1320
gtgtggtcaa ccaacccatt gatgccacgg tttttgtcga tccatgcttt tgtattaaaa   1380
catcagttat gtttaccatg tccgatatgc tctacataat gacaatcaac ttggtgttca   1440
ttatatttac aatgttagga atttcaatag ctacgaacac ttcaatagaa gtgcctttgt   1500
gggatcacct taatgtgttg ttgatgtaag gagaagaatc ttaattact cttgctaaat    1560
ttgaactaca caaaaccact gcactgagga ttgtcctaat aaattactgc tcatacacgt   1620
tagcatctgt tcagatactg agctaatccc taggattaaa ggatttgtaa aagatatgcc   1680
caatcattca ttttagttat ttatttctta gttatccact tgaagattta catacatttg   1740
aaataaattt cttagaggta aagtgaaaat cagttattta aatacatttt agttatttat   1800
tttcttcttt ttcctaattt ttccttgtat ttgaagtcg aaaagataac tttgccctta    1860
tacatattt atcttctacg tacgcatctg aacaacgtct ctttgtcccc tgatcgtgca   1920
gcaattagtg ctatgaatcg cgtttaagcg ctgcaaaatc atggctgggg cttcgtcctc   1980
gagtcgtcct gctgctcgat gtcacctcga gtcccgcacc gacctcagtg cttgttcttg   2040
ttggagccac ctctctcgga cgatcgccaa agacggataa ggcgaagcc gtcacttcag    2100
accgcgctca tgcgccgtag cagactccta catgcaggg ccagggtatg tggaccttttg   2160
caagtttagg attgaaccca gcgaccagaa tccacaagat tggagcaaac gaccaaaaat   2220
tcacaaggat tggcggctga cattgccagc gcgggatcgc atgcggcggc ggcggccggg   2280
gcgagcacgg gagcaggcga cagtcggcct ccattggaag gtagaaatac ttaagggcaa   2340
ggtctccaaa tacttgaaaa aataggaaaa agaagaaaat acatgaaatg atattgaaat   2400
caattggaag atgttatgaa tcttgttttt gcaaagcgaa cgattcagat ggcaaaaacta  2460
tgaatctttt tgtttgaagt cccaaatata aaatttctc gtactcacca acattggtgc   2520
gcacctgtga ttggctcata aaaattcttg gagggacgga agaaagagtg aagggataag   2580
caagttttcc cttcatggtt cccgtttgtt tactcaaaca ctgatagttt aaactgaagg   2640
cgggaaacga caatcgatcc atgagcggag aattaaggga gtcacgttat gacccccgcc   2700
gatgacgcgg gacaagccgt tttacgtttg gaactgacag aaccgcaacg ttgaaggagc   2760
cactcagcaa gcttactagt agcgctgttt aaacgctctt caactggaag agcggttacc   2820
cggaccgaag cttgcagtgcc tgcagtgcag cgtgacccgg tcgtgccct ctctagagat    2880
aatgagcatt gcatgtctaa gttataaaaa attaccacat atttttttg tcacacttgt   2940
ttgaagtgca gtttatctat ctttatacat atatttaaac tttactctac gaataatata   3000
atctatagta ctacaataat atcagtgttt tagagaatca tataaatgaa cagttagaca   3060
tggtctaaag gacaattgag tattttgaca acaggactct acagttttat cttttagtg    3120
tgcatgtgtt ctcctttttt tttgcaaata gcttcaccta tataatactt catccattt    3180
attagtacat ccatttaggg tttagggtta atggttttta tagactaatt tttttagtac   3240
atctatttta ttctatttta gcctctaaat taagaaaact aaaactctat tttagttttt   3300
ttatttaata atttagatat aaaatagaat aaaataaagt gactaaaaat taaacaaata   3360
cccttttaaga aattaaaaaa actaaggaaa cattttttctt gtttcgagta gataatgcca   3420
gcctgttaaa cgccgtcgac gagtctaacg gacaccaaac agcgaaccag cagcgtgcgg   3480
tcgggccaag cgaagcagac ggcacggcat ctctgtcgct gcctctggac ccctctcgag   3540
agttccgctc caccgttgga cttgctccgc tgtcggcatc cagaaattgc gtggcggagc   3600
ggcagacgta agcggcacg gcaggcggcc tcctcctcct ctcacggcac cggcagctac   3660
gggggattcc tttcccaccg ctcctcgct ttccttcct cgcccgccgt aataaataga   3720
cacccccctcc acaccctctt tccccaacct cgtgttgttc ggagcgcaca cacacacaac   3780
```

```
cagatctccc ccaaatccac ccgtcggcac ctccgcttca aggtacgccg ctcgtcctcc   3840
ccccccccc ctctctacct tctctagatc ggcgttccgg tccatggtta gggcccggta   3900
gttctacttc tgttcatgtt tgtgttagat ccgtgtttgt gttagatccg tgctgctagc   3960
gttcgtacac ggatgcgacc tgtacgtcag acacgttctg attgctaact tgccagtgtt   4020
tctcttttggg gaatcctggg atggctctag ccgttccgca gacgggatcg atttcatgat   4080
ttttttttgtt tcgttgcata gggtttggtt tgccctttc ctttatttca atatatgccg   4140
tgcacttgtt tgtcgggtca tctttttcatg ctttttttg tcttggttgt gatgatgtgg   4200
tctggttggg cggtcgttct agatcggagt agaattctgt ttcaaactac ctggtggatt   4260
tattaatttt ggatctgtat gtgtgtgcca tacatattca tagttacgaa ttgaagatga   4320
tggatggaaa tatcgatcta ggataggtat acatgttgat gcgggttta ctgatgcata   4380
tacagagatg cttttttgttc gcttggttgt gatgatgtgg tgtggttggg cggtcgttca   4440
ttcgttctag atcggagtag aatactgttt caaactacct ggtgtattta ttaattttgg   4500
aactgtatgt gtgtgtcata catcttcata gttacgagtt taagatggat ggaaatatcg   4560
atgtaggata ggtatacatg ttgatgtggg ttttactgat gcatatacat gatggcatat   4620
gcagcatcta ttcatatgct ctaaccttga gtacctatct attataataa acaagtatgt   4680
tttataatta ttttgatctt gatatacttg gatgatggca tatgcagcag ctatatgtgg   4740
atttttttag ccctgccttc atacgctatt tatttgcttg gtactgtttc ttttgtcgat   4800
gctcaccctg ttgttttggtg ttacttctgc aggtcgactc tagaggatcc acacgacacc   4860
atgtccgccc gcgaggtgca catcgacgtg aacaacaaga ccggccacac cctccagctg   4920
gaggacaaga ccaagctcga cggcggcagg tggcgcacct ccccgaccaa cgtgccaac   4980
gaccagatca agaccttcgt ggccgaatcc aacggcttca tgaccggcac cgagggcacc   5040
atctactact caattaatgg cgaggccgag atcagcctct acttcgacaa cccgttcgcc   5100
ggctccaaca aatacgacgg ccactccaac aagtcccagt acgagatcat cacccagggc   5160
ggctccggca accagtccca cgtgacctac accatccaga ccacctcctc ccgctacggc   5220
cacaagtcct gagtcatgag tcatgagtca gttaacctag acttgtccat cttctggatt   5280
ggcaactta attaatgtat gaaataaaag gatgcacaca tagtgacatg ctaatcacta   5340
taatgtgggc atcaaagttg tgtgttatgt gtaattacta gttatctgaa taaaagagaa   5400
agagatcatc catatttctt atcctaaatg aatgtcacgt gtctttataa ttctttgatg   5460
aaccagatgc atttcattaa ccaaatccat atacatataa atattaatca tatataatta   5520
atatcaattg ggttagcaaa acaaatctag tctaggtgtg ttttgcgaat gcggccgacg   5580
accgaattgg ggatctgcat gaaagaaact gtcgcactgc tgaaccgcac cttgctcactt  5640
tcatcgaaca cgacctgtgc ccaagatgac ggtgctgcgg tctaagtgag gctgaattgc   5700
cttggacaga agcggactcc ctacaattag ttaggcaaaa cggtgcatcc atgtgtagct   5760
ccgggctcgg gctgtatcgc catctgcaat agcatccatg gagctcgttc catgtagttg   5820
gagatgaacc aatgatcggg cgtgtgacg tatgttcctg tgtactccga tagtagagta   5880
cgtgttagct cttttcatggt gcaagtgaaa tttgtgttgg tttaattacc cctacgttag   5940
ttgcgggaca ggagacacat catgaattta aaggcgatga tgtcctctcc tgtaatgtta   6000
ttcttttgat gtgatgaatc aaaatgtcat ataaaacatt tgttgctctt tagttaggcc   6060
tgatcgtaga acgaaatgct cgtgtagcgg ggctacgagc ctatgacgca ataacactgg   6120
tttgccggcc cggagtcgct tgacaaaaaa aagcatgtta agtttattta caattcaaaa   6180
cctaacatat tatattccct caaagcaggt tcacgatcac acctgtacct aaaaaaaaca   6240
tgaagaatat attactccat tattatgaga tgaaccactt ggcaagagtg gtaagctata   6300
taaaaaaatg aacattatta cgagatgtta tatgccatta tattgattcg aagatatatg   6360
tttcttttctc ccacgggcac ctaacggata catgataagg ccaaggcaga tcacgggaaa   6420
ttattcgaat acatgttacg ccctattgcc ggaaaaaaaa tgcagggcag gtgttggccg   6480
tagcgattta agcacttaag ctggaggttg ccacacttgg atgcaagcgt ctgacccttc   6540
taaacatcg gcggctttgt ccgtatccgt atccccatc cgacatctcg ctggccacac   6600
gacgggctg ggcagatcgt ggatgccggg tcgacgtcga tcgtcagcca tcatagacca   6660
atcgaccatc tgttatggat gcttgctagc tagactagtc agacataaaa tttggatact   6720
ttctcccaac tgggagacgg ggactgatgt gcagctgcac gtgagctaaa tttttcccta   6780
taaatatgca tgaaatactg cattatcttg ccacagccac tgccacagcc agataacaag   6840
tgcagctggt agcacgcaac gcatagctct ggacttgtag ctaggtagcc aaccggatcc   6900
acacgacacc atgctcgaca ccaacaaggt gtacgagatc agcaaccacg ccaacggcct   6960
ctacgccgcc acctacctct ccctcgacga ctccggcgtg tccctcatga caagaacga   7020
cgacgacatc gacgactaca acctcaagtg gttcctcttc ccgatcgacg agaccagta   7080
catcatcacc tcctacgccc ccaacaactg caaggtgtgg aacgtgaaca acgacaagat   7140
taatgtgtca acctactcct ccaccaactc catccagaag tggcagatca aggccaacgg   7200
ctcctcctac gtgatccagt ccgacaacgg caaggtgctc accgccggca ccggccaggc   7260
cctcggcctc atccgcctca ccgacgtgctc ctccaacaac ccgaaccagc aatgaaacct   7320
gacgtccgtg cagaccatcc agctcccgca gaagccgatc atcgacacca agctcaagga   7380
ctacccgaag tactccccga ccggcaacat cgacaacggc acctcccgc agctcatggg   7440
ctggaccctc gtgccgtgca tcatggtgaa cgacccgaac atcgacaaga cacccagat   7500
caagaccacc ccgtactaca tcctcaagaa gtaccagtac tggcagaggg ccgtgggctc   7560
caacgtcgcg ctccgcccgc acgagaagaa gtcctcacac tacgagtggg gcaccgagat   7620
cgaccagaag accaccatca tcaacaccct cggcttccag atcaacatcg acagcggcat   7680
gaagttcgac atcccggagg tgggcggcgg taccgacgag atcaagaccc agctcaacga   7740
ggagctcaag atcgagtatt cacatgagac gaagatcatg gagaagtacc aggagcagtc   7800
cgagatcgac aacccgaccg accagtccat gaactccatc ggcttcctca ccatcacctc   7860
cctggagctc taccgctaca ccggctccga gatccgcatc atgcagatcc agacctccga   7920
caacgacacc tacaacgtga cctcctaccc gaaccaccag caggccctgc tgctgctgac   7980
caaccactcc tacgaggagg tggaggagat caccaacatc ccgaagtcca ccctcaagaa   8040
gctcaagaag tactacttct gagtcatgag tcatgagtca gttaacctag acttgtccat   8100
cttctggatt ggcaactta attaatgtat gaaataaaag gatgcacaca tagtgacatg   8160
ctaatcacta taatgtgggc atcaaagttg tgtgttatgt gtaattacta gttatctgaa   8220
taaaagagaa agagatcatc catatttctt atcctaaatg aatgtcacgt gtctttataa   8280
ttctttgatg aaccagatgc atttcattaa ccaaatccat atacatataa atattaatca   8340
tatataatta atatcaattg ggttagcaaa acaaatctag tctaggtgtg ttttgcgaat   8400
tcccatggag tcaagattc aaatagagga cctaacagaa ctcgccgtaa agactggcga   8460
acagttcata cagagtctct tacgactcaa tgacaagaag aaaatcttcg tcaacatggt   8520
```

-continued

```
ggagcacgac acgcttgtct actccaaaaa tatcaaagat acagtctcag aagaccaaag    8580
ggcaattgag acttttcaac aaagggtaat atccggaaac ctcctcggat tccattgccc    8640
agctatctgt cactttattg tgaagatagt ggaaaaggaa ggtggctcct acaaatgcca    8700
tcattgcgat aaaggaaagg ccatcgttga agatgcctct gccgacagtg gtcccaagaa    8760
tggaccccca cccacgagga gcatcgtgga aaaagaagga gttccaacca cgtcttcaaa    8820
gcaagtggat tgatgtgata tctccactga cgtaagggat gacgcacaat cccactatcc    8880
ttcgcaagac ccttcctcta tataaggaag ttcatttcat ttggagagga cagggtaccc    8940
ggggatccac catgtctccg gagaggagac cagttgagat taggccagct acagcagctg    9000
atatggccgc ggtttgtgat atcgttaacc attacattga gacgtctaca gtgaacttta    9060
ggacagagcc acaaacacca caagagtgga ttgatgatct agagaggttg caagatagat    9120
acccttggtt ggttgctgag gttgagggtg ttgtggctgg tattgcttac gctgggccct    9180
ggaaggctag gaacgcttac gattggacag ttgagagtac tgtttacgtg tcacataggc    9240
atcaaaggtt gggcctagga tccacattgt acacacattt gcttaagtct atggaggcgc    9300
aaggttttaa gtctgtgggt gctgttatag gccttccaaa ccgatccatct gttaggttgc    9360
atgaggcttt gggatacaca gcccgggta cattgcgcgc agctggatac aagcatggtg    9420
gatggcatga tgttggtttt tggcaaaggg attttgagtt gccagctcct ccaaggccag    9480
ttaggccagt tacccagatc tgagtcgacc tgcaggcatg cccgctgaaa tcaccagtct    9540
ctctctacaa atctatctct ctctataata atgtgtagt agttcccaga taagggaatt    9600
agggttctta tagggtttcg ctcatgtgtt gagcatataa gaaaccctta gtatgtattt    9660
gtatttgtaa aatacttcta tcaataaaat ttctaattcc taaaaccaaa atccagggcg    9720
agctcggtac ccggggatcc tctagagtcg acctgcaggc atgcccgcgg atatcgatgg    9780
gccccgaccg aagcttcggt ccgggccatc gtggcctctt gctcttcagg atgaagagct    9840
atgtttaaac gtgcaagcgc tcaattcgcc ctatagtgag tcgtattaca atcgtacga    9900
attcagtaca ttaaaaacgt ccgcaatgtg ttattaagtt gtctaagcgt caatttttcc    9960
cttctatggt cccgtttgtt tatcctctaa attatataat ccagcttaaa taagttaaga   10020
gacaaacaaa caacacagat tattaaatag attatgtact ctagatacct agattatgta   10080
atccataagt agaatatcag gtgcttatat aatctatgag ctcgattata taatcttaaa   10140
agaaaacaaa cagagcccct ataaaaaggg gtcaagtgga cacttggtca ctcatttaat   10200
ccctccctct cctcttttat ccctcttttt ggtgtattca ccaatagtgg tgtgcacctg   10260
tgattggctc gtaaaaattc ttggacggat ggaagagtga agagataagc aagtcaaaga   10320
aaagtaacaa cgaagcttca tcagctacaa attttggccc aactggttgc accagcacca   10380
aacttacgta tacatgatta tctcctgttc cctcatttcg aagaaaaaa cgggtttcaa   10440
aaacccactgc tttcaggagt aaaaaaagat aataatctga aacattgctt ccaccttggc   10500
ccttatttgg ttacgttgca attcaccca atccacatgt ggattgagat ggattgcagt   10560
gtagctagac aaaaccttag gccctgtttg cataggaata caccaggaat tattccagct   10620
aatcaaaatt tatataaatg agagaaacaa ttcggatagg aattgttcca ggacttcatt   10680
ctgcagtaac cgaacggccc cttaatccac cccaatacac gtggattgga gtggattgag   10740
gtacagccaa acaaggccta agtgcagatc aaatataatca cccgtcatat tcttctacct   10800
acaaaaacag caataaacac ctgaatgaag ttctaatttg cacagtgtag gtaggatgaa   10860
aatagttacc tcctcatggt cagtaactct tggcacacaa cttcacatgt aatcgatgta   10920
ccacttggct cttgcctgaa acccaataca tctttagcat aagaataata ttatgatggc   10980
aaggcatgat caccagcact cctttattgt ttagtaagtc tatcactccc caaaacaatt   11040
caaatgaaca gagatgcatt gcccccaatg aattctattt caattagccg gaaaattcta   11100
cttcatcaga agcatccaaa ttgccagcat ccctactaga ctgaccatga ccaggctgcc   11160
gcagatgcct cttttttctgt cctctcctct ttgcttgag tttctcttca agatccctca   11220
ccccacgtct cttatacatc ttaaagctaa catgtctctc ctccgccatc ttcctaacct   11280
tctcagtaat ctcagcagca atctgacggt tgtacaactt cttcagcccc ttcatcaact   11340
ttgcaaatgt gtcaggctgt ggcatcagtc ctgcctctag catgtctaag caatacaggc   11400
aggcctcctt gacatgtttc ttcgcaaaca gtgcatgaat ccagatagtc catgcactca   11460
cattgagctc acagcctttg ctcacaatac atttccaaac atcctttgca agctcaagtt   11520
tctcatctct gaccaacgca ttgaggaggt ccttcagcac cccatattgc ggtaccacaa   11580
agagccccct cccaaccatg tctttaaat aactacatgc ctcaatcagc aaaccctgcc   11640
caacaaggcc actcaccacg atagcaaatg tatcgaccac aggactgagc ccagcacttt   11700
ccatctcatt ccacaatgtc atggcttgct ggtctcccc aagcctgcag gccaaccgaa   11760
tcaccacatt gtatatcttg agatctggtg gacaccggca ctcccgcatc ctctccatca   11820
gctccaagca ctcctcaagc tgctccttct tctcgtgtgc tacaaagaaa ccatggtaca   11880
cggcagcgtc cacccgcagg ccatccctcg acatagcatc caagaactcg tacccctggg   11940
at                                                                  11942
```

```
SEQ ID NO: 18           moltype = AA   length = 1307
FEATURE                 Location/Qualifiers
source                  1..1307
                        mol_type = protein
                        organism = unidentified SEQUENCE: 18
MTQFEGFTNL YQVSKTLRFE LIPQGKTLKH IQEQGFIEED KARNDHYKEL KPIIDRIYKT    60
YADQCLQLVQ LDWENLSAAI DSYRKEKTEE TRNALIEEQA TYRNAIHDYF IGRTDNLTDA   120
INKRHAEIYK GLFKAELFNG KVLKQLGTVT TTEHENALLR SFDKFTTYFS GFYENRKNVF   180
SAEDISTAIP HRIVQDNFPK FKENCHIFTR LITAVPSLRE HFENVKKAIG IFVSTSIEEV   240
FSFPFYNQLL TQTQIDLYNQ LLGGISREAG TEKIKGLNEV LNLAIQKNDE TAHIIASLPH   300
RFIPLFKQIL SDRNTLSFIL EEFKSDEEVI QSFCKYKTLL RNENVLETAE ALFNELNSID   360
LTHIFISHKK LETISSALCD HWDTLRNALY ERRISELTGK ITKSAKEKVQ RSLKHEDINL   420
QEIISAAGKE LSEAFKQKTS EILSHAHAAL DQPLPTTLKK QEEKEILKSQ LDSLLGLYHL   480
LDWFAVDESN EVDPEFSARL TGIKLEMEPS LSFYNKARNY ATKKPYSVEK FKLNFQMPTL   540
ASGWDVNKEK NNGAILFVKN GLYYLGIMPK QKGRYKALSF EPTEKTSEGF DKMYYDYFPD   600
AAKMIPKCST QLKAVTAHFQ THTTPILLSN NFIEPLEITK EIYDLNNPEK EPKKFQTAYA   660
KKTGDQKGYR EALCKWIDFT RDFLSKYTKT TSIDLSSLRP SSQYKDLGEY YAELNPLLYH   720
ISFQRIAEKE IMDAVETGKL YLFQIYNKDF AKGHHGKPNL HTLYWTGLFS PENLAKTSIK   780
LNGQAELFYR PKSRMKRMAH RLGEKMLNKK LKDQKTPIPD TLYQELYDYV NHRLSHDLSD   840
```

```
EARALLPNVI TKEVSHEIIK DRRFTSDKFF FHVPITLNYQ AANSPSKFNQ RVNAYLKEHP    900
ETPIIGIDRG ERNLIYITVI DSTGKILEQR SLNTIQQFDY QKKLDNREKE RVAARQAWSV    960
VGTIKDLKQG YLSQVIHEIV DLMIHYQAVV VLENLNFGFK SKRTGIAEKA VYQQFEKMLI   1020
DKLNCLVLKD YPAEKVGGVL NPYQLTDQFT SFAKMGTQSG FLFYVPAPYT SKIDPLTGFV   1080
DPFVWKTIKN HESRKHFLEG FDFLHYDVKT GDFILHFKMN RNLSFQRGLP GFMPAWDIVF   1140
EKNETQFDAK GTPFIAGKRI VPVIENHRFT GRYRDLYPAN ELIALLEEKG IVFRDGSNIL   1200
PKLLENDDSH AIDTMVALIR SVLQMRNSNA ATGEDYINSP VRDLNGVCFD SRFQNPEWPM   1260
DADANGAYHI ALKGQLLLNH LKESKDLKLQ NGISNQDWLA YIQELRN                 1307

SEQ ID NO: 19           moltype = DNA   length = 40
FEATURE                 Location/Qualifiers
source                  1..40
                        mol_type = other DNA
                        organism = synthetic construct
SEQUENCE: 19
ggataagcaa gtaaaagcgc tcaaacactg atagtttaaa                           40

SEQ ID NO: 20           moltype = DNA   length = 2593
FEATURE                 Location/Qualifiers
source                  1..2593
                        mol_type = other DNA
                        organism = synthetic construct
SEQUENCE: 20
ctgagcgcac aacagcgagt cgcatggcac cggacgacat gagcgagatt tagatcggag     60
ggtgcggaca tggggcaacc tgcgcagcta acgcagggat ccacgcgacc accaacgaag    120
ccaagcccgg gcacgtcccc aggcaggttg ggccctggtt ccaccagcgg atgcatgcag    180
tgaagcgggg acggagagac aagccgaggg cgcgggtggg aatggcgtcc gggaggacga    240
gtggaggaga agaatctaga ggcatcgaga ttcgagaagc cgacggagac aagattcgtg    300
tgggggggaga caaaccgcgg ggctgagcgc cgttgatatg ggatcagacg gtgtggataa    360
aaaagtgac gttgatagaa cgtctggcca gtgaaaaaac aaaacaactc caacaaaata    420
ctttaaaagc tcttataccc taaatgtagg ggatcaaaca cgtctctaca ctatttagca    480
gcgtcctcta aatgatcctc taaatttaga gaactgctact agttctctca tatatagtta    540
ctctaaacga tctttttatcc atttaaataa tttaaataac cggtttaaca aaactaaaat    600
atatacaata catttgagag tatgacaaat acgtatgtat aaaaataaaa aataaaataa    660
tgtattagtc tactttgaat cttcttttct tcataatata atgatgtata gctctcatgt    720
gcgttgagaa aaaagttaga gctagacgtt taatgtgtag tgacagtctt cgacgaaatc    780
tccctaatga gatgaattac tggaggttcc atcagaaagt cccctgaaaa gaggcattta    840
tttagtttag tcagcaattt ctgggaacac aaatattcct ttgttatcac cactattaaa    900
aatctatggt tataacttat aataacatga aaaaataatt tagcatccca tatatataaa    960
aactgaagga agccatatat actaacataa gttaggagaa actaagaagg ttgtgcaaag   1020
cttgcactgc tccaaaatac tgcaaacaac cactctcctc taccaaccaa agaaactcat   1080
gtactccctc cgttcttttt tatttgtcgc atttagttt aaaaatgaac tagcagtcga   1140
caaatattcg agaacagata tagtatatac taacataact taggagatac taagaaagtt   1200
gcgcagagct ttcactgttc caaattactg caaagcctct cccctctgcc agtacatcta   1260
cgagatgttt cagttaaaca aagattcaga caagtgatga gccacttctt gtcatagatt   1320
gtgtggtcaa ccaacccatt gatgccacgg ttttgtgca tccatgcttt tgtattaaaa   1380
catcagttat gtttaccatg tccgatatgc tctacataat gacaatcaac ttggtgttca   1440
ttatatttac aatgttagga atttcaaatg ctacgaacca ttcaatagaa gtgccttttg   1500
gggatcacct taatgtgttg ttgatgtaag agaagaaatc ttaattttact cttgctaaat   1560
ttgaactaca caaaccact gcactgagga ttgtcctaat aaaattactgc tcatacacgt   1620
tagcatctgt tcagatactg agctaatccc taggattaaa ggatttgtaa aagatatgcc   1680
caatcattca ttttagttat ttatttctta gttatccact tgaagattta catacatttg   1740
aaataaattt cttagaggta aagtgaaaat cagttattta aatacatttt agttatttat   1800
tttcttcttt ttcctaattt tccttgtat ttgaagtctg aaaagataac tttgcccttta   1860
tacatatttt atcttctacg tacgcatctg aacaacgtct ctttgtcccc tgatcgtgca   1920
gcaattagtg ctatgaatcg cgtttaagcg ctgcaaaatc atggctgggg cttcgtcctc   1980
gagtcgtcct gctgctcgat gtcacctcga gtcccgcacc gacctcagtg cttgttcttg   2040
ttggagccac ctctctcgga cgatcgccca agacggataa ggccgaagcc gtcacttcag   2100
accgcgctca tgcgccgtag cagactccta catgcgggc ccagggtatg tggaccttg   2160
caagtttagg attggaacca gcgaccagaa tccacaagat tggagcaaac gaccaaaaat   2220
tcacaaggat tggcggctga cattgccagc gcgggatcgc atgcggcggc ggcggccggg   2280
gcgagcacgg gagcaggcga cagtcgagct ccattggaac gtagaaatac ttaagggcaa   2340
ggtctccaaa tacttgaaaa aataggaaaa agaagaaaat acatgaaatg atattgaaat   2400
caattggaag atgttatgaa tcttgttttt gcaaagcgaa cgattcagat ggcaaaacta   2460
tgaatctttt tgtttgaagt cccaaatata aaatttctc gtactcacca acattggtgc   2520
gcacctgtga ttggctcata aaaattcttg gagggacgga agaaagagtg aagggataag   2580
caagtaaaag cgc                                                    2593

SEQ ID NO: 21           moltype = DNA   length = 40
FEATURE                 Location/Qualifiers
source                  1..40
                        mol_type = other DNA
                        organism = synthetic construct
SEQUENCE: 21
agttgtctaa gcgtcaattt ttcccttcta tggtcccgtt                           40
```

```
SEQ ID NO: 22            moltype = DNA  length = 1986
FEATURE                  Location/Qualifiers
source                   1..1986
                         mol_type = other DNA
                         organism = synthetic construct
SEQUENCE: 22
ttcccttcta tggtcccgtt tgtttatcct ctaaattata taatccagct taaataagtt    60
aagagacaaa caaacaacac agattattaa atagattatg taatctagat acctagatta   120
tgtaatccat aagtagaata tcaggtgctt atataatcta tgagctcgat tatataatct   180
taaaagaaaa caaacagagc ccctataaaa aggggtcaag tggacacttg gtcactcatt   240
taatccctcc ctctcctctt ttatccctct ttttggtgta ttcaccaata gtggtgtgca   300
cctgtgattg gctcgtaaaa attcttggac ggatggaaga gtgaagagat aagcaagtca   360
aagaaaagta acaacgaagc ttcatcagct acaaattttg gcccaactgg ttgcaccagc   420
accaaactta cgtatacatg attatctctg tttccctcat ttcgaagaaa aaacgggtt    480
tcaaaaccca ctgctttcag gagtaaaaaa agataataat ctgaaacatt gcttccacct   540
tggcccttat ttggttacgt tgcaattcac cccaatccac atgtggattg agatggattg   600
cagtgtagct agacaaaccc ttaggccctg tttgcatagg aatacaccag gaattattcc   660
agctaatcaa aatttatata aatgagagaa acaattcgga taggaattgt tccaggactt   720
cattctgcag taaccgaacg gccccttaat ccaccccaat acacgtggat ggagtggat    780
tgaggtacag ccaaacaagg cctaagtgca gatcaaataa atcaccgtc atattcttct   840
acctacaaaa acagcaataa cacctgaat gaagttctaa tttgcacagt gtaggtagga   900
tgaaaatagt tacctcctca tggtcagtaa ctcttggcac acaacttcac atgtaatcga   960
tgtaccactt ggctcttgcc tgaaacccaa tacatcttta gcataagaat aatattatga  1020
tggcaaggca tgatcaccag cactcctta ttgtttagta agtctatcac tccccaaaac  1080
aattcaaatg aacagagatg cattgccccc aatgaattct atttcaatta gccggaaaat  1140
tctacttcat cagaagcatc caaattgcca gcatccctac tagactgacc atgaccaggc  1200
tgccgcagat gcctcttttt ctgtcctctc ctctttgcct tgagtttctc ttcaagatcc  1260
ctcaccccac gtctcttata catcttaaag ctaacatgtc tctcctccgc catcttccta  1320
accttctcag taatctcagc agcaatctga cggttgtaca acttcttcag cccccttcatc  1380
aactttgcaa atgtgtcagg ctgtggcatc agtcctgcct ctagcatgtc taagcaatac  1440
aggcaggcct ccttgacatg tttcttcgca aacagtgcat gaatccagat agtccatgca  1500
ctcacattga gctcacagcc tttgctcaca atacatttcc aaacatccttt gcaagctca  1560
agtttctcat ctctgaccaa cgcattgagg aggtccttca gcccccata ttgcggtacc  1620
acaaagagcc ccctcccaac catgtcttta aaataactac atgcctcaat cagcaaaccc  1680
tgcccaacaa ggccactcac cacgatagca aatgtatcga ccacaggact gagcccagca  1740
cttccatct cattccacaa tgtcatggct tgcttggtct ccccaagcct gcaggccaac   1800
cgaatcacca cattgtatat cttgagatct ggtggacacc ggcactccg catcctctcc  1860
atcagtcca agcactcctc aagctgctcc ttcttctcgt gtgctacaaa gaaaccatgg  1920
tacacggcag cgtccaccg caggccatcc ctcgacatag catccaagaa ctcgtacccc  1980
tgggat                                                                1986

SEQ ID NO: 23            moltype = DNA  length = 11915
FEATURE                  Location/Qualifiers
source                   1..11915
                         mol_type = other DNA
                         organism = synthetic construct
SEQUENCE: 23
ctgagcgcac aacagcgagt cgcatggcac cggacgacat gagcgagatt tagatcggag    60
ggtgcggaca tggggcaacc tgcgcagcta acgcagggat ccacacgacc accaacgaag   120
ccaagcccgg gcacgtcccc aggcaggttg ggccctgctt ccaccagcgg atgcatgcag   180
tgaagcgggg acggagagac aagccgaggg cgcgggtggg aatggcgtcc gggaggacga   240
gtggaggaga gaatctaga ggcatcgaga ttcgagaagc cgacggagac aagattcgtg    300
tgggggggaga caaaccgcgg ggctgagcgc cgttgatatg ggatcagacg gtgtggataa   360
aaaaagtgac gttgatagaa cgtctggcca gtgaaaaac aaaacaactc caacaaaata   420
cttttaaagc tcttataccc taaatgtagg ggatcaaaca cgtctctaca ctatttagca   480
gcgtcctcta aatgatcctc taaatttaga gaacgctact agattctcta tatatagttt   540
ctctaaacga tcttttatcc atttaaatac tttaaataac cggtttaaca aaactaaaat   600
atatacaata catttgagag tatgacaaat acgtatgtat aaaaataaaa aataaaataa   660
tgtattagtc tactttgaat cttctttct tcataaataa atgatgtata gctctcatgt    720
gcgttgagaa aaaagttaga gctagacgtt taatgtgtag tgacagtctt cgacgaaatc   780
tccctaatga gatgaattac tggaggttcc atcagaaagt cccctgaaaa gaggcattta   840
tttagtttag tcagcaattt ctgggaacac aaatattctt ttgttatcac cactattaaa   900
aatctatggt tataacttat aataacatga aaaaataatt tagcatccca tatatataaa   960
aactgaagga agccatatat actaacataa gttaggagaa actaagaagg ttgtgcaaag  1020
cttgcactgc tccaaaatac tgcaacaac cactctcctc taccaaccaa agaaactcat  1080
gtactccctc cgttctttt tatttgtcgc atttagttt aaaaatgaac tagcagtcga  1140
caaatattcg agaacagata tagtatatac taacataact taggagatac taagaaagtt  1200
gcgcagagct ttcactgttc caaattactg caaagcctct ccctctgcc agtacatcta  1260
cgagatgttt cagttaaaca aagattcaga caagtgatga gccacttctt gtcatagatt  1320
gtgtggtcaa ccaacccatt gatgccacgg ttttgtgca tccatgcttt tgtattaaaa  1380
catcagttat gtttaccatg tccgatatgc tctacataat gacaatcaac ttggtgttca  1440
ttatatttac aatgttagga atttcaatag ctacgaacac ttcaatagaa gtgcctttgt  1500
gggatcacct taatgtgttg ttgatgtaag gagaagaatc ttaatttact cttgctaaat  1560
ttgaactaca caaaaccact gcactgagga ttgtcctaat aaattactgc tcatacacgt  1620
tagcatctgt tcagatactg agctaatccc taggattaaa ggatttgtaa aagatatgcc  1680
caatcattca ttttagttat ttatttctta gttatccact tgaagattta catacatttg  1740
aaataaattt cttagaggta aagtgaaaat cagttattta aatacatttt agttatttat  1800
ttcttcttt tcctaatttt ttccttgtat ttgaagtctg aaaagataac tttgcccttta  1860
```

```
tacatattttt atcttctacg tacgcatctg aacaacgtct cttttgtccc tgatcgtgca   1920
gcaattagtg ctatgaatcg cgtttaagcg ctgcaaaatc atggctgggg cttcgtcctc   1980
gagtcgtcct gctgctcgat gtcacctcga gtcccgcacc gacctcagtg cttgttcttg   2040
ttggagccac ctctctcgga cgatcgccaa agacggataa ggccgaagcc gtcacttcag   2100
accggcgctca tgcgccgtag cagactccta catagcaggg ccagggtatg tggacctttg   2160
caagtttagg attggaacca gcgaccagaa tccacaagat tggagcaaac gaccaaaaat   2220
tcacaaggat tggcggctga cattgccagc gcgggatcgc atgcggcggc ggcggccggg   2280
gcgagcacgg gagcaggcga cagtcgagct ccattgaaac gtagaaatac ttaagggcaa   2340
ggtctccaaa tacttgaaaa aataggaaaa agaagaaaat acatgaaatg atattgaaat   2400
caattggaag atgttatgaa tcttgttttt gcaaagcgaa cgattcagat ggcaaaacta   2460
tgaatctttt tgtttgaagt cccaaatata aaatttctc gtactcacca acattggtgc   2520
gcacctgtga ttggctcata aaaattcttg gagggacgga agaaagagtg aagggataag   2580
caagtaaaag cgctcaaacg tttaaactga aggcgggaaa cgacaatctg atcatgagcg   2640
gagaattaag ggagtcacgt tatgaccccc gccgatgacg cgggacaagc cgttttacgt   2700
ttggaactga cagaaccgca acgttgaagg agccactcag caagcttact agtagcgctg   2760
tttaaacgct cttcaactgg aagagcggtt acccggaccg aagcttgcat gcctgcagtg   2820
cagcgtgacc cggtcgtgcc cctctctaga gataatgagc attgcatgtc taagttataa   2880
aaaattacca catattttt ttgtcacact tgtttgaagt gcagtttatc tatctttata   2940
catatattta aactttactc tacgaataat ataatctata gtactacaat aatatcagtg   3000
ttttagagaa tcatataaat gaacagttag acatggtcta aaggacaatt gagtattttg   3060
acaacaggac tctacagttt tatcttttta gtgtgcatgt gttctccttt ttttttgcaa   3120
atagcttcac ctatataata cttcatccat tttattagta catccatttta gggtttaggg   3180
ttaatggttt ttatagacta attttttttag tacatctatt ttattctatt ttagcctcta   3240
aattaagaaa actaaaactc tattttagtt tttttattta ataatttaga tataaaatag   3300
aataaaaataa agtgactaaa aattaaacaa ataccctta agaaattaaa aaaactaagg   3360
aaacattttt cttgtttcga gtagataatg ccagcctgtt aaacgccgtc gacgagtcta   3420
acggacacca accagcgaac cagcagcgtc gcgtcgggcc aagcgaagca gacggcacgg   3480
catctctgtc gctgcctctg gacccctctc gagagttccg ctccaccgtt ggacttgctc   3540
cgctgtcggc atccagaaat tgcgtggcgg agcggcagac gtgagccggc acggcaggcg   3600
gcctcctcct cctctcacgg caccggcagc tacggggagt tcctttccca ccgctccttc   3660
gctttccctt cctcgcccgc cgtaataaat agacacccc tccacaccct cttttcccaa   3720
cctcgtgttg ttcggagcgc acacacacac aaccagatct cccccaaatc cacccgtcgg   3780
cacctccgct tcaaggtacg ccgctcgtcc tccccccccc ccctctcta ccttctctag   3840
atcggcgttc cggtccatgg ttagggcccg gtagttctac ttctgttcat gtttgtgtta   3900
gatccgtgtt tgtgttagat ccgtgctgct agcgttcgta cacgatgcg acctgtacgt   3960
cagacacgtt ctgattgcta acttgccagt gtttctcttt ggggaatcct gggatggctc   4020
tagccgttcc gcagacggga tcgatttcat gatttttttt gtttcgttgc ataggggtttg   4080
gtttgccctt ttccttttatt tcaatatatg ccgtgcactt gtttgtcggg tcatcttttc   4140
atgcttttt ttgtcttggt tgtgatgatg tggtctggtt gggcggtcgt tctagatcgg   4200
agtagaattc tgtttcaaac tacctggtgg atttattaat tttggatctg tatgtgtgtg   4260
ccatacatat tcatagttac gaattgaaga tgatggatgg aaatatcgat ctaggatagg   4320
tatacatgtt gatgcgggtt ttactgatgc atatacagag atgcttttg ttcgcttggt   4380
tgtgatgatg tggtggttg gggcggtcgt tcattcgttc tagatcggag tagaatactg   4440
tttcaaacta cctggtgtat ttattaattt tggaactgta tgtgtgtgtc atacatcttc   4500
atagttacga gtttaagatg gatgaaata tcgatgtagg ataggtatac atgttgatgt   4560
gggttttact gatgcatata catgatggca tatgcagcat ctattcatat gctctaacct   4620
tgagtaccta tctattataa taaacaagta tgttttataa ttatttttgat cttgatatac   4680
ttggatgatg gcatatgcag cagctatatg tggatttttt tagccctgcc ttcatacgct   4740
atttatttgc ttggtactgt ttcttttgtc gatgctcacc ctgttgtttg gtgttacttc   4800
tgcaggtcga ctctagagga tccacacgac accatgtccg cccgcgaggt gcacatcgac   4860
gtgaacaaca agaccggcca caccctccag ctggaggaca agacaagct cgacggcggc   4920
aggtggcgca cctccccgac caacgtggcc aacgaccaga tcaagacctt cgtggccgaa   4980
tccaacggct tcatgaccgg caccgagggc accatctact actcaattaa tggcgaggcc   5040
gagatcagcc tctacttcga caacccgttc gccggctcca caaatacga cggccactcc   5100
aacaagtccc agtacgagat catcacccag ggcggcgtcc gcaaccagtc ccacgtgacc   5160
tacaccatcc agaccacctc ctcccgctac ggccacaagt cctgagtcat gagtcatgag   5220
tcagttaacc tagacttgtc catcttctgg attggcaaac ttaattaatg tatgaaataa   5280
aaggatgcac acatagtgac atgctaatca ctataatgtg ggcatcaaag ttgtgtgtta   5340
tgtgtaatta ctagttatct gaataaaaga gaaagagatc atccatattt cttatcctaa   5400
atgaatgtca cgtgtcttta taattctttg atgaaccaga tgcatttcat taaccaaatc   5460
catatacata taaatattaa tcatatataa ttaatatcaa ttgggttagc aaaacaaatc   5520
tagtctaggt gtgttttgcg aatgcggccg cggaccgaat tggggatctg catgaaagaa   5580
actgtcgcac tgctgaaccg cacccttgtca ctttcatcga acacgacctg tgcccaagat   5640
gacggtgctg cggtctaagt gaggctgaat tgccttggac agaagcggac tccctacaat   5700
tagttaggcc aaaacggtgca tccatgtgta gctccgggct cgggctgtat cgccatctgc   5760
aatagcatcc atggagctcg ttccatgtag ttggagatga accaatgatc gggcgtgtgg   5820
acgtatgttc ctgtgtactc cgatagtaga gtacgtgtta gctctttcat ggtgcaagtg   5880
aaatttgtgt tggtttaatt acccctacgt tagttgcggg acaggagaca catcatgaat   5940
ttaaaggcga tgatgtcctc tcctgtaatg ttattctttt gatgtgatga atcaaaatgt   6000
catataaaac atttgttgct ctttagttag gcctgatcgt agaacgaaat gctcgtgtag   6060
cggggctacg agcctatgac gcaataacac tggtttgccg gccgagtc gcttgacaaa   6120
aaaaagcatg ttaagtttat ttacaattca aacctaaca tattatattc cctcaaagca   6180
ggttcacgat cacacctgta cctaaaaaaa acatgaagaa tatattactc cattattatg   6240
agataacca cttggcaaga gtggtaagct atataaaaaa atgaacatta ttacgagatg   6300
ttatatgcca ttatattgat tcgaagatat atgtttcttt ctcccacggg cacctaacgg   6360
atacatgata aggccaaggc agatcacggg aaattattcg aatacatgtt acgcctatt   6420
gccgaaaaaa aaatgcaggg caggtgttgg ccgtagcgat ttaagcactt aagctggagg   6480
ttgccacact tggatgcaag cgtctgaccc ttctaaaaca tcggcggctt tgtccgtatc   6540
cgtatcccct atccgacatc tagctggcca cacgacgggg ctgggcagat cgtggatgcc   6600
```

```
gggtcgacgt cgatcgtcag ccatcataga ccaatcgacc atctgttatg gatgcttgct    6660
agctagacta gtcagacata aaatttggat acttctctcc aactgggaga cggggactga    6720
tgtgcagctg cacgtgagct aaatttttcc ctataaatat gcatgaaata ctgcattatc    6780
ttgccacagc cactgccaca gccagataac aagtgcagct ggtagcacgc aacgcatagc    6840
tctggacttg tagctaggta gccaaccgga tccacacgac accatgctcg acaccaacaa    6900
ggtgtacgag atcagcaacc acgccaacgg cctctacgcc gccacctacc tctccctcga    6960
cgactccggc gtgtcctca tgaacaagaa cgacgacgac atcgacgact acaacctcaa    7020
gtggttcctc ttcccgatcg acgacgacca gtacatcatc acctcctacg ccgccaacaa    7080
ctgcaaggtg tggaacgtga acaacgacaa gattaatgtg tcaacctact cctccaccaa    7140
ctccatccag aagtggcaga tcaaggccaa cggctcctcc tacgtgatcc agtccgacaa    7200
cggcaaggtg ctcaccgccg gcaccggcca ggccctcggc ctcatccgcc tcaccgacga    7260
gtcctccaac aacccgaacc agcaatgaa cctgacgtcc gtgcagacca tccagctccc    7320
gcagaagccg atcatcgaca ccaagctcaa ggactaccg aagtactccc cgaccggcaa    7380
catcgacaac ggcacctccc cgcagctcat gggctggacc ctcgtgccgt gcatcatggt    7440
gaacgacccg aacatcgaca agaacaccca gatcaagacc accccgtact acatcctcaa    7500
gaagtaccag tactggcaga gggccgtggg ctccaacgtc gcgctccgcc cgcacgagaa    7560
gaagtcctac acctacgagt ggggcaccga gatcgaccag aagaccacca tcatcaacac    7620
cctcggcttc cagatcaaca tcgacgacgg catgaagttc gacatcccgg aggtgggcgg    7680
cggtaccgac gagatcaaga cccagctcaa cgaggagctc aagatcgagt attcacatga    7740
gacgaagatc atcgagaagt accaggagca gtccgagatc gacaacccga ccgaccagtc    7800
catgaactcc atcggcttcc tcaccatcac ctccctggag ctctaccgct acaacggctc    7860
cgagatccgc atcatgcaga tccagacctc cgacaacgac acctacaacg tgacctccta    7920
cccgaaccac cagcaggccc tgctgctgct gaccaaccac tcctacgagg aggtggagga    7980
gatcaccaac atcccgaagt ccaccctcaa gaagctcaag aagtactact tctgagtcat    8040
gagtcatgag tcagttaacc tagacttgtc catcttctgg attggccaac ttaattaatg    8100
tatgaaataa aaggatgcac atatagtgac atgctaatca ctataatgtg ggcatcaaag    8160
ttgtgtgtta tgtgtaatta ctagttatct gaataaaaga gaaagagatc atccatattt    8220
cttatcctaa atgaatgtca cgtgtcttta taattcttg atgaaccaga tgcatttcat    8280
taaccaaatc catatacata taaatattaa tcatatataa ttaatatcaa ttgggttagc    8340
aaaacaaatc tagtctaggt gtgttttgcg aattcccata gagtcaaaga ttcaaataga    8400
ggacctaaca gaactcgccg taaagactgg cgaacagttc atacagagtc tcttacgact    8460
caatgacaag aagaaaatct tcgtcaacat ggtggagcac gacacgcttg tctactccaa    8520
aaatatcaaa gatacagtct cagaagacca aagggcaatt gagactttc aacaaagggt    8580
aatatccgga aacctcctcg gattccattg cccagctatc tgtcacttta ttgtgaagat    8640
agtggaaaag gaaggtggct cctacaaatg ccatcattgc gataaaggaa aggccatcgt    8700
tgaagatgcc tctgccgaca gtggtccaa agatggaccc ccaccacga ggagcatcgt    8760
ggaaaaagaa gacgttccaa ccacgtcttc aaagcaagtg gattgatgtg atatctccac    8820
tgacgtaagg gatgacgcac aatcccacta tccttcgcaa gacccttcct ctatataagg    8880
aagttcattt catttggaga ggacagggta cccggggatc caccatgtct ccggagagga    8940
gaccagttga gattaggcca gctacagcag ctgatatgcc cgcggtttgt gatatcgtta    9000
accattacat tgagacgtct acagtgaact ttaggacaga gccacaaaca ccacaagagt    9060
ggattgatga tctagagagg ttgcaagata gatacccttg gttggttgct gaggttgagg    9120
tgtgttggc tggtattgct tacgctgggc cctggaaggc taggaacgct tacgattgga    9180
cagttgagag tactgtttac gtgtcacata ggcatcaaag gttgggccta ggatccacat    9240
tgtacacaca tttgcttaag tctatggagg cgcaaggttt taagtctgtg gttgctgtta    9300
taggcctttc aaacgatcca tctgttaggt tgcatgaggc tttgggatac acagcccggg    9360
gtacattgcg cgcagctgga tacaagcagt gtggatggca tgatgttggt ttttggcaaa    9420
gggattttga gttgccagct cctccaaggc cagttaggcc agttaccag atctgagtcg    9480
acctgcaggc atgcccgctg aaataccag tctctctcta caaatctatc tctctctata    9540
ataatgtgtg agtagttccc agataaggga attagggttc ttatagggtt tcgctcatgt    9600
gttgagcata taagaaaccc ttagtatgta tttgtatttg taaaatactt ctatcaataa    9660
aatttctaat tcctaaaacc aaaatccagg gcgagctcgg tacccgggga tcctctagag    9720
tcgacctgca ggcatgcccg cggatatcga tgggccccgg ccgaagcttc ggtccgggcc    9780
atcgtggcct cttgctcttc aggatgaaga gctatgttta aacgtgcaag cgctcaattc    9840
gccctatagt gagtcgtatt acaatcgtac gcaattcagt acattaaaaa cgtccgcaat    9900
gtgttattaa gttgtctaag cgtcaatttt tcccttctat ggtccgtttt gtttatcctc    9960
taaattatat aatccagctt aaataagtta agagacaaac aaacaacaca gattattaaa   10020
tagattatgt aatctagata cctagattat gtaatccata agtagaatat caggtgctta   10080
tataatctat gagctcgatt atataatctt aaaagaaaac aaacagagcc cctataaaaa   10140
ggggtcaagt ggacacttgg tcactcattt aatccctccc tctcctcttt tatccctctt   10200
tttggtgtat tcaccaatag tggtgtgcac ctgtgattgg ctcgtaaaaa ttcttggacg   10260
gatgaagag tgaagagata agcaagtcaa agaaaagtaa caacgaagct tcatcagcta   10320
caaatttgg cccaactggt tgcaccagca ccaaacttac gtatacatga ttatctctgt   10380
ttccctcatt tcgaagaaaa aacgggttt caaaacccac tgctttcaag agtaaaaaaa   10440
gataataatc tgaaacattg cttccacctt ggcccttatt tggttacgtt gcaattcacc   10500
ccaatccaca tgtggattga gatggattgc agtgtagcta gacaaccct taggcctgt   10560
ttgcatagga atacaccagg aattattcca gctaatcaaa atttatataa atgagagaaa   10620
caattcggat aggaattgtt ccaggacttc atttctgcagt aaccgaacgg cccttaatc   10680
caccccaata cacgtggatt ggagtggatt gaggtacagc caaacaggc ctaagtcag   10740
atcaaataaa tcacccgtca tattcttcta cctacaaaa cagcaataaa cacctgaatg   10800
aagttctaat ttgcacagtg taggtaggat gaaaatagtt acctcctcat ggtcagtaac   10860
tcttggcaca caacttcaca tgtaatcgat gtaccacttg gctcttgcct gaaacccaat   10920
acatctttag cataagaata atattatgat ggcaaggcat gatcaccagc actcctttat   10980
tagtaa atctactact cccccaaaaca attcaaatga acagagatgc attgccccca   11040
atgaattcta tttcaattag ccggaaaatt ctacttcatc agaagcatcc aaattgccag   11100
catccctact agactgacca tgaccaggct gccgcagatg cctctttttc tgtcctctcc   11160
tctttgcctt gagtttctct tcaagatccc tcaccccacg tctcttatac atcttaaagc   11220
taacatgtct ctcctccgcc atcttcctaa cctttctcagt aatctcagca gcaatctgac   11280
ggttgtacaa cttcttcagc cccttcatca actttgcaaa tgtgtcaggc tgtggcatca   11340
```

```
gtcctgcctc tagcatgtct aagcaataca ggcaggcctc cttgacatgt ttcttcgcaa    11400
acagtgcatg aatccagata gtccatgcac tcacattgag ctcacagcct ttgctcacaa    11460
tacatttcca aacatccttt gcaagctcaa gtttctcatc tctgaccaac gcattgagga    11520
ggtccttcag caccccatat tgcggtacca caaagagccc cctcccaacc atgtctttaa    11580
aataactaca tgcctcaatc agcaaaccct gcccaacaag gccactcacc acgatagcaa    11640
atgtatcgac cacaggactg agcccagcac tttccatctc attccacaat gtcatggctt    11700
gcttggtctc cccaagcctg caggccaacc gaatcaccac attgtatatc ttgagatctg    11760
gtggacaccg gcactcccgc atcctctcca tcagctccaa gcactcctca agctgctcct    11820
tcttctcgtg tgctacaaag aaaccatggt acacggcagc gtccacccgc aggccatccc    11880
tcgacatagc atccaagaac tcgtacccct gggat                               11915

SEQ ID NO: 24           moltype = DNA   length = 1127
FEATURE                 Location/Qualifiers
source                  1..1127
                        mol_type = other DNA
                        organism = synthetic construct
SEQUENCE: 24
tcttgttgga gccacctctc tcggacgatc gccaaagacg gataaggccg aagccgtcac     60
ttcagaccgc gctcatgcgc cgtagcagac tcctacatag cagggccagg gtatgtggac    120
ctttgcaagt ttaggattgg aaccagcgac cagaatccac aagattggag caaacgacca    180
aaaattcaca aggattggcg gctgacattg ccagcgcggg atcgcatgcg gcggcggcgg    240
ccggggcgag cacgggacga ggcgacagtc gagctccatt ggaacgtgaa aatacttaag    300
ggcaaggtct ccaaatactt gaaaaaatag gaaaaagaag aaaatacatg aaatgatatt    360
gaaatcaatt ggaagatgtt atgaatcttg tttttgcaaa gcgaacgatt cagatggcaa    420
aactatgaat cttttgtttt gaagtcccaa atataaaatt ttctcgtact caccaacatt    480
ggtgcgcacc tgtgattggc tcataaaaat tcttgggagg acggaagaaa gagtgaaggg    540
ataagcaagt aaaagcgctc aaactttccc ttctatggtc ccgtttgttt agtttaaact    600
gaaggcggga aacgacaatc tgatcatgag cggagaatta agggagtcac gttatgaccc    660
ccgccgatga cgcgggacaa gccgttttac gtttggaact gacagaaccg caacgttgaa    720
ggagccactc agcaagctta ctagtagcgc tgtttaaacg ctcttcaact ggaagagcgg    780
ttacccggac cgaagcttgc atgcctgcag tgcagcgtga cccggtcgtg ccctctcta    840
gagataatga gcattgcatg tctaagttat aaaaaattac cacatatttt ttttgtcaca    900
cttgtttgaa gtgcagttta tctatcttta tacatatatt taaactttac tctacgaata    960
atataatcta tagtactaca ataatatcag tgttttagag aatcatataa atgaacagtt    1020
agacatggtc taaaggacaa ttgagtattt tgacaacagg actctacagt tttatctttt    1080
tagtgtgcat gtgttctcct ttttttttgc aaatagcttc acctata               1127

SEQ ID NO: 25           moltype = DNA   length = 27
FEATURE                 Location/Qualifiers
source                  1..27
                        mol_type = other DNA
                        organism = synthetic construct
SEQUENCE: 25
tttaaactga aggcggaaac gacaatc                                         27

SEQ ID NO: 26           moltype = DNA   length = 11857
FEATURE                 Location/Qualifiers
source                  1..11857
                        mol_type = other DNA
                        organism = synthetic construct
SEQUENCE: 26
ctgagcgcac aacagcgagt cgcatggcac cggacgacat gagcgagatt tagatcggag     60
ggtgcggaca tggggcaacc tgcgcagcta acgcagggat ccacgcgacc accaacgaag    120
ccaagccccgg gcacgtcccc aggcaggttg ggccctggtt ccaccagcgg atgcatgcag    180
tgaagcgaca acggagagac aagccgaggg cgcgggtggg aatggcgtcc gggaggacga    240
gtggaggaga agaatctaga ggcatcgaga ttcgagaage cgacggagac aagattcgtg    300
tgggggggaga caaaccgcgg ggctgagcgc cgttgatatg ggatcagacg gtgtggataa    360
aaaaagtgac gttgatagaa cgtctggcca gtgaaaaaac aaaacaactc caacaaaata    420
cttttaaaagc tcttatacccc taaatgtagg ggatcaaaca cgtctctaca ctatttagca    480
gcgtcctcta aatgatcctc taaatttaga gaacgctact agattctcta tatatagttt    540
ctctaaacga tcttttatcc atttaaatac tttaaataac cggtttaaca aaactaaaat    600
atatacaata catttgagag tatgacaaat acgtatgtat aaaaataaaa aataaaataa    660
tgtattagtc tactttgaat cttctttttct tcataatata atgatgtata gctctcatgt    720
gcgttgagaa aaaagttaga gctagacgtt taatgtgtga cagtcgtt cgacgaaatc     780
tccctaatga gatgaattac tggaggttcc atcagaaagt cccctgaaaa gaggcattta    840
tttagtttag tcagcaattt ctgggaacac aaatatctt ttgttatcac cactattaaa    900
aatctatggt tataacttat aataacatga aaaataatt tagcatccca tatatataaa    960
aactgaagga agccatatat actaacataa gttaggagaa actaagaagg ttgtgcaaag   1020
cttgcactgc tccaaaatac tgcaaacaac cactctcctc taccaaccaa agaaactcat   1080
gtactccctc cgttcttttt tatttgtcgc attttagttt aaaaatgaac tagcagtcga   1140
caaatattcg agaacagata tagtatatac taacataact taggagatac taagaaagtt   1200
gcgcagagct tcactgttc caaattactg caaagcctct cccctctgcc agtacatcta   1260
cgagatgttt cagttaaaca aagattcaga caagtgatga gccactctt gtcatagatt    1320
gtgtggtcaa ccaacccatt gatgccacgg tttttgtgca tcatgcttt tgtattaaaa    1380
catcagttat gttaccatg tccgatatgc tctacataat gacaatcaac ttggtgttca   1440
ttatatttac aatgttagga atttcaatag ctacgaacac ttcaatagaa gtgccttgt   1500
gggatcacct taatgtgttg ttgatgtaag gagaagaatc ttaatttact cttgctaaat   1560
ttgaactaca caaaaccact gcactgagga ttgtcctaat aaattactgc tcatacacgt   1620
tagcatctgt tcagatactg agctaatccc taggattaaa ggatttgtaa aagatatgcc   1680
```

```
caatcattca ttttagttat ttatttctta gttatccact tgaagattta catacatttg 1740
aaataaattt cttagaggta aagtgaaaat cagttattta aatacatttt agttatttat 1800
tttcttcttt ttcctaattt ttccttgtat ttgaagtctg aaaagataac tttgcccttta 1860
tacatatttt atcttctacg tacgcatctg aacaacgtct ctttgtcccc tgatcgtgca 1920
gcaattagtg ctatgaatcg cgtttaagcg ctgcaaaatc atggctgggg cttcgtcctc 1980
gagtcgtcct gctgctcgat gtcacctcga gtcccgcacc gacctcagtg cttgttcttg 2040
ttggagccac ctctctcgga cgatcgccaa agacggataa ggccgaagcc gtcacttcag 2100
accgcgctca tgcgccgtag cagactccta catagcaggg ccagggtatg tggaccttg 2160
caagtttagg attggaacca gcgaccagaa tccacaagat tggagcaaac gaccaaaaat 2220
tcacaaggat tggcggctga cattgccagc gcgggatcgc atgcggcggc ggcggccggg 2280
gcgagcacgg gagcaggcga cagtcgagct ccattggaac gtagaaatac ttaagggcaa 2340
ggtctccaaa tacttgaaaa aataggaaaa agaagaaaat acatgaaatg atattgaaat 2400
caattggaag atgtttatgaa tcttgttttt gcaaagcgaa cgattcagat ggcaaaacta 2460
tgaatctttt tgtttgaagt cccaaatata aaattttctc gtactcacca acattggtgc 2520
gcacctgtga ttggctcata aaaattcttg gagggacgaa agaaagagtg agatcatgag 2580
cggagaatta agggagtcac gttatgaccc ccgccgatga cgcgggacaa gccgttttac 2640
gtttggaact gacagaaccg caacgttgaa ggagccactc agcaagctta ctagtagcgc 2700
tgtttaaacg ctcttcaact ggaagagcgg ttacccgaac cgaagcttgc atgcctgcag 2760
tgcagcgtga cccggtcgtg cccctctcta gagataatga gcattgcatg tctaagttat 2820
aaaaaattac cacatatttt ttttgtcaca cttgtttgaa gtgcagttta tctatctta 2880
tacatatatt taaactttac tctacgaata atataatcta tagtactaca ataatatcag 2940
tgttttagag aatcatataa atgaacagtt agacatgtca taaaggacaa ttgagtattt 3000
tgacaacagg actctacagt tttatctttt tagtgtgcat gtgttctcct ttttttttgc 3060
aaatagcttc acctatataa tacttcatcc attttattag tacatccatt tagggtttag 3120
ggttaatggt ttttatagac taattttttt agtacatcta ttttattcta ttttagcctc 3180
taaattaaga aaactaaaac tctatttag ttttttttatt taataattta gatataaat 3240
agaataaaat aaagtgacta aaaattaaac aaatacccct taagaaatta aaaaaactaa 3300
ggaaacattt ttcttgtttc gagtagataa tgccagcctg ttaaacgccg tcgacgagtc 3360
taacggacac caaccagcga accagcagcg tcgcgtcggg ccaagcgaag cagacggcac 3420
ggcatctctg tcgctgcctc tggacccctc tcgagagttc cgctccaccg ttggacttgc 3480
tccgctgtcg gcatccagaa attgcgtggc ggagcggcag acgtgagccg gcacggcagg 3540
cggcctcctc ctcctctcac ggcaccggca gctacggggg attccttccc caccgctcct 3600
tcgctttccc ttcctcgccc gccgtaataa atagacaccc cctccacacc ctctttcccc 3660
aacctcgtgt tgttcggagc gcacacacac acaaccagat ctccccaaa tccaccgtg 3720
ggcacctccg cttcaaggta cgccgctcgt cctcccccc ccccctctc taccttctct 3780
agatcggcgt tccggtccat ggttagggcc cggtagttct acttctgttc atgttgtgt 3840
tagatccgtg tttgtgttag atccgtgctg ctagcgttcg tacacggatg cgacctgtac 3900
gtcagacacg ttctgattgc taacttgcca gtgttctct ttggggaatc ctgggatggc 3960
tctagccgtt ccgcagacgg gatcgatttc atgattttt ttgtttcgtt gcataggtt 4020
tggtttgccc ttttccttta tttcaatata tgccgtgcac ttgtttgtcg ggtcatcttt 4080
tcatgctttt ttttgtcttg gttgtgatga tgtggtctgg ttgggcggtc gttctagatc 4140
ggagtagaat tctgtttcaa actacctggt ggatttatta attttggatc tgtatgtgtg 4200
tgccatacat attcatagtt acgaattgaa gatgatgat ggaaatatcg atctaggata 4260
ggtatacatg ttgatgcggg ttttactgat gcatatacag agatgctttt tgttcgcttg 4320
gttgtgatga tgtggtgtgg ttgggcggtc gttcattcgt tctagatcgg agtagaatac 4380
tgtttcaaac tacctggtgt atttattaat tttgaactg tatgtgtgtg tcatacatct 4440
tcatagttac gagtttaaga tggatgaaa tatcgatgta ggataggtat acatgttgat 4500
gtgggttta ctgatgcata tacatgatgg catatgcagc atctattcat atgctctaac 4560
cttgagtacc tatctattat aataaacaag tatgttttat aattattttg atcttgatat 4620
acttggatga tggcatatgc agcagctata tgtggatttt tttagccctg ccttcatacg 4680
ctatttattt gcttggtact gtttcttttg tcgatgctca ccctgttgtt tggtgttact 4740
tctgcaggtc gactctagag gatccacacg acaccatgtc cgcccgcgag gtgcacatcg 4800
acgtgaacaa caagaccggc cacacccctcc agctggagga caagaccaag ctcgacggcg 4860
gcaggtggcg cacctcccccg accaacgtgg ccaacgacca gatcaagacc ttcgtggccg 4920
aatccaacgg cttcatgacc ggcaccgagg gcaccatca ctactcaatt aatggcgagg 4980
ccgagatcag cctctacttc gacaaccgt tcgccggctc caacaaatac gacggccact 5040
ccaacaagtc ccagtacgag atcatcaccc agggcggctc cggcaaccag tcccacgtga 5100
cctacaccat ccagaccacc tcctcccgct acggccacaa gtcctgagtc atgagtcatg 5160
agtcagttga cctagacttg tccatcttct ggattggcaa acttaattaa tgtatgaaat 5220
aaaaggatgc acacatagtg acatgctaat cactataatg tgggcatcaa agttgtgtgt 5280
tatgtgtaat tactagttat ctgaataaaa gagaaagaga tcatccatat ttcttatcct 5340
aaatgaatgt cacgtgtctt tataattctt tgatgaacca gatgcatttc attaaccaaa 5400
tccatataca tataaaatatt aatcatatat aattaatatc aattgggtta gcaaaacaaa 5460
tctagtctag gtgtgttttg cgaatgcggc cgcggaccga attggggatc tgcatgaaag 5520
aaactgtcgc actgctgaac cgcaccttg cactttcatc gaacacgacc tgtgcccaag 5580
atgacggtgc tgcggtctaa gtgaggctga attgccttgg acagaagcgg actccctaca 5640
attagttagg ccaaacggtg catccatgtg tagctccggg ctcgggctgt atcgccatct 5700
gcaatagcat ccatggagct cgttccatgt agttggagat gaaccaatga tcgggcgtgt 5760
ggacgtatgt tcctgtgtac tccgatagta gagtacgtgt tagctctttc attggtgcaa 5820
tgaaatttgt gttggtttaa ttaccccctac gttagttgcg ggacaggaga cacatcatga 5880
atttaaaggc gatgatgtcc tctcctgtaa tgttattctt ttgatgtgat gaatcaaaat 5940
gtcatataaa acatttgttg ctctttagtt aggcctgatc gtagaacgaa atgctcgtgt 6000
agcggggcta cgagcctatg acgcaataac actggtttgc cggccggag tcgcttgaca 6060
aaaaaaagca tgttaagttt aaatttacaatt caaaacctaa catattatt tccctcaaag 6120
caggttcacg atcacacctg tacctaaaaaa aaacatgaag aatatattac tccattatta 6180
tgagatgaac cacttggcaa gagtggtaag ctatatataaaa aaatgaacat tattacgaga 6240
tgttatatgc cattatattg attcgaagat atatgtttct ttctcccacg ggcacctaac 6300
ggatacatga taaggccaag gcagatcacg ggaaattatt cgaatacatg ttcgccctta 6360
ttgccggaaa aaaaatgcag ggcaggtgtt ggccgtagcg atttaagcac ttaagctgga 6420
```

```
ggttgccaca cttggatgca agcgtctgac ccttctaaaa catcggcggc tttgtccgta  6480
tccgtatccc ctatccgaca tctagctggc cacacgacgg ggctgggcag atcgtggatg  6540
ccgggtcgac gtcgatcgtc agccatcata gaccaatcga ccatctgtta tggatgcttg  6600
ctagctagac tagtcagaca taaaatttgg atactttctc ccaactggga gacggggact  6660
gatgtcgaac tgcacgtgag ctaaattttt ccctataaat atgcatgaaa tactgcatta  6720
tcttgccaca gccactgcca cagccagata acaagtgcag ctggtagcac gcaacgcata  6780
gctctggact tgtagctagg tagccaaccg gatccacacg acaccatgct cgacaccaac  6840
aaggtgtacg agatcagcaa ccacgccaac ggcctctacg ccgccaccta cctctcccctc  6900
gacgactccg gcgtgtccct catgaacaag aacgacgacg acatcgacga ctacaacctc  6960
aagtggttcc tcttcccgat cgacgacgac cagtacatca tcacctccta cgccgccaac  7020
aactgcaagg tgtggaacgt gaacaacgac aagattaatg tgtcaaccta ctcctccacc  7080
aactccatcc agaagtggca gatcaaggcc aacggctcct cctacgtgat ccagtccgac  7140
aacggcaagg tgctcaccgc cggcaccggc caggccctcg gcctcatccg cctcaccgac  7200
gagtcctcca acaacccgaa ccagcaatgg aacctgcagc ccgtgcagac catccagctc  7260
ccgcagaagc cgatcatcga caccaagctc aaggactacc cgaagtactc cccgaccggc  7320
aacatcgaca acggcacctc cccgcagctc atgggctgga ccctcgtgcc gtgcatcatg  7380
gtgaacgacc cgaacatcga caagaacacc cagatcaaga ccaccccgta ctacatcctc  7440
aagaagtacc agtactggca gagggccgtg ggctccaacg tcgcgctccg cccgcacgag  7500
aagaagtcct acacctacga gtggggcacc gagatcgacc agaagaccac catcatcaac  7560
accctcggct ccagatcaa catcgacagc ggcatgaagt tcgacatccc ggaggtgggc  7620
ggcggtaccg acgagatcaa gacccagctc aacgaggagc tcaagatcga gtattcacat  7680
gagacgaaga tcatggagaa gtaccgagag cagtccgaga tcgacaaccc gaccgaccag  7740
tccatgaact ccatcggctt cctcaccatc acctccctgg agctctaccg ctacaacggc  7800
tccgagatcc gcatcatgca gatccagacc tccgacaacg acacctacaa cgtgacctcc  7860
tacccgaacc accagcaggc cctgctgctg ctgaccaacc actcctacga ggaggtggag  7920
gagatcaacca acatcccgaa gtccacccctc aagaagctca agaagtacta cttctgagtc  7980
atgagtcatg agtcagttaa cctagacttg tccatcttct ggattggcca acttaattaa  8040
tgtatgaaat aaaaggatgc acacatagtg acatgctaat cactataatg tgggcatcaa  8100
agttgtgtgt tatgtgtaat tactagttat ctgaataaaa gagaaagaga tcatccatat  8160
ttcttatcct aaatgaatgt cacgtgtctt tataattctt tgatgaacca gatgcatttc  8220
attaaccaaa tccatataca tataaatatt aatcatatat aattaatatc aattgggtta  8280
gcaaaacaaa tctagtctag gtgtgttttg cgaattccca tggagtcaaa gattcaaata  8340
gaggacctaa cagaactcgc cgtaaagact ggcgaacagt tcatacagag tctcttacga  8400
ctcaatgaca agaagaaaat cttcgtcaac atggtggagc acgacacgct tgtctactcc  8460
aaaaaatatca aagatacagt ctcagaagac caaagggcaa ttgagacttt tcaacaaagg  8520
gtaatatccg gaaacctcct cggattccat tgcccagcta tctgtcactt tattgtgaag  8580
atagtggaaa aggaaggtgg ctcctacaaa tgccatcatt gcgataaagg aaaggccatc  8640
gttgaagatg cctctgccga cagtggtccc aaagatggac ccccacccac gaggagcatc  8700
gtggaaaaag aagacgttcc aaccacgtct tcaaagcaag tggattgatg tgatatctcc  8760
actgacgtaa gggatgacgc acaatcccac tatccttcgc aagacccttc ctctatataa  8820
ggaagttcat tcatttggga ggacaggg tacccgggga tccaccatgt ctccggagag  8880
gagaccagtt gagattaggc cagctacagc agctgatatg gccgcggttt gtgatatcgt  8940
taaccattac attggagacg ctacagtgaa ctttaggaca gccacacaaa caccacaaga  9000
gtggattgat gatctagaga ggttgcaaga tagatacct tggttggttg ctgaggttga  9060
gggtgttgtg ctggtattgg cttacgctgg gccctggaag gctaggaacg cttacgattg  9120
gacagttgag agtactgttt acgtgtcaca taggcatcaa aggttgggcc taggatccac  9180
attgtacaca cattttgctta agtctatgga ggcgcaagt tttaagtctg tggttgctgt  9240
tataggcctt ccaaacgatc catctgttag gttgcatgag gctttgggat acacagcccg  9300
gggtacattg cgcgcagctg gatacaagca tggtggatgg catgatgttg gtttttggca  9360
aagggatttt gagttgccag ctcctccaag gccagttagg ccagttaccc agatctgagt  9420
cgacctgcag gcatgcccgc tgaaatcacc agtctctctc tacaaatcta tctctctcta  9480
taataatgtg tgagtagttc ccagataagg gaattagggt tcttataggg tttcgctcat  9540
gtgttgagca tataagaaac ccttagtatg tatttgtatt tgtaaaatac ttctatcaat  9600
aaaatttcta attcctaaaa ccaaaatcca gggcgagctc ggtacccggg gatcctctag  9660
agtcgacctg caggcatgcc gcggatcgatc gatgggcccc ggccgaagct tcggtccggg  9720
ccatcgtggc ctcttgctct tcaggatgaa gagctatgtt taaacgtgca agcgctcaat  9780
tcgccctata gtgagtcgta ttacaatcgt acgcaattca gtacattaaa acgtccgca  9840
atgtgttatt aagttgtcta agcgtcaatt tttcccttct atggtcccgt tgtttatcc  9900
tctaaattat ataatccagc ttaaataagt taagagacaa acaaacaaca cagattatta  9960
aatagattat gtaatctaga tacctagaat atgtaatcca taagtagaat atcaggtgct 10020
tatataatct atgagctcga ttatataatc ttaaagaaa acaaacagag ccccctataaa 10080
aagggggtcaa gtgacactt ggtcactcat ttaatccctc cctctcctct tttatccctc 10140
ttttttggtgt attcaccaat agtggtgtgc acctgtgatt ggctcgtaaa aattcttgga 10200
cggatggaaa agtgaagaga taagcaagtc aagaaaaagt aacaacgaag cttcatcagc 10260
tacaaattttt ggcccaactg gttgcaccag caccaaactt acgtatacat gattatctct 10320
gtttccctca tttcgaagaa aaaacgggt ttcaaaccc actgctttca ggagtaaaaa 10380
aagataataa tctgaaacat tgcttccacc ttggccctta tttggttacg ttgcaattca 10440
ccccaatcca catgtggatt gagatggatt gcagtgtagc tagacaaacc cttaggccct 10500
gtttgcatag gaatacacca ggaattattc cagctaatca aaattatat aaatgagaga 10560
aacaattcgg ataggaattg ttccaggact tcattctgca gtaaccgaac ggccccttaa 10620
tccacccaa tacacgtgga ttggagtgga ttgaggtaca gccaaacaag gcctaagtgc 10680
agatcaaata aatcacccgt catattcttc tacctacaaa aacagcaata aacacctgaa 10740
tgaagttcta atttgcacag tgtaggtagg atgaaaatag ttacctcctc atggtcagta 10800
actcttggca cacaacttca catgtaatcg atgtaccat tggctcttgc ctgaaaccca 10860
atacatcttt agcataagaa taatattatg atggcaaggc atgatcacca gcactccttt 10920
attgtttagt aagtctatca ctccccaaaa caattcaaat gaacagagat gcattgcccc 10980
caatgaattc tatttcaatt agccggaaaa ttctacttca tcagaagcat ccaaattgcc 11040
agcatcccta ctagactgac catgaccagg ctgccgcaga tgcctctttt tctgtcctct 11100
cctctttgcc ttgagtttct cttcaagatc cctcacccca cgtctcttat acatcttaaa 11160
```

```
gctaacatgt ctctcctccg ccatcttcct aaccttctca gtaatctcag cagcaatctg  11220
acggttgtac aacttcttca gccccttcat caactttgca aatgtgtcag gctgtggcat  11280
cagtcctgcc tctagcatgt ctaagcaata caggcaggcc tccttgacat gtttcttcgc  11340
aaacagtgca tgaatccaga tagtccatgc actcacattg agctcacagc ctttgctcac  11400
aatacatttc caaacatcct ttgcaagctc aagtttctca tctctgacca acgcattgag  11460
gaggtccttc agcaccccat attgcgtac cacaaagagc cccctcccaa ccatgtcttt  11520
aaaataacta catgcctcaa tcagcaaacc ctgcccaaca aggccactca ccacgatagc  11580
aaatgtatcg accacaggac tgagcccagc actttccatc tcattccaca atgtcatggc  11640
ttgcttggtc tccccaagcc tgcaggccaa ccgaatcaac acattgtata tcttgagatc  11700
tggtggacac cggcactccc gcatcctctc catcagctcc aagcactcct caagctgctc  11760
cttcttctcg tgtgctacaa agaaaccatg gtacacggca gcgtccaccc gcaggccatc  11820
cctcgacata gcatccaaga actcgtaccc ctgggat                           11857

SEQ ID NO: 27            moltype = DNA   length = 11883
FEATURE                  Location/Qualifiers
source                   1..11883
                         mol_type = other DNA
                         organism = synthetic construct
SEQUENCE: 27
ctgagcgcac aacagcgagt cgcatggcac cggacgacat gagcgagatt tagatcggag    60
ggtgcggaca tggggcaacc tgcgcagcta acgcagggat ccacgaccc accaacgaag   120
ccaagcccgg gcacgtcccc aggcaggttg ggccctggtt ccaccagcgg atgcatgcag   180
tgaagcgggg acggagagac aagccgaggg cgcgggtggg aatggcgtcc gggaggacga   240
gtggaggaga agaatctaga ggcatcgaga ttcgagaagc cgacggagac aagattcgtg   300
tgggggggaga caaaccgcgg ggctgagcgc cgttgatatg ggatcagacg gtgtggaata   360
aaaaagtgac gttgatagaa cgtctggcca gtgaaaaaac aaaacaactc caacaaaata   420
ctttaaaagc tcttataccc taaatgtagg ggatcaaaca cgtctctaca ctatttagca   480
gcgtcctcta aatgatcctc taaatttaga gaacgctact agattctcta tatatagttt   540
ctctaaacga tcttttatcc atttaaatac tttaaataac cggtttaaca aaactaaaat   600
atatacaata catttgagag tatgacaaat acgtatgtat aaaaataaaa aataaaataa   660
tgtattagtc tactttgaat cttcttttct tcataataa atgatgtata gctctcatgt   720
gcgttgagaa aaaagttaga gctagacgtt taatgtgtag tgacagtctt cgacgaaatc   780
tccctaatga gatgaattac tggaggttcc atcagaaagt cccctgaaaa gaggcattta   840
tttagtttag tcagcaattt ctgggaacac aaatattcct ttgttatcac cactattaaa   900
aatctatggt tataacttat aataacatga aaaaataatt tagcatccca tatatataaa   960
aactgaagga agccatatat actaacataa gttaggagaa actaagaagg ttgtgcaaag  1020
cttgcactgc tccaaaatac tgcaaacaac cactctcctc taccaaccaa agaaactcat  1080
gtactcccctc cgttctttt tatttgtcgc attttagttt aaaaatgaac tagcagtcga  1140
caaatattcg agaacagata tagtatatac taacataact taggagatac taagaaagtt  1200
gcgcagagct ttcactgttc caaattactg caaagcctct cccctctgcc agtacatcta  1260
cgagatgttt cagttaaaca aagattcaga caagtgatga gccacttctt gtcatagatt  1320
gtgtggtcaa ccaacccatt gatgccacgg ttttgtgca tccatgcttt tgtattaaaa  1380
catcagttat gtttaccatg tccgatatgc tctacataat gacaatcaac ttggtgttca  1440
ttatatttac aatgttagga attttcaatag ctacgaacac ttcaataaa gtgcctttgt  1500
gggatcacct taatgtgttg ttgatgtaag gagaagaatc ttaatttact cttgctaaat  1560
ttgaactaca caaaaccact gcactgagga ttgtcctaat aaattactgc tcatacacgt  1620
tagcatctgt tcagatactg agctaatccc taggattaaa ggatttgtaa aagatatgcc  1680
caatcattca ttttagttat ttatttctta gttatccact tgaagattta catacatttg  1740
aaataaattt cttagaggta aagtgaaaat cagttatttta aatacatttt agttatttat  1800
tttcttcttt ttcctaattt ttccttgtat ttgaagtctg aaaagataac tttgcccttta  1860
tacatatttt atcttctacg tacgcatctg aacaacgtct ctttgtcccc tgatcgtcga  1920
gcaattagtg ctatgaatcg cgtttaagcg ctgcaaaatc atggctgggg cttcgtcctc  1980
gagtcgtcct gctgctcgat gtcacctcga gtcccgcacc gacctcagtg cttgttcttg  2040
ttggagccac ctctctcgga cgatcgcaa agacggataa ggccgaagcc gtcacttcag  2100
accgcgctca tgccgcgtag cagactccta catgcaggg ccagggtatg tggacctttg  2160
caagtttagg attggaacca gcgaccagaa tccacaagat tggagcaaac gaccaaaaat  2220
tcacaaggat tggcggctga cattgccagc gcgggatcgc atgcggcggc ggcggccggg  2280
gcgagcacgg gagcaggcga cagtcgagct ccattggaac gtagaaatac ttaagggcaa  2340
ggtctccaaa tacttgaaaa aataggaaaa agaagaaaat acatgaaatg atattgaaat  2400
caattggaag atgttatgaa tcttgttttt gcaaagcgaa cgattcagat ggcaaaacta  2460
tgaatctttt tgtttgaagt cccaaatata aaatttctc gtactcacca acattggtgc  2520
gcacctgtga ttggctcata aaattcttg gagggacgga agaaagagtg tttcccttct  2580
atggtcccgt ttgtttagat catgagcgga gaattaaggg agtcacgtta tgaccccgc  2640
cgatgacgcg ggacaagccg ttttacgttt ggaactgaca agccgcaac gttgaaggag  2700
ccactcagca agcttactag tagcgctgtt taaacgctct tcaactggaa gagcggttac  2760
ccggaccgaa gcttgcatgc ctgcagtgca gcgtgacccg tcgtgcccc tctctagaga  2820
taatgagcat tgcatgtcta agttataaaa aattaccaca tattttttt gtcacacttg  2880
tttgaagtgc agtttataca tctttataca tatatttaaa cttttactcta cgaatataat  2940
aatctatagt actacaataa tatcagtgtt ttagagaatc atataaatga acagttagac  3000
atggtctaaa ggacaattga gtattttgac aacaggactc tacagtttta tcttttttagt  3060
gtgcatgtgt tctccttttt ttttgcaaat agcttcacct atataatact tcatcccattt  3120
tattagtaca tccattttagg gtttagggtt aatggttttt atagactaat tttttagta  3180
catctatttt attctattt agcctctaaa ttaagaaac taaactcta tttttagtttt  3240
tttattttaat aattttagata taaaatagaa taaaataaaa ttaaacaaat  3300
acccttaag aaattaaaaa aactaaggaa acattttct tgtttcgagt agataatgcc  3360
agcctgttaa acgccgtcga cgagtctaac ggacaccaac cagcgaacca gcagcgtcgc  3420
gtcgggccaa gcgaagcaga cggcacggca tctctgtcgc tgcctctgga cccctctcga  3480
gagttccgct ccaccgttgg acttgctccg ctgtcggcat ccagaaattg cgtggcgag  3540
cggcagacgt gagccggcac ggcaggcggc ctcctcctcc tctcacggca ccggcagcta  3600
```

```
cgggggattc ctttcccacc gctccttcgc tttcccttcc tcgcccgccg taataaatag    3660
acaccccctc cacaccctct ttccccaacc tcgtgttgtt cggagcgcac acacacacaa    3720
ccagatctcc cccaaatcca cccgtcggca cctccgcttc aaggtacgcc gctcgtcctc    3780
cccccccccc cctctctacc ttctctagat cggcgttccg gtccatggtt agggcccggt    3840
agttctactt ctgttcatgt ttgtgttaga tccgtgtttg tgttagatcc gtgctgctag    3900
cgttcgtaca cggatgcgac ctgtacgtca gacacgttct gattgctaac ttgccagtgt    3960
ttctcttttgg ggaatcctgg gatggctcta gccgttccgc agacgggatc gatttcatga    4020
ttttttttgt ttcgttgcat agggtttggt ttgccctttt cctttatttc aatatatgcc    4080
gtgcacttgt ttgtcgggtc atcttttcat gcttttttt gtcttggttg tgatgatgtg    4140
gtctggttgg gcggtcgttc tagatcggag tagaattctg tttcaaacta cctggtggat    4200
ttattaattt tggatctgta tgtgtgtgcc atacatattc atagttacga attgaagatg    4260
atggatggaa atatcgatct aggataggta tacatgttga tgcgggtttt actgatgcat    4320
atacagagat gcttttttgtt cgcttggttg tgatgatgtg gtgtggttgg gcggtcgttc    4380
attcgttcta gatcggagta gaatactgtt tcaaactacc tggtgtattt attaattttg    4440
gaactgtatg tgtgtgtcat acatcttcat agttacgagt ttaagatgga tggaaatatc    4500
gatgtaggat aggtatacat gttgatgtgg gttttactga tgcatataca tgatggcata    4560
tgcagcatct attcatatgc tctaaccttg agtacctatc tattataata aacaagtatg    4620
ttttataatt attttgatct tgatatactt ggatgatggc atatgcagca gctatatgtg    4680
gattttttta gccctgcctt catacgctat ttatttgctt ggtactgttt cttttgtcga    4740
tgctcaccct gttgtttggt gttacttctg caggtcgact ctagaggatc cacacgacac    4800
catgtccgcc cgcgaggtgc acatcgacgt gaacaacaag accggccaca ccctccagct    4860
ggaggacaag accaagctcg acgcggcag gtggcgcaca tcccgacca acgtggccaa    4920
cgaccagatc aagaccttcg tggccgaatc caacggcttc atgaccggca ccgagggcac    4980
catctactac tcaattaatg gcgaggccga gatcagcctc tacttcgaca cccgttcgc    5040
cggctccaac aaatacgacg gccactccaa caagtcccag tacgagatca tcacccaggg    5100
cggctccggc aaccagtccc acgtgaccta caccatccag aacggtgatc catgtgtagc    5160
ccacaagtcc tgagtcatga gtcatgagtc agttaaccta gacttgtcca tcttctggat    5220
tggccaactt aattaatgta tgaaataaaa ggatgcacac atagtgacat gctaatcact    5280
ataatgtggg catcaaagtt gtgtgttatg tgtaattact agttatctga ataaaagaga    5340
aagagatcat ccatatttct tatcctaaat gaatgtcacg tgtctttata attctttgat    5400
gaaccagatg catttcatta accaaatcca tatacatata aatattaatc atatataatt    5460
aatatcaatt gggttagcaa aacaaatcta gtctaggtgt gttttgcgaa tcggccgcg    5520
gaccgaattg gggatctgca tgaaagaaac tgtcgcactg ctgaaccgca ccttgtcact    5580
ttcatcgaac acgacctgtg cccaagatga cggtgctgcg gtctaagtga ggctgaattg    5640
ccttggacag aagcggactc cctacaatta gttaggccaa acggtgcatc catgtgtagc    5700
tccgggctcg ggctgtatcg ccatctgcaa tagcatccat ggagctcgtt ccatgtagtt    5760
ggagatgaac caatgatcgg gcgtgtggac gtatgttcct gtgtactccg atagtagagt    5820
acgtgttagc tctttcatgg tgcaagtgaa atttgtgttg gtttaattac ccctacgtta    5880
gttgcgggac aggagacaca tcatgaattt aaaggcgatg atgtcctctc ctgtaatgtt    5940
attcttttga tgtgatgaat caaaatgtca tataaaacat ttgttgctct ttagttaggc    6000
ctgatcgtag aacgaaatgc tcgtgtagcg gggctacgag cctatgacgc aataacactg    6060
gtttgccggc ccggagtcgc ttgacaaaaa aaagcatgtt aagtttattt acaattcaaa    6120
acctaacata ttatattccc tcaaagcagg ttcacgatca cacctgtca taaaaaaaac    6180
atgaagaata tattactcca ttattatgag atgaaccact tggcaagagt ggtaagctat    6240
ataaaaaaat gaacattatt acgagatgtt atatgccatt atattgattc gaagatatat    6300
gtttctttct cccacgggca cctaacggat acatgataag gccaaggcag atcacggaa    6360
attattcgaa tacatgttac gccctattgc cggaaaaaaa atgcagggca ggtgttggcc    6420
gtagcgattt aagcacttaa gctgaggtt gccacacttg gatgcaagcg tctgacccttt    6480
ctaaaacatc ggcggctttg tccgtatccg tatccctat ccgacatcta gctgccaca    6540
cgacgggggct gggcagatcg tggatgccgg gtcgacgtcg atcgtcagcc atcatagacc    6600
aatcgaccat ctgttatgga tgcttgctag ctagactagt cagacataaa atttggatac    6660
tttctcccaa ctgggagacg gggactgatg tgcagctgca cgtgagctaa atttttccct    6720
ataaatatgc atgaaatact gcattatctt gccacagcca ctgccacagc cagataacaa    6780
gtgcagctgg tagcacgcaa cgcatagctc tggacttgta gctaggtagc caaccggatc    6840
cacacgacac catgctcgac accaacaagg tgtacgagat cagcaaccac gccaacgtcc    6900
tctacgccgc cacctacctc tccctcgacg actccggcgt gtccctcatg aacaagaacg    6960
acgacgacat cgacgactac aacctcaagt ggttcctctt cccgatcgac gacgaccagt    7020
acatcatcac ctcctacgcc gccaacaact gcaaggtgtg gaacgtgaac aacgacaaga    7080
ttaatgtgtc aacctactcc tccaccaact ccatccagaa gtggcagatc aaggccaacg    7140
gctcctccta cgtgatccag tccgacaacg gcaaggtgct caccgccggc accggccagg    7200
ccctcggcct catccgcctc accgacgagt cctccaacaa cccgaaccag caatggaacc    7260
tgacgtccgt gcagaccatc cagctcccgc agaagccgat catcgacacc aagctcaagg    7320
actacccgaa gtactcccccg accggcaaca tcgacaacgg cacctccccg cagctcatgg    7380
gctggaccct cgtgccgtgc atcatggtga acgacccgaa catcgacaag aacacccaga    7440
tcaagaccac cccgtactac atcctcaaga gtaccagta ctggcagagg gccgtgggct    7500
ccaacgtcgc gctccgcccg cacgagaaga agtcctacac ctacgagtgg ggcaccgaga    7560
tcgaccagaa gaccaccatc atcaacaccc tcggcttcca gatcaacatc gacagcggca    7620
tgaagttcga catcccggag gtgggcggcg gtaccgacga gatcaagacc cagctcaacg    7680
aggagctcaa gatcgagtat tcacatgaga cgaagatcat ggagaagtac caggagcagt    7740
ccgagatcga caacccgacc gaccagtcca tgaactccat cggcttcctc accatcaccct    7800
ccctggagct ctaccgctac aacggctccg agatccgcat catgcagatc cagacctccg    7860
acaacgcacc ctacaacgtg acctcctacc cgaaccacca gcaggcctg ctgctgctga    7920
ccaaccactc ctacgaggag gtggaggaga tcaccaacat cccgaagtcc accctccaaga    7980
agctcaagga gtactacttc tgagtcatga gttaaccta gacttgtcca    8040
tcttctggat tggccaactt aattaatgta tgaaataaaa ggatgcacac atagtgacat    8100
gctaatcact ataatgtggg catcaaagtt gtgtgttatg tgtaattact agttatctga    8160
ataaaagaga aagagatcat ccatatttct tatcctaaat gaatgtcacg tgtctttata    8220
attctttgat gaaccagatg catttcatta accaaatcca tatacatata aatattaatc    8280
atatataatt aatatcaatt gggttagcaa aacaaatcta gtctaggtgt gttttgcgaa    8340
```

```
ttcccatgga gtcaaagatt caaatagagg acctaacaga actcgccgta aagactggcg   8400
aacagttcat acagagtctc ttacgactca atgacaagaa gaaaatcttc gtcaacatgg   8460
tggagcacga cacgcttgtc tactccaaaa atatcaaaga tacagtctca gaagaccaaa   8520
gggcaattga gacttttcaa caaagggtaa tatccggaaa cctcctcgga ttccattgcc   8580
cagctatctg tcactttatt gtgaagatag tggaaaagga aggtggctcc tacaaatgcc   8640
atcattgcga taaaggaaag gccatcgttg aagatgcctc tgccgacagt ggtcccaaag   8700
atggaccccc acccacgagg agcatcgtgg aaaaagaaga cgttccaacc acgtcttcaa   8760
agcaagtgga ttgatgtgat atctccactg acgtaaggga tgacgcacaa tcccactatc   8820
cttcgcaaga cccttcctct atataaggaa gttcatttca tttggagagg acagggtacc   8880
cggggatcca ccatgtctcc ggagaggaga ccagttgaga ttaggccagc tacagcagct   8940
gatatggccg cggtttgtga tatcgttaac cattacattg agacgtctac agtgaacttt   9000
aggacagagc cacaaacacc acaagagtgg attgatgatc tagagaggtt gcaagataga   9060
taccctcggg tggttgctga ggttgagggt gttgtggctg gtattgctta cgctgggccc   9120
tggaaggcta ggaacgctta cgattggaca gttgagagta ctgtttacgt gtcacatagg   9180
catcaaaggt tgggcctagg atccacattg tacacacatt tgcttaagtc tatgggaggg   9240
caaggtttta agtctgtggt tgctgttata ggccttccaa acgatccatc tgttaggttg   9300
catgaggctt tgggatacac agcccggggt acattgcgcg cagctggata caagcatggt   9360
ggatggcatg atgttggttt ttggcaaagg gattttgagt tgccagctcc tccaaggcca   9420
gttaggccag ttacccagat ctgagtcgac ctgcaggcat gcccgctgaa atcaccagtc   9480
tctctctaca aatctatctc tctctataat aatgtgtgag tagttcccag ataagggaat   9540
tagggttctt ataggggtttc gctcatgtgt tgagcatata agaaacccttt agtatgtatt   9600
tgtatttgta aaatacttct atcaataaaa tttctaattc ctaaaaccaa aatccaggggc   9660
gagctcggta cccggggatc ctctagagtc gacctgcagg catgcccgcg gatatcgatg   9720
ggccccggcc gaagcttcgg tccgggccat cgtggcctct tgctcttcag gatgaagagc   9780
tatgttttaaa cgtgcaagcg ctcaattcgc cctatagtga gtcgtattac aatcgtacgc   9840
aattcagtac attaaaaacg tccgcaatgt gttattaagt tgtctaagcg tcaatttttc   9900
ccttctatgg tcccgtttgt ttatcctcta aattatataa tccagcttaa ataagttaag   9960
agacaaacaa acaacacaga ttattaaata gattatgtaa tctagatacc tagattatgt  10020
aatccataag tagaatatca ggtgcttata taatctatga gctcgattat ataatcttaa  10080
aagaaaacaa acagagcccc tataaaaagg ggtcaagtga acttggctg actcatttaa  10140
tccctccctc tcctcttta tccctctttt tggtgtattc accaatagtg gtgtgcacct  10200
gtgattggct cgtaaaaatt cttggacgga tggaagagtg aagagataag caagtcaaag  10260
aaaagtaaca acgaagcttc atcagctaca aattttggcc caactggttg caccagcacc  10320
aaacttacgt atacatgatt atctctgttt ccctcatttc gaagaaaaaa acgggtttca  10380
aaacccactg ctttcaggag taaaaaaaga taataatctg aaacattgct tccaccttgg  10440
cccttatttg gttacgttgc aattcacccc aatccacatg tggattgaga tggattgcag  10500
tgtagctaga caaacccta ggccctgttt gcataggaat acaccaggaa ttattccagc  10560
taatcaaaat ttatataaat gagagaaaca attcggatga gaattgttcc aggacttcat  10620
tctgcagtaa ccgaacggcc cctaatcca ccccaataca cgtggattgg agtggattga  10680
ggtacagcca aacaaggcct aagtgcagat caaatataatc acccgtcata ttcttctacc  10740
tacaaaaaca gcaataaaca cctgaatgaa gttctaattt gcacagtgta ggtaggatga  10800
aaatagttac ctcctcatgg tcagtaactc ttggcacaca acttcacatg taatcgatgt  10860
accacttggc tcttgcctga aacccaatac atctttagca taagaataat attatgatgg  10920
caaggcatga tcaccagcac tcctttattg tttagtaagt ctatcactcc caaaacaat  10980
tcaaatgaac agagatgcat tgcccccaat gaattctatt tcaattagcc ggaaaattct  11040
acttcatcag aagcatccaa attgccagca tccctactag actgaccatg accaggctgc  11100
cgcagatgcc tcttttttctg tcctctcctc tttgccttga gtttctcttc aagatccctc  11160
accccacgtc tcttatacat cttaaagcta acatgtctct cctccgccat cttcctaacc  11220
ttctcagtaa tctcagcagc aatctgacgg ttgtacaact tcttcagccc cttcatcaac  11280
tttgcaaatg tgtcaggctg tggcatcagt cctgcctcta gcatgtctaa gcaatacagg  11340
caggcctcct tgcatgtttt cttcgcaaac agtgcataaa tccagatagt ccatgcactc  11400
acattgagct cacagccttt gctcacaata catttccaaa catcctttgc aagctcaagt  11460
ttctcatctc tgaccaacgc attgaggagg tccttcagca ccccatattg cggtaccaca  11520
aagagccccc tcccaaccat gtcttttaaaa taactacatg cctcaatcag caaaccctgc  11580
ccaacaggc cactccaccac gatagcaaat gtatcgacaa caggactgag cccagcactt  11640
tccatctcat tccacaatgt catggcttgc ttggtctccc caagcctgca ggccaaccga  11700
atcaccacat tgtatatctt gagatctggt ggacaccggc actcccgcat cctctccatc  11760
agctccaagc actcctcaag ctgctccttc ttctcgtgtg ctacaaagaa accatggtac  11820
acggcagcgt ccaccgcag gccatccctc gacatagcat ccaagaactc gtaccctgg  11880
gat                                                                 11883
```

SEQ ID NO: 28        moltype = DNA   length = 1068
FEATURE              Location/Qualifiers
source               1..1068
                     mol_type = other DNA
                     organism = synthetic construct
SEQUENCE: 28

```
tcttgttgga gccacctctc tcggacgatc gccaaagacg gataaggccg aagccgtcac     60
ttcagaccgc gctcatgcgc cgtagcagac tcctacatag cagggccagg gtatgtggac    120
ctttgcaagt ttaggattgg aaccagcgac cagaatccac aagattggag caaacgacca    180
aaaattcaca aggattggcg gctgacattg ccagcgcggg atcgcatgcg gcggcggcgg    240
ccggggcgag cacgggagca ggcgacagtc gagctccatt ggaacgtaga aatacttaag    300
ggcaaggtct ccaaatactt gaaaaatag aaaaagaag aaaatacatg aaatgatatt    360
gaaatcaatt ggaagatgtt atgaatcttg tttttgcaaa gcgaacgatt cagatgcaa    420
aactatgaat cttttttgttt gaagtcccaa atataaaatt ttctcgtact caccaacatt    480
ggtgcgcacc tgtgattggc tcataaaat tcttgagggg acggaagaaa gagtgtttcc    540
cttctatggt cccgtttgtt tagatcatga gcggagaatt aagggagtca cgttatgacc    600
cccgccgatg acgcgggaca agccgtttta cgtttgaac tgcagaacc gcaacgttga    660
aggagccact cagcaagctt actagtagcg ctgtttaaac gctcttcaac tggaagagcg    720
```

-continued

```
gttacccgga ccgaagcttg catgcctgca gtgcagcgtg acccggtcgt gcccctctct    780
agagataatg agcattgcat gtctaagtta taaaaaatta ccacatattt tttttgtcac    840
acttgtttga agtgcagttt atctatcttt atacatatat ttaaacttta ctctacgaat    900
aatataatct atagtactac aataatatca gtgttttaga gaatcatata aatgaacagt    960
tagacatggt ctaaaggaca attgagtatt ttgacaacag gactctacag ttttatcttt   1020
ttagtgtgca tgtgttctcc ttttttttg caaatagctt cacctata                 1068
```